US008680141B2

(12) United States Patent
Reddell et al.

(10) Patent No.: US 8,680,141 B2
(45) Date of Patent: Mar. 25, 2014

(54) SPIROKETALS

(71) Applicant: EcoBiotics Ltd, Yungaburra (AU)

(72) Inventors: Paul Warren Reddell, Yungaburra (AU); Victoria Anne Gordon, Yungaburra (AU)

(73) Assignee: EcoBiotics Ltd, Yungaburra, Queensland (AU)

( * ) Notice: Subject to any disclaimer, the term of this patent is extended or adjusted under 35 U.S.C. 154(b) by 0 days.

(21) Appl. No.: 13/896,587

(22) Filed: May 17, 2013

(65) Prior Publication Data
US 2013/0324596 A1 Dec. 5, 2013

Related U.S. Application Data

(63) Continuation of application No. 13/208,210, filed on Aug. 11, 2011, now Pat. No. 8,466,194, which is a continuation of application No. 12/158,420, filed as application No. PCT/AU2006/002000 on Dec. 22, 2006, now Pat. No. 8,013,012.

(30) Foreign Application Priority Data

Dec. 23, 2005 (AU) .............................. 2005907277

(51) Int. Cl.
*A61K 31/35* (2006.01)
*C07D 311/00* (2006.01)

(52) U.S. Cl.
USPC ............................ 514/456; 514/464; 549/344

(58) Field of Classification Search
USPC ................................... 514/456, 464; 549/344
See application file for complete search history.

(56) References Cited

FOREIGN PATENT DOCUMENTS

EP          0 997 472 A2      5/2000
WO          WO 00/00514 A2    1/2000

OTHER PUBLICATIONS

Kwon et al., "New Cytotoxic Butanolides from *Lindera obtusiloba* Blume," *Chem. Pharm. Bull.* 48(5): 614-616, 2000.
Killeen et al., "The Phase 2 Enzyme Inducers Ethacrynic Acid, DL-Sulforaphane, and Oltipraz Inhibit Lipopolysaccharide-Induced High-Mobility Group Box 1 Secretion by RAW 264.7 Cells," *The Journal of Pharmacology and Experimental Therapeutics 316*(3): 1070-1079, 2006.

*Primary Examiner* — Samantha Shterengarts
(74) *Attorney, Agent, or Firm* — Seed IP Law Group PLLC

(57) ABSTRACT

The present invention relates to spiroketal compounds that are useful in methods of treating or preventing protozoal infections, parasitic infections, bacterial infections, cell proliferative disorders and anti inflammatory disorders. The spiroketal compounds are also useful as immunosuppressive agents, and also in methods of controlling pests.

26 Claims, 6 Drawing Sheets

SPIROKETALS

CROSS-REFERENCE TO RELATED APPLICATION

This application is a continuation of U.S. patent application Ser. No. 13/208,210, filed Aug. 11, 2011 (now allowed); which is a continuation of U.S. patent application Ser. No. 12/158,420, filed Nov. 19, 2008 (U.S. Pat. No. 8,013,012); which is a U.S. National Stage entry of PCT/AU2006/002000 filed Dec. 22, 2006; which claims priority to Australian Application No. 2005907277, filed Dec. 23, 2005. All of these applications are incorporated by reference herein in their entireties.

FIELD OF THE INVENTION

This invention relates to bioactive molecules. More particularly, this invention relates to spiroketals of potential therapeutic benefit and/or use as a pharmaceutical or agrochemical.

BACKGROUND OF THE INVENTION

Bio-discovery is a growing field, which investigates and screens for bioactive natural products from natural environments, including plants, microorganisms, coral and other marine life. In the search for bioactive natural products, biological material is screened for molecules having properties that may be of therapeutic benefit for potential use in a range of treatments, for example treatments for cancer, antiprotozoal treatments, antiparasitic treatments, antifungal treatments, antibiotic treatments and anti-inflammatory treatments, or for pesticidal activity.

SUMMARY OF THE INVENTION

The present invention arises from the discovery of new spiroketal derivatives which have potentially new therapeutic uses as cytotoxic agents, antiprotozoal agents, antiparasitic agents, antibiotic agents and anti-inflammatory or immunosuppressive agents, or potential as pesticidal agents for pharmaceutical or agricultural use.

One aspect of the invention provides compounds of the formula (I)

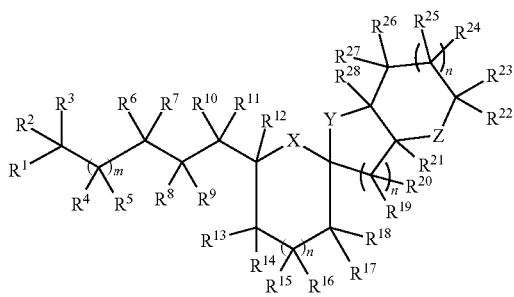

I wherein:

X, Y and Z are each independently selected from —S—, —O—, —NH—, —N($C_1$-$C_6$alkyl), and —C(R)$_2$;

n is 1 to 10;

m is 1 to 16;

$R^1$ to $R^{28}$ are each independently selected from hydrogen, —$C_1$-$C_{20}$ alkyl, —$C_2$-$C_{20}$ alkenyl, —$C_2$-$C_{20}$ alkynyl, —$C_3$-$C_8$ cycloalkyl, —$C_6$-$C_{14}$ aryl, —$C_5$-$C_{14}$ heteroaryl, —$C_3$-$C_{14}$ heterocyclyl, arylalkyl, heteroarylalkyl, heterocyclylalkyl, alkoxyalkyl, halo, —CN, —$NO_2$, —$C_1$-$C_{10}$ haloalkyl, —$C_1$-$C_{10}$ dihaloalkyl, —$C_1$-$C_{10}$ trihaloalkyl, —COR, —$CO_2$R, —OR, —SR, —N(R)$_2$, —NROR, —ON(R)$_2$, —SOR, —$SO_2$R, —$SO_3$R, —SON(R)$_2$, —$SO_2$N(R)$_2$, —$SO_3$N(R)$_2$, —P(R)$_3$, —P(O)(R)$_3$, —Si(R)$_3$, —B(R)$_2$, —C(W)R and —WC(W)R;

R is selected from hydrogen, —$C_1$-$C_{20}$ alkyl, —$C_2$-$C_{20}$ alkenyl, —$C_2$-$C_{20}$ alkenyl, —$C_3$-$C_8$ cycloalkyl, —$C_6$-$C_{14}$ aryl, —$C_5$-$C_{14}$ heteroaryl, —$C_3$-$C_{14}$ heterocyclyl, arylalkyl, heteroarylalkyl, heterocyclylalkyl, —$C_1$-$C_{10}$ haloalkyl, —$C_1$-$C_{10}$ dihaloalkyl and —$C_1$-$C_{10}$ trihaloalkyl; or one or more of $R^1$ (or $R^2$ or $R^3$) is connected to $R^4$ (or $R^5$), $R^4$ (or $R^5$) is connected to $R^6$ (or $R^7$), $R^6$ (or $R^7$) is connected to $R^8$ (or $R^9$), $R^8$ (or $R^9$) is connected to $R^{10}$ (or $R^{11}$), $R^{10}$ (or $R^{11}$) is connected to $R^{12}$, $R^{12}$ is connected to $R^{13}$ (or $R^{14}$), $R^{13}$ (or $R^{14}$) is connected to $R^5$ (or $R^{16}$), $R^{15}$ (or $R^{16}$) is connected to $R^{17}$ (or $R^{18}$), $R^{19}$ (or $R^{20}$) is connected to $R^{21}$, $R^{22}$ (or $R^{23}$) is connected to $R^{24}$ (or $R^{25}$), $R^{26}$ (or $R^{27}$) is connected to $R^{28}$ to form a $C_1$-$C_8$ disubstituted (fused) saturated or unsaturated carbo- and heterocyclic rings further substituted by R, —(C=W)R and —W(C=W)R;

one or more of $R^1$ (or $R^2$ or $R^3$) is connected to $R^4$ (or $R^5$), $R^4$ (or $R^5$) is connected to $R^6$ (or $R^7$), $R^6$ (or R) is connected to $R^8$ (or $R^9$), $R^8$ (or $R^9$) is connected to $R^{10}$ (or $R^{11}$), $R^{10}$ (or $R^{11}$) is connected to $R^{12}$, $R^{12}$ is connected to $R^{13}$ (or $R^{14}$), $R^{13}$ (or $R^{14}$) is connected to $R^{15}$ (or $R^{16}$), $R^{15}$ (or $R^{16}$) is connected to $R^{17}$ (or $R^{18}$), $R^{19}$ (or $R^{20}$) is connected to $R^{21}$, $R^{22}$ (or $R^{23}$) is connected to $R^{24}$ (or $R^{25}$), $R^{26}$ (or $R^{27}$) is connected to $R^{28}$ to form a double bond connection, an epoxides or a thioepoxide;

one or more of $R^1$ and $R^2$ (or $R^1$ and $R^3$) (or $R^2$ and $R^3$), $R^4$ and $R^5$, $R^6$ and $R^7$, $R^8$ and $R^9$, $R^{10}$ and $R^{11}$, $R^{13}$ and $R^{14}$, $R^{15}$ and $R^{16}$, $R^{17}$ and $R^{18}$, $R^{19}$ and $R^{20}$, $R^{22}$ and $R^{23}$, $R^{24}$ and $R^{25}$, $R^{24}$ (or $R^{25}$) is connected to $R^{26}$ (or $R^{27}$), $R^{26}$ and $R^{27}$ form a double bond to W, and W is selected from sulfur, oxygen, NH or N($C_1$-$C_6$alkyl);

one or more of $R^1$ and $R^2$ (or $R^3$) connected to $R^4$ and $R^5$, $R^4$ and $R^5$ connected to $R^6$ and $R^7$, $R^6$ and $R^7$ connected to $R^8$ and $R^9$, $R^8$ and $R^9$ connected to $R^{10}$ and $R^{11}$ to form a triple bond;

or a pharmaceutically, agriculturally or pesticidally acceptable salt thereof.

In some embodiments, where any one or more of $R^1$ to $R^{28}$ is $C_2$-$C_{20}$ alkenyl, one or more of $R^1$ to $R^{28}$ may further comprise an aryl or heteroaryl group.

In some embodiments, where any one or more of $R^1$ to $R^{28}$ is $C_2$-$C_{20}$ alkenyl the alkenyl units may be singular or multiple.

In yet other embodiments, where any one or more of $R^1$ to $R^{28}$ is $C_2$-$C_{20}$ alkynyl, one or more of $R^1$ to $R^{28}$ may further comprise an aryl or heteroaryl group.

In still yet other embodiments, where any one or of $R^1$ to $R^{28}$ is $C_2$-$C_{20}$ alkynyl the alkynyl units may be singular or multiple.

In one embodiment, the compound of formula (I) is a compound of formula (II):

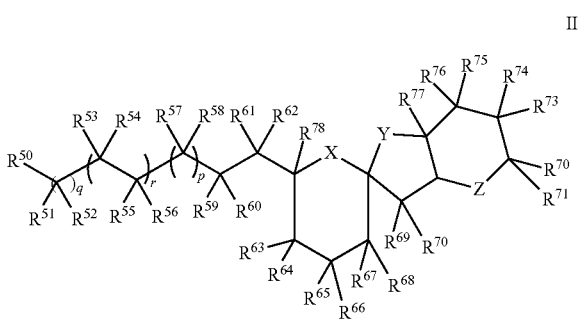

wherein

X, Y and Z are independently selected from —O—, —S—, —NH—, —N($C_1$-$C_6$ alkyl)- and —$CH_2$—;

$R^{50}$ is selected from —$CH_3$, —$C_3$-$C_8$ cycloalkyl, aryl, heterocyclyl and heteroaryl;

$R^{51}$, $R^{52}$, $R^{57}$, $R^{58}$, $R^{61}$, $R^{62}$, $R^{67}$, $R^{68}$, $R^{69}$ and $R^{70}$ are independently selected from hydrogen, —$C_1$-$C_{20}$ alkyl, —$C_2$-$C_{20}$ alkenyl, —$C_2$-$C_{20}$ alkynyl, —$C_3$-$C_8$ cycloalkyl, —$C_6$-$C_{14}$ aryl, —$C_5$-$C_{14}$ heteroaryl, —$C_3$-$C_{14}$ heterocyclyl, arylalkyl, heteroarylalkyl, heterocyclylalkyl, alkoxyalkyl, halo, —CN, —$NO_2$, —$C_1$-$C_{10}$ haloalkyl, —$C_1$-$C_{10}$ dihaloalkyl, —$C_1$-$C_{10}$ trihaloalkyl, —COR, —$CO_2$R, —OR, —SR, —N(R)$_2$, —NROR, —ON(R)$_2$, —SOR, —$SO_2$R, —$SO_3$R, —SON(R)$_2$, —$SO_2$N(R)$_2$, —$SO_3$N(R)$_2$, —P(R)$_3$, —P(O)(R)$_3$, —OSi(R)$_3$, —OB(R)$_2$, —C(W)R and —WC(W)R;

$R^{53}$ to $R^{56}$ are independently selected from hydrogen, —$C_1$-$C_{20}$ alkyl, —$C_2$-$C_{20}$ alkenyl, —$C_2$-$C_{20}$ alkynyl, —$C_3$-$C_8$ cycloalkyl, —$C_6$-$C_{14}$ aryl, —$C_5$-$C_{14}$ heteroaryl, —$C_3$-$C_{14}$ heterocyclyl, arylalkyl, heteroarylalkyl, heterocyclylalkyl, alkoxyalkyl, halo, —CN, —$NO_2$, —$C_1$-$C_{10}$ haloalkyl, —$C_1$-$C_{10}$ dihaloalkyl, —$C_1$-$C_{10}$ trihaloalkyl, —COR, —$CO_2$R, —OR, —SR, —N(R)$_2$, —NROR, —ON(R)$_2$, —SOR, —$SO_2$R, —$SO_3$R, —SON(R)$_2$, —$SO_2$N(R)$_2$, —$SO_3$N(R)$_2$, —P(R)$_3$, —P(O)(R)$_3$, —OSi(R)$_3$, —OB(R)$_2$, —C(W)R and —WC(W)R; or $R^{54}$ and $R^{55}$ taken together form a double bond or are —O—; or $R^{53}$ and $R^{54}$ or $R^{55}$ and $R^{56}$ taken together form a carbonyl group;

$R^{59}$ and $R^{60}$ are independently selected from hydrogen, —$C_1$-$C_{20}$ alkyl, —$C_2$-$C_{20}$ alkenyl, —$C_2$-$C_{20}$ alkynyl, —$C_3$-$C_8$ cycloalkyl, —$C_6$-$C_{14}$ aryl, —$C_5$-$C_{14}$ heteroaryl, —$C_3$-$C_{14}$ heterocyclyl, arylalkyl, heteroarylalkyl, heterocyclylalkyl, alkoxyalkyl, halo, —CN, —$NO_2$, —$C_1$-$C_{10}$ haloalkyl, —$C_1$-$C_{10}$ dihaloalkyl, —$C_1$-$C_{10}$ trihaloalkyl, —COR, —$CO_2$R, —OR, —SR, —N(R)$_2$, —NROR, —ON(R)$_2$, —SOR, —$SO_2$R, —$SO_3$R, —SON(R)$_2$, —$SO_2$N(R)$_2$, —$SO_3$N(R)$_2$, —P(R)$_3$, —P(O)(R)$_3$, —OSi(R)$_3$, —OB(R)$_2$, —C(W)R and —WC(W)R; or $R^{59}$ and $R^{60}$ taken together form a carbonyl group;

$R^{63}$ to $R^{66}$ are independently selected from hydrogen, —$C_1$-$C_{20}$ alkyl, —$C_2$-$C_{20}$ alkenyl, —$C_2$-$C_{20}$ alkynyl, —$C_3$-$C_8$ cycloalkyl, —$C_6$-$C_{14}$ aryl, —$C_5$-$C_{14}$ heteroaryl, —$C_3$-$C_{14}$ heterocyclyl, arylalkyl, heteroarylalkyl, heterocyclylalkyl, alkoxyalkyl, halo, —CN, —$NO_2$, —$C_1$-$C_{10}$ haloalkyl, —$C_1$-$C_{10}$ dihaloalkyl, —$C_1$-$C_{10}$ trihaloalkyl, —COR, —$CO_2$R, —OR, —SR, —N(R)$_2$, —NROR, —ON(R)$_2$, —SOR, —$SO_2$R, —$SO_3$R, —SON(R)$_2$, —$SO_2$N(R)$_2$, —$SO_3$N(R)$_2$, —P(R)$_3$, —P(O)(R)$_3$, —OSi(R)$_3$, —OB(R)$_2$, —C(W)R and —WC(W)R; or $R^{64}$ and $R^{65}$ taken together form a double bond or are —O—; or $R^{63}$ and $R^{64}$ or $R^{65}$ and $R^{66}$ taken together form a carbonyl group;

$R^{71}$ and $R^{72}$ are independently selected from hydrogen, —$C_1$-$C_{20}$ alkyl, —$C_2$-$C_{20}$ alkenyl, —$C_2$-$C_{20}$ alkynyl, —$C_3$-$C_8$ cycloalkyl, —$C_6$-$C_{14}$ aryl, —$C_5$-$C_{14}$ heteroaryl, —$C_3$-$C_{14}$ heterocyclyl, arylalkyl, heteroarylalkyl, heterocyclylalkyl, alkoxyalkyl, halo, —CN, —$NO_2$, —$C_1$-$C_{10}$ haloalkyl, —$C_1$-$C_{10}$ dihaloalkyl, —$C_1$-$C_{10}$ trihaloalkyl, —COR, —$CO_2$R, —OR, —SR, —N(R)$_2$, —NROR, —ON(R)$_2$, —SOR, —$SO_2$R, —$SO_3$R, —SON(R)$_2$, —$SO_2$N(R)$_2$, —$SO_3$N(R)$_2$, —P(R)$_3$, —P(O)(R)$_3$, —OSi(R)$_3$, —OB(R)$_2$, —C(W)R and —WC(W)R; or $R^{71}$ and $R^{72}$ taken together form a carbonyl group;

$R^{73}$ to $R^{76}$ are independently selected from hydrogen, —$C_1$-$C_{20}$ alkyl, —$C_2$-$C_{20}$ alkenyl, —$C_2$-$C_{20}$ alkynyl, —$C_3$-$C_8$ cycloalkyl, —$C_6$-$C_{14}$ aryl, —$C_5$-$C_{14}$ heteroaryl, —$C_3$-$C_{14}$ heterocyclyl, arylalkyl, heteroarylalkyl, heterocyclylalkyl, alkoxyalkyl, halo, —CN, —$NO_2$, —$C_1$-$C_{10}$ haloalkyl, —$C_1$-$C_{10}$ dihaloalkyl, —$C_1$-$C_{10}$ trihaloalkyl, —COR, —$CO_2$R, —OR, —SR, —N(R)$_2$, —NROR, —ON(R)$_2$, —SOR, —$SO_2$R, —$SO_3$R, —SON(R)$_2$, —$SO_2$N(R)$_2$, —$SO_3$N(R)$_2$, —P(R)$_3$, —P(O)(R)$_3$, —OSi(R)$_3$, —OB(R)$_2$, —C(W)R and —WC(W)R; or $R^{74}$ and $R^{75}$ taken together form a double bond or are —O—; or $R^{73}$ and $R^{74}$ or $R^{75}$ and $R^{76}$ taken together form a carbonyl group;

$R^{77}$ and $R^{78}$ are independently selected from hydrogen, —$C_1$-$C_{10}$ alkyl, —$C_2$-$C_{10}$ alkenyl and —$C_2$-$C_{10}$ alkynyl;

W is selected from —O—, —S—, —NH— and —N($C_1$-$C_6$ alkyl)-;

R is selected from hydrogen, —$C_1$-$C_{20}$ alkyl, —$C_2$-$C_{20}$ alkenyl, —$C_2$-$C_{20}$ alkynyl, —$C_3$-$C_8$ cycloalkyl, —$C_6$-$C_{14}$ aryl, —$C_5$-$C_{14}$ heteroaryl, —$C_3$-$C_{14}$ heterocyclyl, arylalkyl, heteroarylalkyl, heterocyclylalkyl, —$C_1$-$C_{10}$ haloalkyl, —$C_1$-$C_{10}$ dihaloalkyl and —$C_1$-$C_{10}$ trihaloalkyl;

p and q are independently 0 or 1; and r is an integer from 1 to 8;

wherein each alkyl, alkenyl, alkynyl, cycloalkyl, aryl, heterocyclyl and heteroaryl is optionally substituted;

or a pharmaceutically, agriculturally or pesticidally acceptable salt thereof. In some embodiments of formula II, X, Y and Z are independently selected from —O— and —S—;

$R^{50}$ is selected from —$CH_3$, —$C_3$-$C_8$ cycloalkyl, aryl, heterocyclyl and heteroaryl;

$R^{51}$, $R^{52}$, $R^{57}$, $R^{58}$, $R^{61}$, $R^{62}$, $R^{67}$, $R^{68}$, $R^{69}$ and $R^{70}$ are independently selected from hydrogen, —$C_1$-$C_{20}$ alkyl, —$C_2$-$C_{20}$ alkenyl, —$C_2$-$C_{20}$ alkynyl, —$C_3$-$C_8$ cycloalkyl, —$C_6$-$C_{14}$ aryl, —$C_5$-$C_{14}$ heteroaryl, —$C_3$-$C_{14}$ heterocyclyl, arylalkyl, heteroarylalkyl, heterocyclylalkyl, alkoxyalkyl, halo, —CN, —$NO_2$, —$C_1$-$C_{10}$ haloalkyl, —$C_1$-$C_{10}$ dihaloalkyl, —$C_1$-$C_{10}$ trihaloalkyl, —COR, —$CO_2$R, —OR, —SR, —N(R)$_2$, —NROR, —ON(R)$_2$, —SOR, —$SO_2$R, —$SO_3$R, —SON(R)$_2$, —$SO_2$N(R)$_2$, —$SO_3$N(R)$_2$, —P(R)$_3$, —P(O)(R)$_3$, —OSi(R)$_3$, —OB(R)$_2$, —C(W)R and —WC(W)R;

$R^{53}$ to $R^{56}$ are independently selected from hydrogen, —$C_1$-$C_{20}$ alkyl, —$C_2$-$C_{20}$ alkenyl, —$C_2$-$C_{20}$ alkynyl, —$C_3$-$C_8$ cycloalkyl, —$C_6$-$C_{14}$ aryl, —$C_5$-$C_{14}$ heteroaryl, —$C_3$-$C_{14}$ heterocyclyl, arylalkyl, heteroarylalkyl, heterocyclylalkyl, alkoxyalkyl, halo, —CN, —$NO_2$, —$C_1$-$C_{10}$ haloalkyl, —$C_1$-$C_{10}$ dihaloalkyl, —$C_1$-$C_{10}$ trihaloalkyl, —COR, —$CO_2$R, —OR, —SR, —N(R)$_2$, —NROR, —ON(R)$_2$, —SOR, —$SO_2$R, —$SO_3$R, —SON(R)$_2$, —$SO_2$N(R)$_2$, —$SO_3$N(R)$_2$, —P(R)$_3$, —P(O)(R)$_3$, —OSi(R)$_3$, —OB(R)$_2$, —C(W)R and —WC(W)R; or $R^{54}$ and $R^{55}$ taken together form a double bond or —O—;

$R^{59}$ is hydrogen and $R^{60}$ is selected from —OH, —O$C_1$-$C_{10}$ alkyl, —O$C_2$-$C_{10}$ alkenyl, —Ocycloalkyl, —Oaryl, —Oheterocyclyl, —Oheteroaryl, —O$C_1$-$C_{10}$ alkylcycloalkyl, —O$C_1$-$C_{10}$ alkylaryl, —O$C_1$-$C_{10}$ alkylheterocyclyl, —O$C_1$-$C_{10}$ alkylheteroaryl and —OC(O)R; or $R^{59}$ and $R^{60}$ taken together form a carbonyl group;

$R^{63}$ and $R^{64}$ are independently selected from hydrogen, —$C_1$-$C_{20}$ alkyl, —$C_2$-$C_{20}$ alkenyl, —$C_2$-$C_{20}$ alkynyl, —$C_3$-$C_8$ cycloalkyl, —$C_6$-$C_{14}$ aryl, —$C_5$-$C_{14}$ heteroaryl, —$C_3$-$C_{14}$ heterocyclyl, arylalkyl, heteroarylalkyl, heterocyclylalkyl, alkoxyalkyl, halo, —CN, —$NO_2$, —$C_1$-$C_{10}$ haloalkyl, —$C_1$-$C_{10}$ dihaloalkyl, —$C_1$-$C_{10}$ trihaloalkyl, —COR, —$CO_2R$, —OR, —SR, —$N(R)_2$, —NROR, —$ON(R)_2$, —SOR, —$SO_2R$, —$SO_3R$, —$SON(R)_2$, —$SO_2N(R)_2$, —$SO_3N(R)_2$, —$P(R)_3$, —$P(O)(R)_3$, —$OSi(R)_3$, —$OB(R)_2$, —C(W)R and —WC(W)R;

$R^{65}$ is hydrogen and $R^{66}$ is selected from —OH, —$OC_1$-$C_{10}$ alkyl, —$OC_2$-$C_{10}$ alkenyl, —Ocycloalkyl, —Oaryl, —Oheterocyclyl, —Oheteroaryl, —$OC_1$-$C_{10}$ alkylcycloalkyl, —$OC_1$-$C_{10}$ alkylaryl, —$OC_1$-$C_{10}$ alkylheterocyclyl, —$OC_1$-$C_{10}$ alkylheteroaryl and —OC(O)R; or $R^{65}$ and $R^{66}$ taken together form a carbonyl group; or $R^{64}$ and $R^{65}$ taken together form a double bond;

$R^{71}$ is hydrogen and $R^{72}$ is selected from —OH, —$OC_1$-$C_{10}$ alkyl, —$OC_2$-$C_{10}$ alkenyl, —Ocycloalkyl, —Oaryl, —Oheterocyclyl, —Oheteroaryl, —$OC_1$-$C_{10}$ alkylcycloalkyl, —$OC_1$-$C_{10}$ alkylaryl, —$OC_1$-$C_{10}$ alkylheterocyclyl, —$OC_1$-$C_{10}$ alkylheteroaryl and —OC(O)R; or $R^{71}$ and $R^{72}$ taken together form a carbonyl group;

$R^{73}$ to $R^{76}$ are independently selected from hydrogen, —$C_1$-$C_{20}$ alkyl, —$C_2$-$C_{20}$ alkenyl, —$C_2$-$C_{20}$ alkynyl, —$C_3$-$C_8$ cycloalkyl, —$C_6$-$C_{14}$ aryl, —$C_5$-$C_{14}$ heteroaryl, —$C_3$-$C_{14}$ heterocyclyl, arylalkyl, heteroarylalkyl, heterocyclylalkyl, alkoxyalkyl, halo, —CN, —$NO_2$, —$C_1$-$C_{10}$ haloalkyl, —$C_1$-$C_{10}$ dihaloalkyl, —$C_1$-$C_{10}$ trihaloalkyl, —COR, —$CO_2R$, —OR, —SR, —$N(R)_2$, —NROR, —$ON(R)_2$, —SOR, —$SO_2R$, —$SO_3R$, —$SON(R)_2$, —$SO_2N(R)_2$, —$SO_3N(R)_2$, —$P(R)_3$, —$P(O)(R)_3$, —$OSi(R)_3$, —$OB(R)_2$, —C(W)R and —WC(W)R; or $R^{74}$ and $R^{75}$ taken together form a double bond or —O—;

$R^{77}$ and $R^{78}$ are independently selected from hydrogen and —$C_1$-$C_{10}$ alkyl;

W is selected from —O—, —S—, —NH— and —N($C_1$-$C_6$ alkyl)-;

R is selected from hydrogen, —$C_1$-$C_{20}$ alkyl, —$C_2$-$C_{20}$ alkenyl, —$C_2$-$C_{20}$ alkenyl, —$C_3$-$C_8$ cycloalkyl, —$C_6$-$C_{14}$ aryl, —$C_5$-$C_{14}$ heteroaryl, —$C_3$-$C_{14}$ heterocyclyl, arylalkyl, heteroarylalkyl, heterocyclylalkyl, —$C_1$-$C_{10}$ haloalkyl, —$C_1$-$C_{10}$ dihaloalkyl and —$C_1$-$C_{10}$ trihaloalkyl;

p and q are 0 or 1; and r is an integer from 1 to 8;

wherein each alkyl, alkenyl, alkynyl, cycloalkyl, aryl, heterocyclyl and heteroaryl is optionally substituted;

or a pharmaceutically, agriculturally or pesticidally acceptable salt thereof.

In some embodiments the compound of formula I is a compound of formula III:

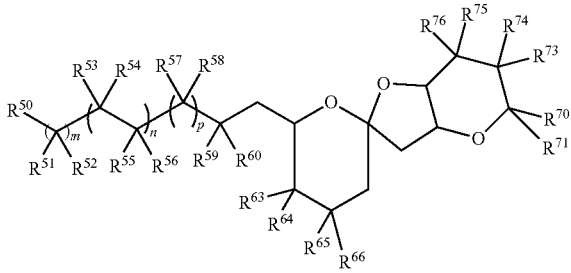

III wherein:

$R^{50}$ is selected from —$CH_3$, —$C_3$-$C_8$ cycloalkyl, aryl, heterocyclyl and heteroaryl;

$R^{51}$, $R^{52}$, $R^{57}$ and $R^{58}$ are independently selected from hydrogen, —$C_1$-$C_{20}$ alkyl, —$C_2$-$C_{20}$ alkenyl, —$C_2$-$C_{20}$ alkynyl, —$C_3$-$C_8$ cycloalkyl, —$C_6$-$C_{14}$ aryl, —$C_5$-$C_{14}$ heteroaryl, —$C_3$-$C_{14}$ heterocyclyl, arylalkyl, heteroarylalkyl, heterocyclylalkyl, alkoxyalkyl, halo, —CN, —$NO_2$, —$C_1$-$C_{10}$ haloalkyl, —$C_1$-$C_{10}$ dihaloalkyl, —$C_1$-$C_{10}$ trihaloalkyl, —COR, —$CO_2R$, —OR, —SR, —$N(R)_2$, —NROR, —$ON(R)_2$, —SOR, —$SO_2R$, —$SO_3R$, —$SON(R)_2$, —$SO_2N(R)_2$, —$SO_3N(R)_2$, —$P(R)_3$, —$P(O)(R)_3$, —$OSi(R)_3$, —$OB(R)_2$, —C(O)R and —OC(O)R;

$R^{53}$ to $R^{56}$ are independently selected from hydrogen, —$C_1$-$C_{20}$ alkyl, —$C_2$-$C_{20}$ alkenyl, —$C_2$-$C_{20}$ alkynyl, —$C_3$-$C_8$ cycloalkyl, —$C_6$-$C_{14}$ aryl, —$C_5$-$C_{14}$ heteroaryl, —$C_3$-$C_{14}$ heterocyclyl, arylalkyl, heteroarylalkyl, heterocyclylalkyl, alkoxyalkyl, halo, —CN, —$NO_2$, —$C_1$-$C_{10}$ haloalkyl, —$C_1$-$C_{10}$ dihaloalkyl, —$C_1$-$C_{10}$ trihaloalkyl, —COR, —$CO_2R$, —OR, —SR, —$N(R)_2$, —NROR, —$ON(R)_2$, —SOR, —$SO_2R$, —$SO_3R$, —$SON(R)_2$, —$SO_2N(R)_2$, —$SO_3N(R)_2$, —$P(R)_3$, —$P(O)(R)_3$, —$OSi(R)_3$, —$OB(R)_2$, —C(O)R and —OC(O)R; or $R^{54}$ and $R^{55}$ taken together form a double bond or —O—;

$R^{59}$ is hydrogen and $R^{60}$ is selected from —OH, —$OC_1$-$C_{10}$ alkyl, —$OC_2$-$C_{10}$ alkenyl, —Ocycloalkyl, —Oaryl, —Oheterocyclyl, —Oheteroaryl, —$OC_1$-$C_{10}$ alkylcycloalkyl, —$OC_1$-$C_{10}$ alkylaryl, —$OC_1$-$C_{10}$ alkylheterocyclyl, —$OC_1$-$C_{10}$ alkylheteroaryl and —OC(O)R; or $R^{59}$ and $R^{60}$ taken together form a carbonyl group;

$R^{63}$ and $R^{64}$ hydrogen;

$R^{65}$ is hydrogen and $R^{66}$ is selected from —OH, —$OC_1$-$C_{10}$ alkyl, —$OC_2$-$C_{10}$ alkenyl, —Ocycloalkyl, —Oaryl, —Oheterocyclyl, —Oheteroaryl, —$OC_1$-$C_{10}$ alkylcycloalkyl, —$OC_1$-$C_{10}$ alkylaryl, —$OC_1$-$C_{10}$ alkylheterocyclyl, —$OC_1$-$C_{10}$ alkylheteroaryl and —OC(O)R; or $R^{65}$ and $R^{66}$ taken together form a carbonyl group; or $R^{64}$ and $R^{65}$ taken together form a double bond;

$R^{71}$ is hydrogen and $R^{72}$ is selected from —OH, —$OC_1$-$C_{10}$ alkyl, —$OC_2$-$C_{10}$ alkenyl, —Ocycloalkyl, —Oaryl, —Oheterocyclyl, —Oheteroaryl, —$OC_1$-$C_{10}$ alkylcycloalkyl, —$OC_1$-$C_{10}$ alkylaryl, —$OC_1$-$C_{10}$ alkylheterocyclyl, —$OC_1$-$C_{10}$ alkylheteroaryl and —OC(O)R; or $R^{71}$ and $R^{72}$ taken together form a carbonyl group;

$R^{73}$ to $R^{76}$ are independently selected from hydrogen, —$C_1$-$C_{20}$ alkyl, —$C_2$-$C_{20}$ alkenyl, —$C_2$-$C_{20}$ alkynyl, —$C_3$-$C_8$ cycloalkyl, —$C_6$-$C_{14}$ aryl, —$C_5$-$C_{14}$ heteroaryl, —$C_3$-$C_{14}$ heterocyclyl, arylalkyl, heteroarylalkyl, heterocyclylalkyl, alkoxyalkyl, halo, —CN, —$NO_2$, —$C_1$-$C_{10}$ haloalkyl, —$C_1$-$C_{10}$ dihaloalkyl, —$C_1$-$C_{10}$ trihaloalkyl, —COR, —$CO_2R$, —OR, —SR, —$N(R)_2$, —NROR, —$ON(R)_2$, —SOR, —$SO_2R$, —$SO_3R$, —$SON(R)_2$, —$SO_2N(R)_2$, —$SO_3N(R)_2$, —$P(R)_3$, —$P(O)(R)_3$, —$OSi(R)_3$, —$OB(R)_2$, —C(W)R and —WC(W)R; or $R^{74}$ and $R^{75}$ taken together form a double bond or —O—;

R is selected from hydrogen, —$C_1$-$C_{20}$ alkyl, —$C_2$-$C_{20}$ alkenyl, —$C_3$-$C_8$ cycloalkyl, —$C_6$-$C_{14}$ aryl, —$C_5$-$C_{14}$ heteroaryl, —$C_3$-$C_{14}$ heterocyclyl, arylalkyl, heteroarylalkyl, heterocyclylalkyl, —$C_1$-$C_{10}$ haloalkyl, —$C_1$-$C_{10}$ dihaloalkyl and —$C_1$-$C_{10}$ trihaloalkyl;

p and q are 0 or 1; and r is an integer from 1 to 8;

wherein each alkyl, alkenyl, alkynyl, cycloalkyl, aryl, heterocyclyl and heteroaryl is optionally substituted;

or a pharmaceutically, agriculturally or pesticidally acceptable salt thereof.

In preferred embodiments of the compounds of formula II, one or more of the following applies:

X, Y and Z are independently oxygen or sulphur; especially oxygen;

$R^{50}$ is —$CH_3$, aryl, heterocyclyl or heteroaryl, especially —$CH_3$, phenyl or heteroaryl, more especially —$CH_3$, phenyl or benzodioxolane;

$R^{51}$, $R^{52}$, $R^{57}$ and $R^{58}$ are independently selected from hydrogen, —$C_1$-$C_6$ alkyl, —$C_2$-$C_6$ alkenyl, —$C_2$-$C_6$ alkynyl, —$C_3$-$C_8$ cycloalkyl, —$C_6$-$C_{14}$ aryl, —$C_5$-$C_{14}$ heteroaryl, —$C_3$-$C_{14}$ heterocyclyl, halo, —CN, —$NO_2$, —$C_1$-$C_6$ haloalkyl, —$C_1$-$C_6$ dihaloalkyl, —$C_1$-$C_6$ trihaloalkyl, —$COC_1$-$C_6$ alkyl, —$CO_2H$, $CO_2C_1$-$C_6$ alkyl, —OH, —$OC_1$-$C_6$ alkyl, —SH, —$SC_1$-$C_6$ alkyl, —$NH_2$, —$NHC_1$-$C_6$ alkyl, —$N(C_1$-$C_6$ alkyl$)_2$ and —$OC(O)C_1$-$C_6$ alkyl; especially; hydrogen, $C_1$-$C_6$ alkyl, —$COC_1$-$C_6$ alkyl, —$CO_2H$, $CO_2C_1$-$C_6$ alkyl, —OH, —$OC_1$-$C_6$ alkyl and —$OC(O)C_1$-$C_6$ alkyl; especially hydrogen;

$R^{53}$ to $R^{56}$ are independently selected from hydrogen, —$C_1$-$C_6$ alkyl, —$C_2$-$C_6$ alkenyl, —$C_2$-$C_6$ alkynyl, —$C_3$-$C_8$ cycloalkyl, —$C_6$-$C_{14}$ aryl, —$C_5$-$C_{14}$ heteroaryl, —$C_3$-$C_{14}$ heterocyclyl, halo, —CN, —$NO_2$, —$C_1$-$C_6$ haloalkyl, —$C_1$-$C_6$ dihaloalkyl, —$C_1$-$C_6$ trihaloalkyl, —$COC_1$-$C_6$ alkyl, —$CO_2H$, $CO_2C_1$-$C_6$ alkyl, —OH, —$OC_1$-$C_6$ alkyl, —SH, —$SC_1$-$C_6$ alkyl, —$NH_2$, —$NHC_1$-$C_6$ alkyl, —$N(C_1$-$C_6$ alkyl$)_2$ and —$OC(O)C_1$-$C_6$ alkyl or $R^{54}$ and $R^{55}$ taken together form a double bond or —O—; especially; hydrogen, $C_1$-$C_6$ alkyl, —$COC_1$-$C_6$ alkyl, —$CO_2H$, $CO_2$ $C_1$-$C_6$ alkyl, —OH, —$OC_1$-$C_6$ alkyl and —$OC(O)C_1$-$C_6$ alkyl or $R^{54}$ and $R^{55}$ taken together form a double bond or —O—; especially hydrogen or $R^{54}$ and $R^{55}$ taken together form a double bond or —O—;

$R^{59}$ is hydrogen and $R^{60}$ is selected from —OH, —$OC_1$-$C_{10}$ alkyl, —$OC_2$-$C_{10}$ alkenyl, —Ocycloalkyl, —Oaryl, —Oheterocyclyl, —Oheteroaryl, —$OC_1$-$C_{10}$ alkylcycloalkyl, —$OC_1$-$C_{10}$ alkylaryl, —$OC_1$-$C_{10}$ alkylheterocyclyl, —$OC_1$-$C_{10}$ alkylheteroaryl and —OC(O)R; or $R^{59}$ and $R^{60}$ taken together form a carbonyl group; especially where $R^{60}$ is —OH, —$OC_1$-$C_{10}$ alkyl and —$OC(O)C_1$-$C_{10}$ alkyl; or $R^{59}$ and $R^{60}$ taken together form a carbonyl group;

$R^{61}$, $R^{62}$, $R^{67}$, $R^{68}$, $R^{69}$ and $R^{70}$ are independently selected from hydrogen, —$C_1$-$C_6$ alkyl, —$C_2$-$C_6$ alkenyl, —$C_2$-$C_6$ alkynyl, —$C_3$-$C_8$ cycloalkyl, —$C_6$-$C_{14}$ aryl, —$C_5$-$C_{14}$ heteroaryl, —$C_3$-$C_{14}$ heterocyclyl, halo, —CN, —$NO_2$, —$C_1$-$C_6$ haloalkyl, —$C_1$-$C_6$ dihaloalkyl, —$C_1$-$C_6$ trihaloalkyl, —$COC_1$-$C_6$ alkyl, —$CO_2H$, $CO_2C_1$-$C_6$ alkyl, —OH, —$OC_1$-$C_6$ alkyl, —SH, —$SC_1$-$C_6$ alkyl, —$NH_2$, —$NHC_1$-$C_6$ alkyl, $N(C_1$-$C_6$ alkyl$)_2$ and —$OC(O)C_1$-$C_6$ alkyl; especially hydrogen, —$C_1$-$C_3$ alkyl, —OH, —$OC_1$-$C_6$ alkyl and —$OC(O)C_1$-$C_6$ alkyl; more especially hydrogen;

$R^{63}$ and $R^{64}$ are independently selected from hydrogen, —$C_1$-$C_6$ alkyl, —$C_2$-$C_6$ alkenyl, —$C_2$-$C_6$ alkynyl, —$C_3$-$C_8$ cycloalkyl, —$C_6$-$C_{14}$ aryl, —$C_5$-$C_{14}$ heteroaryl, —$C_3$-$C_{14}$ heterocyclyl, halo, —CN, —$NO_2$, —$C_1$-$C_6$ haloalkyl, —$C_1$-$C_6$ dihaloalkyl, —$C_1$-$C_6$ trihaloalkyl, —$COC_1$-$C_6$ alkyl, —$CO_2H$, $CO_2C_1$-$C_6$ alkyl, —OH, —$OC_1$-$C_6$ alkyl, —SH, —$SC_1$-$C_6$ alkyl, —$NH_2$, —$NHC_1$-$C_6$ alkyl, $N(C_1$-$C_6$ alkyl$)_2$ and —$OC(O)C_1$-$C_6$ alkyl; especially hydrogen, —$C_1$-$C_3$ alkyl, —OH, —$OC_1$-$C_6$ alkyl and —$OC(O)C_1$-$C_6$ alkyl; more especially hydrogen;

$R^{65}$ is hydrogen and $R^{66}$ is selected from —OH, —$OC_1$-$C_{10}$ alkyl, —$OC_2$-$C_{10}$ alkenyl, —Ocycloalkyl, —Oaryl, —Oheterocyclyl, —Oheteroaryl, —$OC_1$-$C_{10}$ alkylcycloalkyl, —$OC_1$-$C_{10}$ alkylaryl, —$OC_1$-$C_{10}$ alkylheterocyclyl, —$OC_1$-$C_{10}$ alkylheteroaryl and —OC(O)R; or $R^{59}$ and $R^{60}$ taken together form a carbonyl group; especially where $R^{60}$ is —OH, —$OC_1$-$C_{10}$ alkyl and —$OC(O)C_1$-$C_{10}$ alkyl; or $R^{59}$ and $R^{60}$ taken together form a carbonyl group;

or where $R^{64}$ and $R^{65}$ form a double bond or —O—; especially a double bond;

$R^{71}$ is hydrogen and $R^{72}$ is selected from —OH, —$OC_1$-$C_{10}$ alkyl, —$OC_2$-$C_{10}$ alkenyl, —Ocycloalkyl, —Oaryl, —Oheterocyclyl, —Oheteroaryl, —$OC_1$-$C_{10}$ alkylcycloalkyl, —$OC_1$-$C_{10}$ alkylaryl, —$OC_1$-$C_{10}$ alkylheterocyclyl, —$OC_1$-$C_{10}$ alkylheteroaryl and —OC(O)R; or $R^{71}$ and $R^{72}$ taken together form a carbonyl group; especially where $R^{72}$ is —OH, —$OC_1$-$C_{10}$ alkyl and —$OC(O)C_1$-$C_{10}$ alkyl; or $R^{71}$ and $R^{72}$ taken together form a carbonyl group;

$R^{73}$, $R^{74}$, $R^{75}$ and $R^{76}$ are independently selected from hydrogen, —$C_1$-$C_6$ alkyl, —$C_2$-$C_6$ alkenyl, —$C_2$-$C_6$ alkynyl, —$C_3$-$C_8$ cycloalkyl, —$C_6$-$C_{14}$ aryl, —$C_5$-$C_{14}$ heteroaryl, —$C_3$-$C_{14}$ heterocyclyl, halo, —CN, —$NO_2$, —$C_1$-$C_6$ haloalkyl, —$C_1$-$C_6$ dihaloalkyl, —$C_1$-$C_6$ trihaloalkyl, —$COC_1$-$C_6$ alkyl, —$CO_2H$, $CO_2C_1$-$C_6$ alkyl, —OH, —$OC_1$-$C_6$ alkyl, —SH, —$SC_1$-$C_6$ alkyl, —$NH_2$, —$NHC_1$-$C_6$ alkyl, $N(C_1$-$C_6$ alkyl$)_2$ and —$OC(O)C_1$-$C_6$ alkyl or $R^{74}$ and $R^{75}$ taken together form a double bond or —O—; especially hydrogen, —$C_1$-$C_3$ alkyl, —OH, —$OC_1$-$C_6$ alkyl and —$OC(O)C_1$-$C_6$ alkyl or $R^{74}$ and $R^{75}$ taken together form a double bond or —O—; more especially hydrogen or $R^{74}$ and $R^{75}$ taken together form a double bond or —O—;

$R^{77}$ and $R^{78}$ are independently selected from hydrogen and —$C_1$-$C_3$ alkyl; especially hydrogen and methyl, more especially hydrogen;

r is an integer from 3 to 7.

In some embodiments the compound of the invention is selected from: is

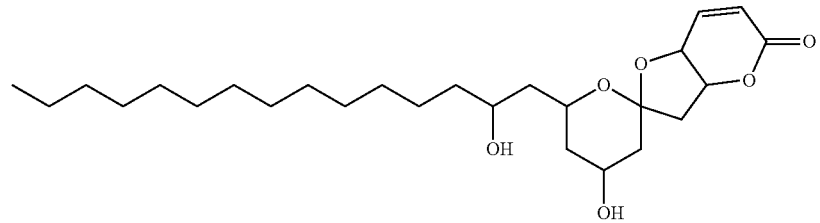 [SMILES: CCCCCCCCCCCCCC(O)CC1CC(O)CC2(CC3OC(=O)C=CC3O2)O1]

also referred to as EBI-23;

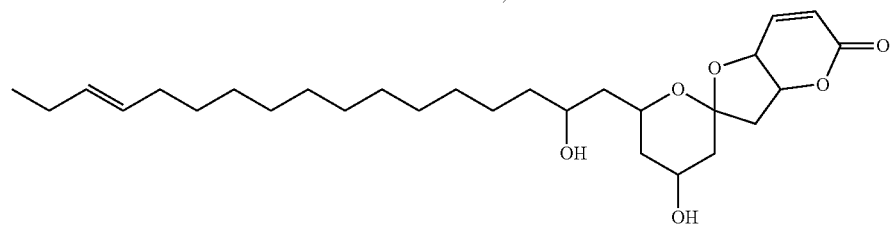

also referred to as EBI-24;

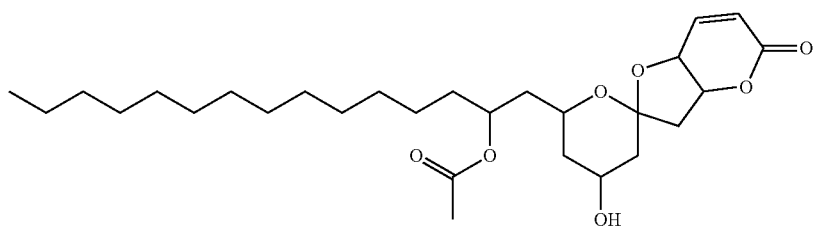
also referred to as EBI-25;
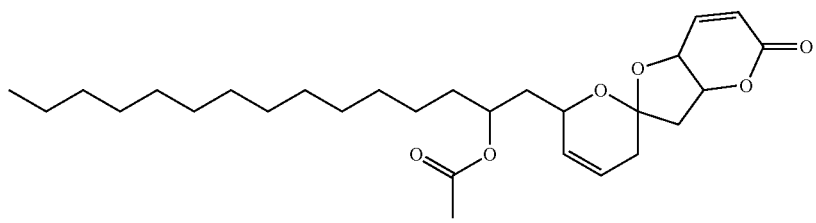
also referred to as EBI-42;
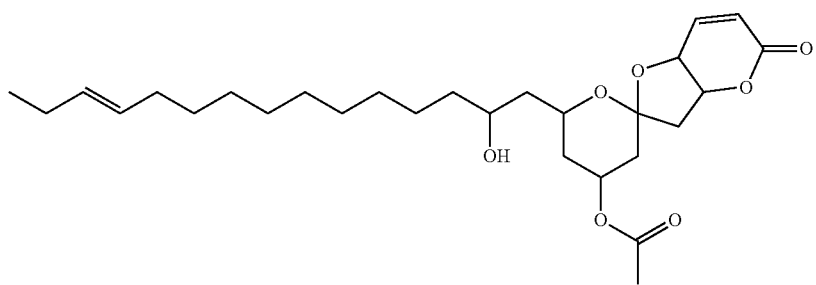
or
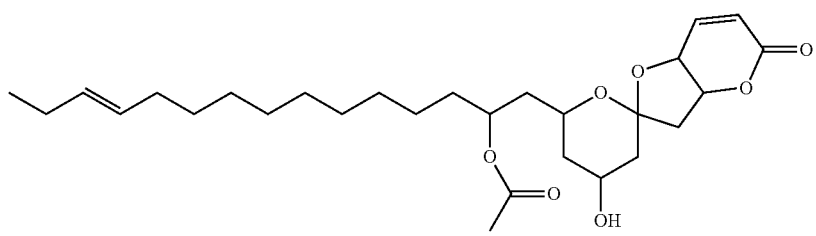
also referred to herein as EBI-72;
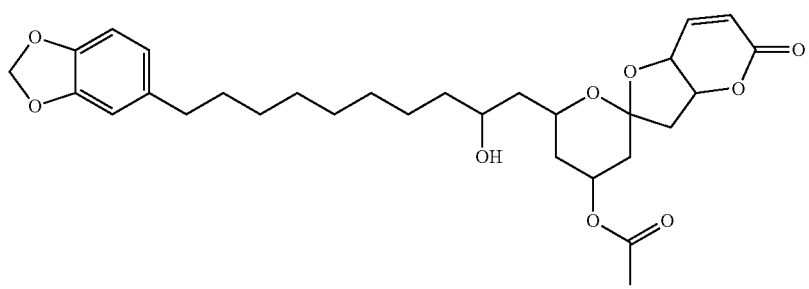
or
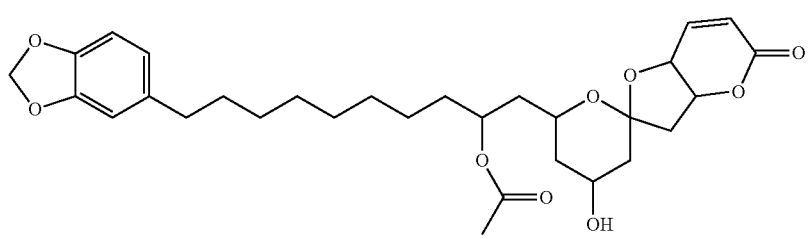
also referred to herein as EBI-73;
Other compounds of the invention include:

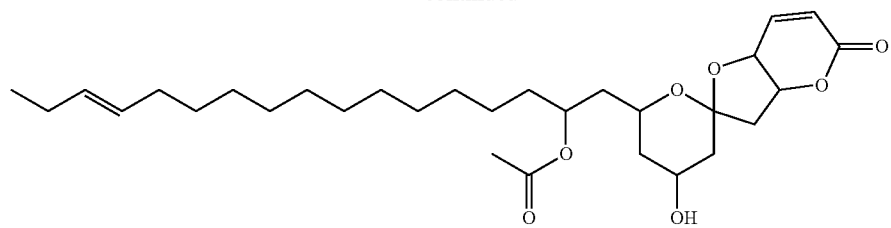
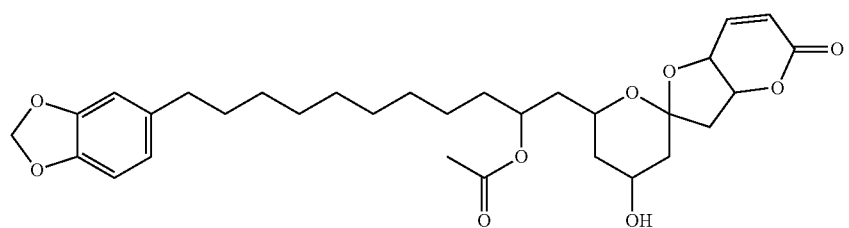
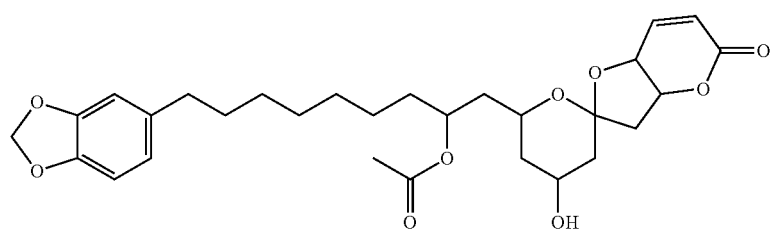
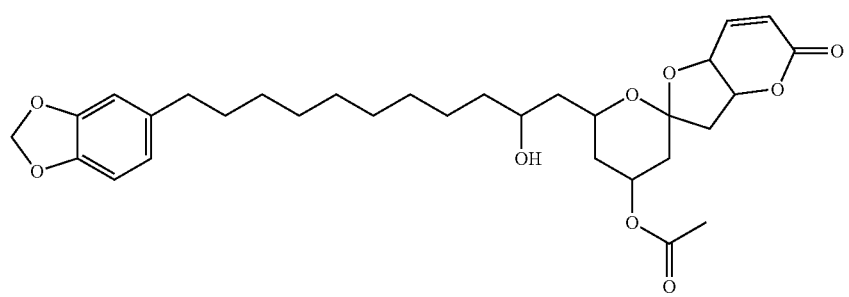
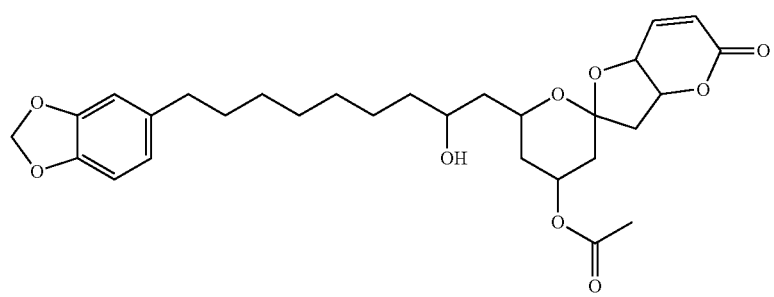
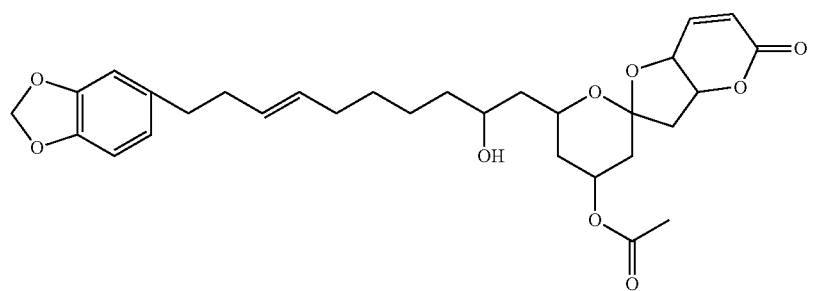

-continued
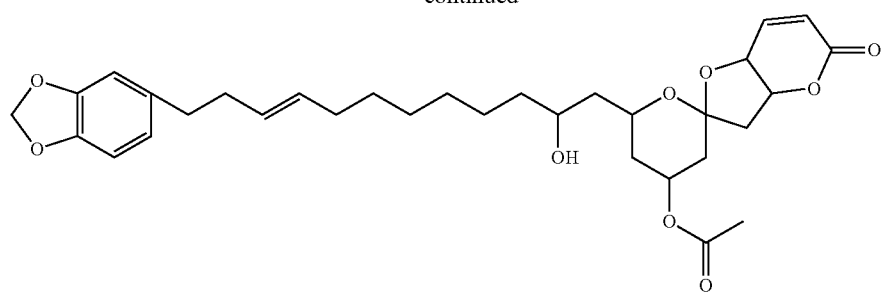
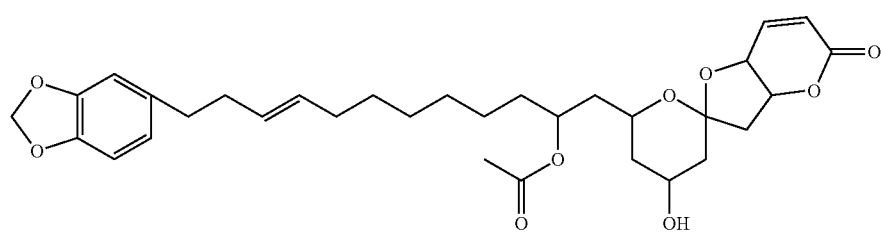
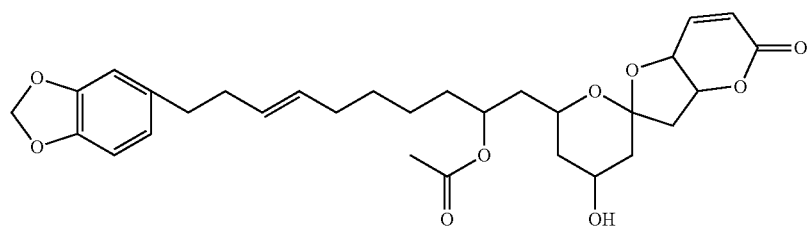
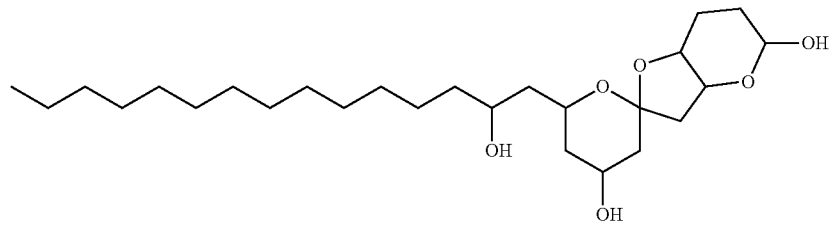
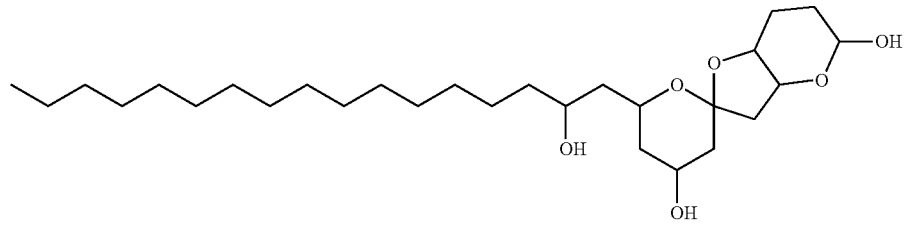
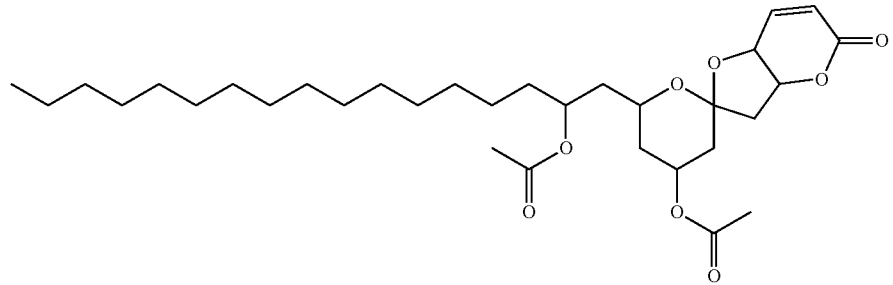

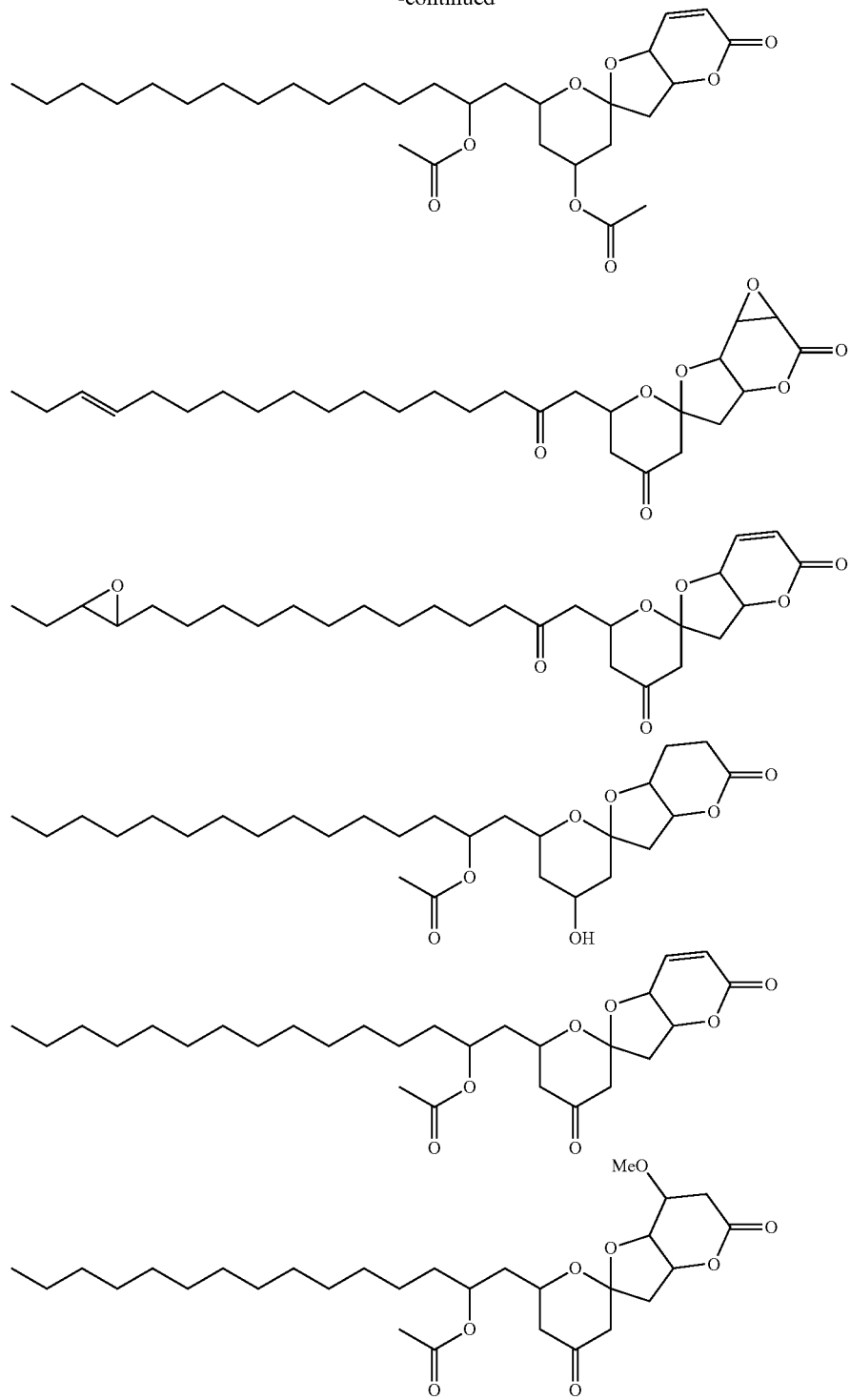

The term "alkyl" refers to optionally substituted linear and branched hydrocarbon groups having 1 to 20 carbon atoms. Where appropriate, the alkyl group may have a specified number of carbon atoms, for example, —$C_1$-$C_6$ alkyl which includes alkyl groups having 1, 2, 3, 4, 5 or 6 carbon atoms in linear or branched arrangements. Non-limiting examples of alkyl groups include methyl, ethyl, propyl, isopropyl, butyl, s- and t-butyl, pentyl, 2-methylbutyl, 3-methylbutyl, hexyl, heptyl, 2-methylpentyl, 3-methylpentyl, 4-methylpentyl, 2-ethylbutyl, 3-ethylbutyl, octyl, nonyl, decyl, undecyl, dodecyl, tridecyl, tetradecyl, pentadecyl.

The term "alkenyl" refers to optionally substituted unsaturated linear or branched hydrocarbon groups, having 2 to 20 carbon atoms and having at least one double bond. Where appropriate, the alkenyl group may have a specified number of carbon atoms, for example, $C_2$-$C_6$ alkenyl which includes alkenyl groups having 2, 3, 4, 5 or 6 carbon atoms in linear or branched arrangements. Non-limiting examples of alkenyl groups include, ethenyl, propenyl, isopropenyl, butenyl, s- and t-butenyl, pentenyl, hexenyl, hept-1,3-diene, hex-1,3-diene, non-1,3,5-triene and the like.

The term "alkynyl" refers to optionally substituted unsaturated linear or branched hydrocarbon groups, having 2 to 20 carbon atoms and having at least one triple bond. Where appropriate, the alkynyl group may have a specified number of carbon atoms, for example, $C_2$-$C_6$ alkynyl groups have 2, 3, 4, 5 or 6 carbon atoms in linear or branched arrangements. Non-limiting examples of alkynyl groups include ethynyl, propynyl, butynyl, pentynyl, hexynyl and the like.

The terms "cycloalkyl" and "carbocyclic" refer to optionally substituted saturated or unsaturated mono-cyclic, bicyclic or tricyclic carbon groups. Where appropriate, the cycloalkyl group may have a specified number of carbon atoms, for example, $C_3$-$C_6$ cycloalkyl is a carbocyclic group having 3, 4, 5 or 6 carbon atoms. Non-limiting examples may include cyclopropyl, cyclobutyl, cyclopentyl, cyclopentenyl, cyclohexyl, cyclohexenyl, cyclohexadienyl and the like.

"Aryl" means a $C_6$-$C_{14}$ membered monocyclic, bicyclic or tricyclic carbocyclic ring system having up to 7 atoms in each ring, wherein at least one ring is aromatic. Examples of aryl groups include, but are not limited to, phenyl, naphthyl, tetrahydronaphthyl, indanyl and biphenyl. The aryl may comprise 1-3 benzene rings. If two or more aromatic rings are present, then the rings may be fused together, so that adjacent rings share a common bond.

"Heterocyclic" or "heterocyclyl" refers to a non-aromatic ring having 3 to 8 atoms in the ring and of those atoms 1 to 4 are heteroatoms, said ring being isolated or fused to a second ring selected from 3- to 7-membered alicyclic ring containing 0 to 4 heteroatoms, wherein said heteroatoms are independently selected from O, N and S. Heterocyclic includes partially and fully saturated heterocyclic groups. Heterocyclic systems may be attached to another moiety via any number of carbon atoms or heteroatoms of the radical and may be both saturated and unsaturated, which includes all forms of carbohydrate moieties. Non-limiting examples of heterocyclic include pyrrolidinyl, pyrrolinyl, pyranyl, piperidinyl, piperazinyl, morpholinyl, tetrahydrofuranyl, tetrahydrothiophenyl, pyrazolinyl, dithiolyl, oxathiolyl, dioxanyl, dioxinyl, oxazinyl, azepinyl, diazepinyl, thiazepinyl, oxepinyl and thiapinyl, imidazolinyl, thiomorpholinyl, and the like.

The term "heteroaryl" as used herein means a stable monocyclic or bicyclic ring of up to 7 atoms in each ring, wherein at least one ring is aromatic and at least one ring contains from 1-4 heteroatoms, selected from sulfur, oxygen and nitrogen. Heteroaryl includes, but is not limited to, oxazolyl, thiazolyl, thienyl, furyl, 1-isobenzofuranyl, pyrrolyl, imidazolyl, pyrazolyl, isothiazolyl, isooxazolyl, pyridyl, pyrazinyl, pyrimidinyl, pyradazinyl, indolizinyl, isoindolyl, indolyl, purinyl, phthalazinyl, 1,2,3-triazolyl, 1,2,4-triazolyl, 1,2,3-oxadiazoyl, 1,2,4-oxadiazolyl, 1,2,5-oxadiazolyl, 1,3,4-oxadiazolyl, 1,2,3,4-oxatriazolyl, 1,2,3,5-oxatriazolyl, 1,3,5-triazinyl, 1,2,4-triazinyl, 1,2,3-triazinyl, benzofuranyl, isobenzofuranyl, thionaphthenyl, isothionaphthenyl, indoleninyl, 2-isobenzazolyl, 1,5-pyrindinyl, pyrano[3,4-b]pyrrolyl, isoindazolyl, indoxazinyl, benzoxazolyl, quinolinyl, isoquinolinyl, cinnolinyl, quinazolinyl, naphthyridinyl, pyrido[3,4-b]pyridinyl, pyrido[3,2-b]pyridinyl, pyrido[4,3-b]pyridinyl, acridinyl, carbazolyl, quinaoxalinyl, pyrazolyl, benzotriazolyl, thiophenyl, isoquinolinyl, pyridinyl, tetrahydroquinolinyl, benzazepinyl, benzodioxanyl, benzoxepinyl, benzodiazepinyl, benzothiazepinyl and benzothiepinyl and the like.

The alkyl, alkenyl, alkynyl, cycloalkyl, aryl, heteroaryl and heterocyclyl groups may be substituted with one or more substituent independently selected from —F, —Cl, —Br, —I, —$CO_2$R, —CN, —OR, —SR, —N(R)$_2$, —$NO_2$, —NROR, —ON(R)$_2$, —SOR, —$SO_2$R, —$SO_3$R, —SON(R)$_2$, —$SO_2$N(R)$_2$, —$SO_3$N(R)$_2$, —P(R)$_3$, —P(=O)(R)$_3$, —OSi(R)$_3$, —OB(R)$_2$ wherein R is as defined above.

As used herein, the terms "halo" or "halogen" refers to fluorine (fluoro), chlorine (chloro), bromine (bromo) and iodine (iodo).

Yet another aspect of the invention provides a pharmaceutically, agriculturally or pesticidally acceptable salt of a compound of formula (I) or formula (II).

The terms "pharmaceutically acceptable salts", "agriculturally acceptable salts" or "pesticidally acceptable salts" as used herein refer to salts which are toxicologically safe for systemic or localised administration or suitable for application to a plant or an agricultural, industrial or household environment. The pharmaceutically, agriculturally or pesticidally acceptable salts may be selected from the group including alkali and alkali earth, ammonium, aluminium, iron, amine, glucosamine, chloride, sulphate, sulphonate, bisulphate, nitrate, citrate, tartrate, bitarate, phosphate, carbonate, bicarbonate, malate, maleate, napsylate, fumarate, succinate, acetate, benzoate, terephthalate, palmoate, pectinate and s-methyl methionine salts, piperazine and the like.

It will also be recognised that compounds of the invention may possess asymmetric centres and are therefore capable of existing in more than one stereoisomeric form. The invention thus also relates to compounds in substantially pure isomeric form at one or more asymmetric centres e.g., greater than about 90% ee, such as about 95% or 97% ee or greater than 99% ee, as well as mixtures, including racemic mixtures, thereof. Such isomers may be obtained by isolation from natural sources, by asymmetric synthesis, for example using chiral intermediates, or by chiral resolution. The compounds of the invention may exist as geometrical isomers. The invention also relates to compounds in substantially pure cis (Z) or trans (E) forms or mixtures thereof.

The compounds of the present invention may be obtained by isolation from a plant or plant part, or by derivatisation of the isolated compound, or by derivatisation of a related compound.

Still yet another aspect of the invention provides a method of isolating one or more compounds of formula (I) or formula (II), which method includes the step of extracting said one or more compounds from a plant or plant part.

Preferably, the plant is of the family Lauraceae.

Preferably, the genus is *Litsea, Cinnamomum, Cryptocarya, Beilschmiedia, Endiandra, Neolitsea* and *Lindera*.

Preferably the species is *Litsea* spp. such as *Litsea sebifera, Litsea polyantha, Litsea cassiaefolia, Litsea elliptica, Litsea ferruginea, Litsea firma, Litsea garciae, Litsea oppositifolia, Litsea australis, Litsea bennettii, Litsea bindoniana, Litsea breviumbellata, Litsea connorsii, Litsea fawcettiana, Litsea glutinosa, Litsea granitica, Litsea leefeana, Litsea macrophylla, Litsea reticulata;* especially *Litsea breviumbellata, Litsea connorsii* and *Litsea leefeana; Cinnamomum* spp. such as *Cinnamomum acuminatifolium, Cinnamomum acuminatissimum, Cinnamomum acutatum, Cinnamomum africanum, Cinnamomum aggregatum, Cinnamomum alainii, Cinnamomum alatum, Cinnamomum albiflorum, Cinnamomum alcinii, Cinnamomum alexei, Cinnamomum alibertii, Cinnamomum alternifolium, Cinnamomum altissimum, Cinnamomum ammannii, Cinnamomum amoenum, Cinnamomum amplexicaule, Cinnamomum amplifolium, Cinnamomum anacardium, Cinnamomum andersonii, Cinnamomum angustifolium, Cinnamomum angustitepalum, Cinnamomum antillarum, Cinnamomum appelianum, Cinnamomum arbus-*

*culum, Cinnamomum archboldianum, Cinnamomum areolatocostae, Cinnamomum areolatum, Cinnamomum areolatum, Cinnamomum arfakense, Cinnamomum argenteum, Cinnamomum aromaticum, Cinnamomum arsenei, Cinnamomum asa-grayi, Cinnamomum assamicum, Cinnamomum aubletii, Cinnamomum aureo-fulvum, Cinnamomum australe, Cinnamomum austro-sinense, Cinnamomum austroyunnanense, Cinnamomum bahianum, Cinnamomum bahiense, Cinnamomum baileyanum, Cinnamomum baillonii, Cinnamomum balansae, Cinnamomum bamoense, Cinnamomum barbato-axillatum, Cinnamomum barbeyanum, Cinnamomum barlowii, Cinnamomum bartheifolium, Cinnamomum barthii, Cinnamomum bazania, Cinnamomum beccarii, Cinnamomum bejolghota, Cinnamomum bengalense, Cinnamomum biafranum, Cinnamomum bintulense, Cinnamomum birmanicum, Cinnamomum blumei, Cinnamomum bodinieri, Cinnamomum bonii, Cinnamomum bonplandii, Cinnamomum borneense, Cinnamomum bourgeauvianum, Cinnamomum boutonii, Cinnamomum brachythyrsum, Cinnamomum bractefoliaceum, Cinnamomum burmannii, Cinnamomum camphora, Cinnamomum cassia* (syn. *C. aromaticum*), *Cinnamomum caudiferum, Cinnamomum chartophyllum, Cinnamomum citriodorum, Cinnamomum contractum, Cinnamomum filipes, Cinnamomum glanduliferum, Cinnamomum glaucescens, Cinnamomum ilicioides, Cinnamomum impressinervium, Cinnamomum iners, Cinnamomum japonicum, Cinnamomum javanicum, Cinnamomum jensenianum, Cinnamomum kotoense, Cinnamomum kwangtungense, Cinnamomum liangii, Cinnamomum longepaniculatum, Cinnamomum longipetiolatum, Cinnamomum loureiroi, Cinnamomum mairei, Cinnamomum micranthum, Cinnamomum migao, Cinnamomum mollifolium, Cinnamomum oliveri, Cinnamomum osmophloeum, Cinnamomum parthenoxylon, Cinnamomum pauciflorum, Cinnamomum philippinense, Cinnamomum pingbienense, Cinnamomum pittosporoides, Cinnamomum platyphyllum, Cinnamomum porphyrium, Cinnamomum propinquum, Cinnamomum reticulatum, Cinnamomum rigidissimum, Cinnamomum saxatile, Cinnamomum septentrionale, Cinnamomum subavenium, Cinnamomum tamala, Cinnamomum tenuipilum, Cinnamomum tonkinense, Cinnamomum triplinerve, Cinnamomum tsangii, Cinnamomum tsoi, Cinnamomum validinerve, Cinnamomum verum, Cinnamomum virens, Cinnamomum wilsonii* and *Cinnamomum laubatii* especially *Cinnamomum laubatii, Cinnamomum oliveri, Cinnamomum virens* and *Cinnamomum camphora*; or *Cryptocarya* spp. such as *C. alba, C. angulata, C. aristata, C. ashersoniana, C. chinensis, C. cinnamomifolia, C. corrugata, C. crassinervia, C. cunninghamiana, C. densiflora, C. ferrea, C. foetida, C. gigantocarpa, C. glaucescens, C. grandis, C. hypospodia, C. invasorium, C. laevigata, C. leptospermoides, C. mackinnoniana, C. massoia, C. meissneri, C. membranaceae, C. multipaniculata, C. murrayi, C. nigra, C. nitens, C. oblata, C. odorata, C. palawanensis, C. pleurosperma, C. pluricostata, C. rigida, C. scortechinii, C. transversa, C. tomentosa, C. triplinervis, C. vulgaris, C. angulata, C. bamagana, C. bellendenkerana, C. bidwillii, C. brassii, C. burckiana, C. clarksoniana, C. claudiana, C. cocosoides, C. cunninghamii, C. endiandrifolia, C. erythoxylon, C. exfoliata, C. floydii, C. foveolata, C. glaucocarpa, C. leucophylla, C. lividula, C. macdonaldii, C. meisneriana, C. melanocarpa, C. microneura, C. obovata, C. onoprienkoana, C. putida, C. rhodosperma, C. saccharata, C. sclerophylla, C. smaragdina, C. sp Boonjee, C. sp Gadgarra, C. triplinervis var. riparia*; especially *C. angulata, C. bamagana, C. bellendenkerana, C. bidwillii, C. brassii, C. clarksoniana, C. cocosoides, C. corrugata, C. cunninghamii, C. exfoliata, C. glaucescens, C. grandis, C. hypospodia, C. laevigata, C. leucophylla, C. lividula, C. macdonaldii, C. mackinnoniana, C. melanocarpa, C. microneura, C. murrayi, C. oblata, C. onoprienkoana, C. pleurosperma, C. putida, C. rhodosperma, C. triplinervis* var. *riparia, C. vulgaris; Beilschmiedia bancroftii, Beilschmiedia brunnea, Beilschmiedia castrisinensis, Beilschmiedia collina, Beilschmiedia elliptica, Beilschmiedia obtusifolia, Beillschmiedia oligandra, Beilschmiedia peninsularis, Beilschmiedia recurva, Beilschmiedia tooram, Beilschmiedia volckii*; especially *Beilschmiedia bancroftii, Beilschmiedia castrisinensis, Beilschmiedia peninsularis, Beilschmiedia recurva, Beilschmiedia tooram, Beilschmiedia volckii; Endiandra acuminata, Endiandra anthropophagorum, Endiandra bellendenkerana, Endiandra bessaphila, Endiandra collinsii, Endiandra compressa, Endiandra cooperana, Endiandra cowleyana, Endiandra crassiflora, Endiandra dichrophylla, Endiandra dielsiana, Endiandra discolor, Endiandra floydii, Endiandra glauca, Endiandra globosa, Endiandra grayi, Endiandra hayesii, Endiandra hypotephra, Endiandra impressicosta, Endiandra insignis, Endiandra introrsa, Endiandra jonesii, Endiandra leptodendron, Endiandra limnophila, Endiandra longipedicellata, Endiandra microneura, Endiandra monothyra* subsp *monothyra, Endiandra monothyra* subsp *trichophylla, Endiandra montana, Endiandra muelleri, Endiandra palmerstonii, Endiandra phaeocarpa, Endiandra sankeyana, Endiandra sideroxylon, Endiandra sieberi, Endiandra virens, Endiandra wolfei, Endiandra xanthocarpa*; especially *Endiandra bessaphila, Endiandra compressa, Endiandra globosa, Endiandra insignis, Endiandra jonesii, Endiandra microneura, Endiandra monothyra* subsp *monothyra, Endiandra montana, Endiandra palmerstonii, Endiandra sankeyana; Neolitsea australiensis, Neolitsea brassii, Neolitsea dealbata*; especially *Neolitsea dealbata*; and *Lindera queenslandica*.

The parts of the plant may include fruit, seed, bark, leaf, flower, roots and wood.

Preferably the extract is obtained from the seed, epicarp or mesocarp.

For example, the biomass obtained from seeds, leaves and bark of the plant is subject to initial solvent extraction, for example with a polar solvent such as methanol. The initial extraction is then concentrated and diluted with water and subject to extraction with a second solvent, for example, ethyl acetate. The solvent samples from the second extraction are pooled and subject to separation by preparative HPLC fractionation. The fractions are analysed by analytical HPLC and pooled according to the retention time of compounds found in the samples. The pooled fractions are weighed, bioassayed and analysed by analytical HPLC. Further fractionation using one or more preparative HPLC is performed to isolate specific compounds. Each compound is bioassayed and its structure identified by UV, NMR and mass spectrometric techniques.

Other compounds of the invention may be obtained by derivatising compounds isolated from plants or parts of plants, especially from the genus *Litsea, Cinnamomum* and *Cryptocarya*.

Derivatives of the natural compounds can be obtained by techniques known in the art. For example, hydroxy groups may be oxidised, to ketones, aldehydes or carboxylic acids by exposure to oxidising agents such as chromic acid, Jones' reagent, KMnO$_4$, peracids such as mCPBA (metachloroperbenzoic acid) or dioxiranes such as dimethyldioxirane (DMDO) and methyl(trifluoromethyl)dioxirane (TFDO). Oxidising agents may be chosen such that other functional groups in the molecule are or are not also oxidised. For example, a primary alcohol may be selectively oxidised to an aldehyde or carboxylic acid in the presence of secondary alcohols using reagents such as RuCl$_2$(PPh$_3$)$_3$-benzene. Secondary alcohols may be selectively oxidised to ketones in the presence of a primary alcohol using Cl$_2$-pyridine or NaBrO$_3$-ceric-ammonium nitrate. Alcohols may be oxidised in the presence double and triple bonds and without epimerisation at adjacent stereocentres using Jone's reagent. Alternatively, reagents chosen may be less selective resulting in oxidation at more than one functional group.

Hydroxy groups may also be derivatised by etherification or acylation. For example, ethers may be prepared by formation of an alkoxide ion in the presence of base and reacting the alkoxide with an appropriate alkylhalide, alkenylhalide, alkynylhalide or arylhalide. Similarly acylation may be achieved by formation of an alkoxide ion and reaction with an appropriate carboxylic acid or activated carboxylic acid (such as an anhydride).

Acyl groups may be hydrolysed to provide alcohols by acid or base hydrolysis as known in the art.

Silyl groups may be introduced onto hydroxy groups to provide silyl ethers using mild base and a silyl chloride reagent, for example Me$_3$SiCl and triethylamine in THF or agents such as MeSiNHCO$_2$SiMe$_3$ in THF.

Sulfonates may be readily introduced onto hydroxy groups by reaction with a suitable sulfonate group. For example, methanesulfonates may be introduced by treatment of a hydroxy group with MsCl and triethylamine in dichloromethane. Tosylate groups may be introduced by reacting a hydroxy group with TsCl and pyridine. Allylsulfonates may be introduced by reacting a hydroxy group with allylsulfonyl chloride and pyridine in dichloromethane.

Ketones may be reduced to secondary alcohols by reducing agents such as lithium aluminium hydride and other metal hydrides without reducing double bonds, including α-unsaturated ketones.

Double bonds and triple bonds may be reduced to single bonds using catalytic reduction, for example, H$_2$/Pd. Double bonds may also be oxidised to epoxides using oxidising agents such as per acids, for example mCPBA or dioxiranes, such as DMDO and TFDO. Double bonds may also be subject to addition reactions to introduce substituents such as halo groups, hydroxy or alkoxy groups and amines.

A person skilled in the art would be able to determine suitable conditions for obtaining derivatives of isolated compounds, for example, by reference to texts relating to synthetic methodology, examples of which are Smith M. B. and March J., March's Advanced Organic Chemistry, Fifth Edition, John Wiley & Sons Inc., 2001 and Larock R. C., Comprehensive Organic Transformations, VCH Publishers Ltd., 1989. Furthermore, selective manipulations of functional groups may require protection of other functional groups. Suitable protecting groups to prevent unwanted side reactions are provided in Green and Wuts, Protective Groups in Organic Synthesis, John Wiley & Sons Inc., 3$^{rd}$ Edition, 1999.

The compounds of the invention may also be synthesised from commercially available starting materials. Three synthetic pathways to synthesise the EBI-23 are set out below:

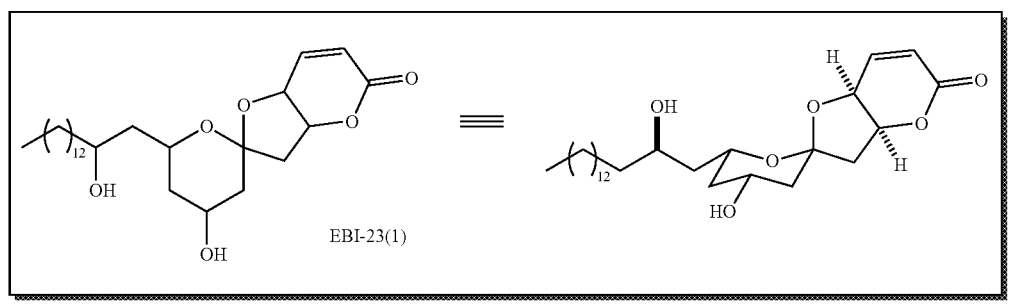

Synthesis 1

The first approach to EBI-23 (1) was based on a convergent synthesis of two halves, the lactone (2) and triol (3).

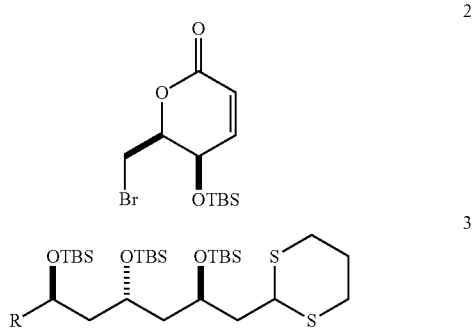

The triol 3 was prepared asymmetrically in 9 steps by the following protocol (Scheme 1). Epoxide 4 was resolved into the R-stereoisomer 5 using Jacobsen's catalyst (R,R). Epoxide 5 was ring opened with vinyl magnesium bromide in the presence of copper (I) iodide and the resulting alcohol protected as a TBS ether (6). TBS ether 6 was converted to epoxide 7 using meta-chloroperbenzoic acid (mCPBA) followed by kinetic resolution with Jacobsen's catalyst (S,S). Epoxide 7 was subject to the same sequence affording epoxide 8 which was reacted with the dithiane 9 producing dithiane 3.

Scheme 1

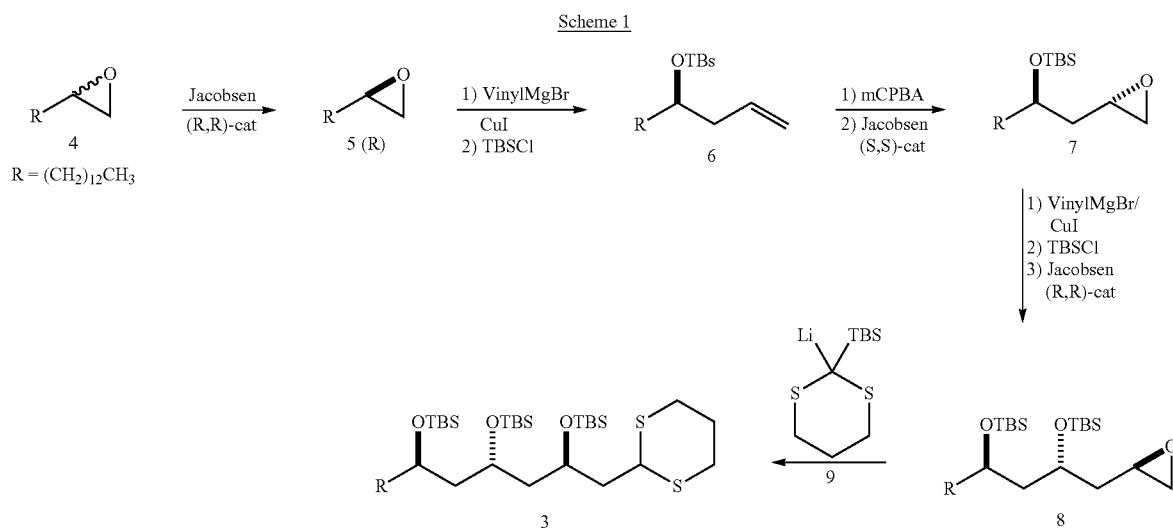

Alternatively, 8 can be prepared by Scheme 1.1 below:

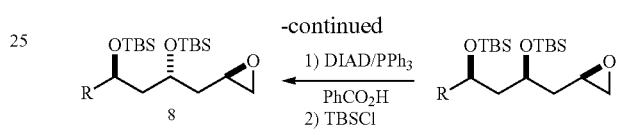

The right hand portion of EBI-23, that is lactone 2, is obtained from pyrone 13, which is constructed according to the literature (e.g. Harris et al., *Strategies and Tactics in Organic Synthesis,* 2004, 5, 221 and O'Doherty et al., *Organic Letters* 2000, 2, 2983-2986, *Tetrahedron Letters* 2000, 41, 183-187). Diol 10 is mono TBS protected (i.e. 11) and then ring enlarged (NBS/H$_2$O) affording the lactol 12. Jones oxidation followed by stereoselective Luche reduction produces 13, which can be transformed into the bromide (lactone) 2, by two different protocols, after TBS protection and selective deprotection of the primary TBS ether. The first protocol converts the alcohol (13) to the mesylate 14, which undergoes a Finkelstein reaction with lithium bromide giving 2. The second procedure converts directly the alcohol 13 into 2 using tetrabromomethane and triphenylphosphine (Scheme 2).

Scheme 2

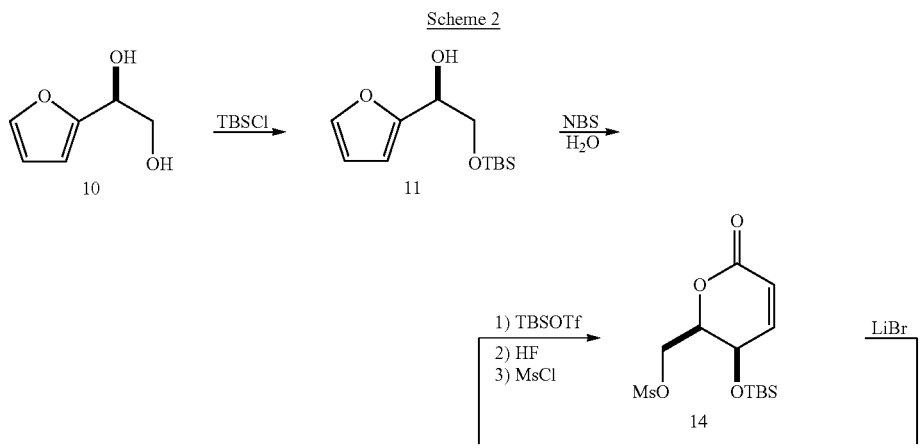

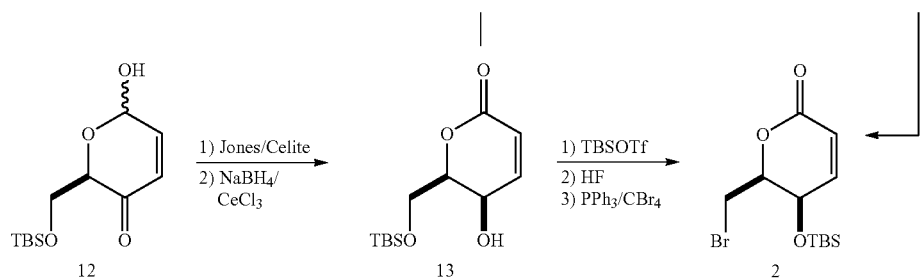

Both halves, that is 2 and 3, are coupled (15) by butyl lithium deprotonation of dithiane 3 and addition of the anion to bromide 2. The resulting dithiane is deprotected wth mercury salts affording ketone 16, which undergoes TBS deprotection and subsequent acid catalysed ring closure affording EBI-23 (Scheme 3).

Scheme 3

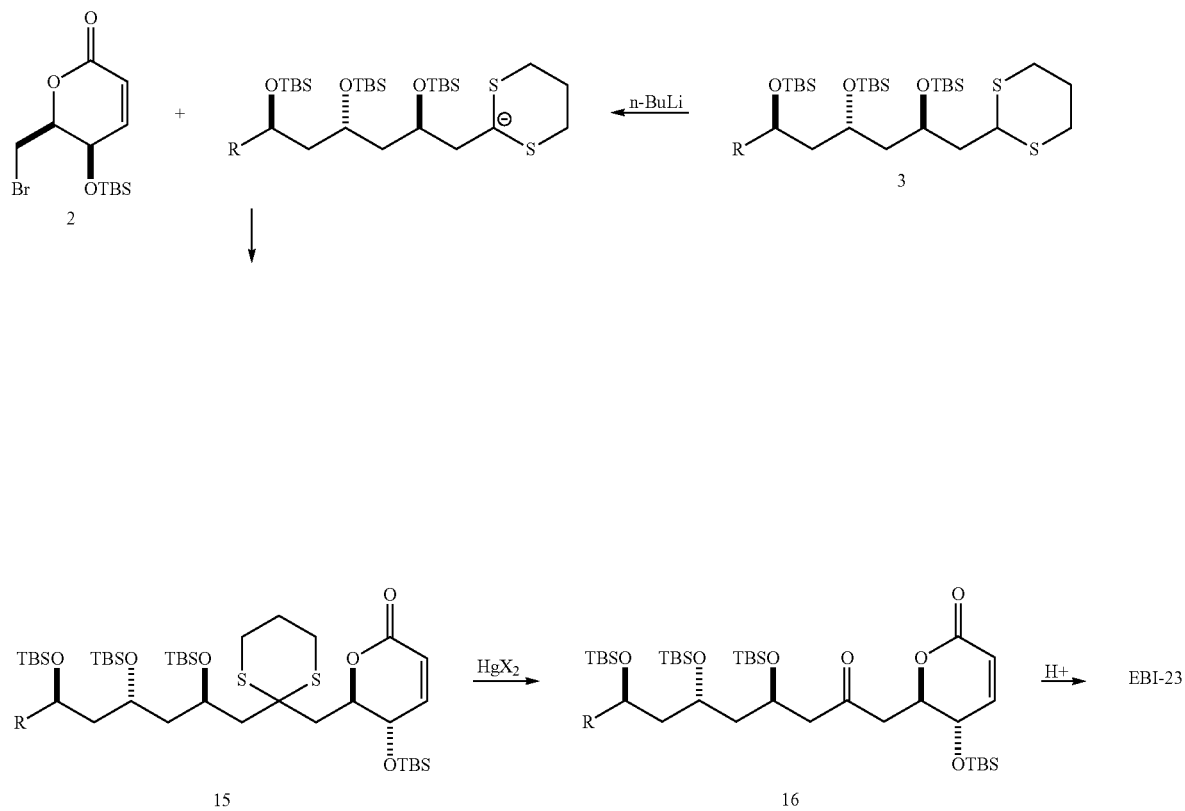

Synthesis 2

Route 2 (Scheme 4) is based on a Grubb's ring closing metathesis (RCM) strategy. Reaction of triol 3 with known epoxide 17 followed by acylation (acrolyl chloride) and RCM will give rapid access to lactone 15, which on treatment with mercury salts and subsequent acid catalyst provides EBI-23.

Scheme 4

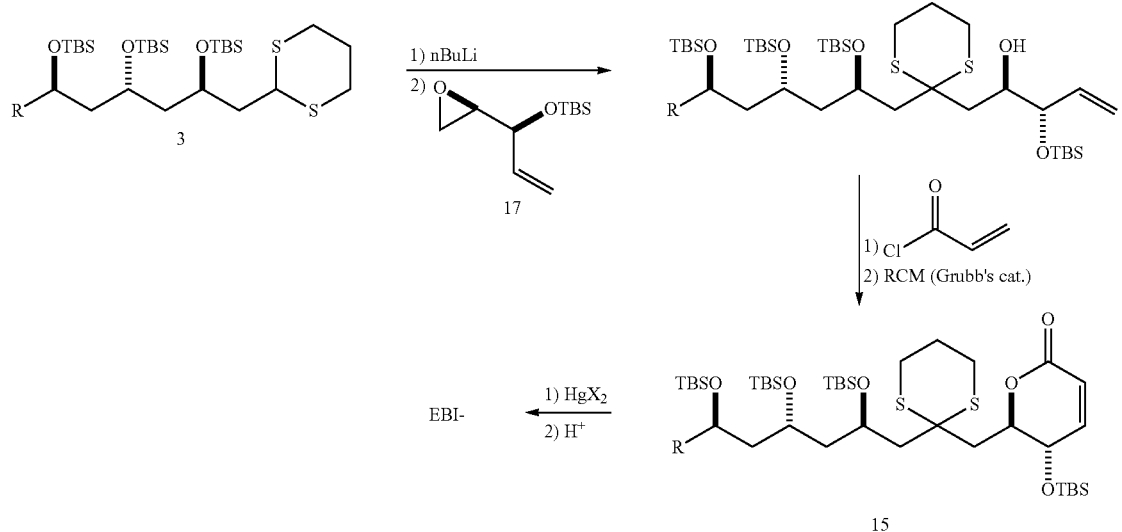

Synthesis 3

Route 3 (Scheme 5) utilises acetylene chemistry, in that epoxide 8 is converted into acetylene 18, using sodium acetylide followed by TBS protection. Treatment of 18 with butyl lithium and reaction with 2-furfural affords furan 19. Furan 19 undergoes ring enlargement, Jones oxidation, Luche reduction and TBS protection giving 20, which on exposure to acid reveals EBI-23. Unfortunately, this approach lacks stereocontrol at one position.

Use of variously substituted starting materials will give rise to substitution on the spiroketal products.

A further aspect of the invention provides a pharmaceutical composition for treatment or prophylaxis of a disease or condition comprising an effective amount of one or more compounds of formula (I) or formula (II), or a pharmaceutically acceptable salt thereof, and a pharmaceutically acceptable carrier, diluent and/or excipient.

Dosage form and rates for pharmaceutical use and compositions are readily determinable by a person of skill in the art.

Scheme 3

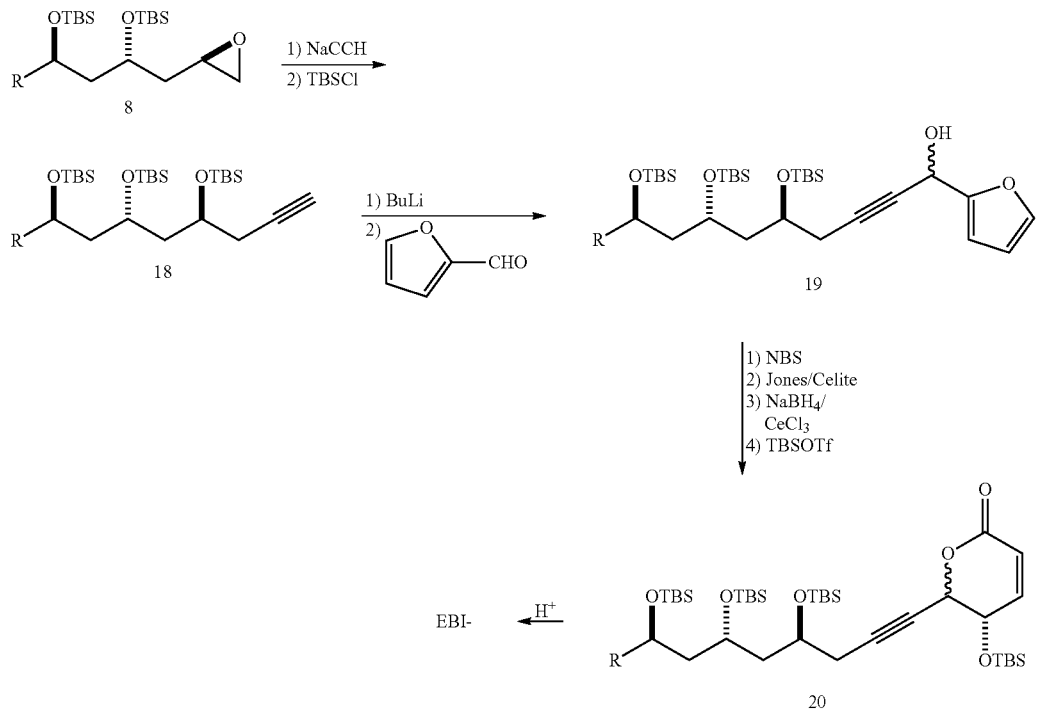

Dosage forms include tablets, dispersions, suspensions, injections, solutions, syrups, troches, capsules, suppositories, aerosols, transdermal patches and the like. These dosage forms may also include injecting or implanting devices designed specifically for, or modified to, controlled release of the pharmaceutical composition. Controlled release of the therapeutic agent may be effected by coating the same, for example, with hydrophobic polymers including acrylic resins, waxes, higher aliphatic alcohols, polylactic and polyglycolic acids and certain cellulose derivates such as hydroxypropylmethyl cellulose. In addition, the controlled release may be affected by using other polymer matrices, liposomes and/or microspheres.

Pharmaceutically acceptable carriers and acceptable carriers for systemic administration may also be incorporated into the compositions of this invention.

Suitably, the pharmaceutical composition comprises a pharmaceutically acceptable excipient or an acceptable excipient. By "pharmaceutically acceptable excipient" is meant a solid or liquid filler, diluent or encapsulating substance that may be safely used in systemic administration. Depending upon the particular route of administration, a variety of carriers, well known in the art may be used. These carriers or excipients may be selected from a group including sugars, starches, cellulose and its derivates, malt, gelatine, talc, calcium sulphate, vegetable oils, synthetic oils, polyols, alginic acid, phosphate buffered solutions, emulsifiers, isotonic saline, and pyrogen-free water.

Any suitable route of administration may be employed for providing a human or non-human with the pharmaceutical composition of the invention. For example, oral, rectal, parenteral, sublingual, buccal, intravenous, intraarticular, intra-muscular, intradermal, subcutaneous, inhalational, intraocular, intraperitoneal, intracerebroventricular, transdermal and the like may be employed.

Pharmaceutical compositions of the present invention suitable for administration may be presented in discrete units such as vials, capsules, sachets or tablets each containing a predetermined amount of one or more pharmaceutically active compounds of the invention, as a powder or granules or as a solution or a suspension in an aqueous liquid, a non-aqueous liquid, an oil-in-water emulsion or a water-in-oil emulsion. Such compositions may be prepared by any of the method of pharmacy but all methods include the step of bringing into association one or more pharmaceutically active compounds of the invention with the carrier which constitutes one or more necessary ingredients. In general, the compositions are prepared by uniformly and intimately admixing the agents of the invention with liquid carriers or finely divided solid carriers or both, and then, if necessary, shaping the product in to the desired presentation.

In powders, the carrier is a finely divided solid which is in a mixture with the finely divided active component.

In tablets, the active component is mixed with the carrier having the necessary binding capacity in suitable proportions and compacted in the shape and size desired.

The powders and tablets preferably contain from five or ten to about seventy percent of the active compound. Suitable carriers are magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. The term "preparation" is intended to include the formulation of the active compound with encapsulating material as carrier providing a capsule in which the active component, with or without carriers, is surrounded by a carrier, which is thus in association with it. Similarly, cachets and lozenges are included. Tablets, powders, capsules, pills, cachets, and lozenges can be used as solid forms suitable for oral administration.

For preparing suppositories, a low melting wax, such as admixture of fatty acid glycerides or cocoa butter, is first melted and the active component is dispersed homogeneously therein, as by stirring. The molten homogenous mixture is then poured into convenient sized molds, allowed to cool, and thereby to solidify.

Formulations suitable for vaginal administration may be presented as pessaries, tampons, creams, gels, pastes, foams or sprays containing in addition to the active ingredient such carriers as are known in the art to be appropriate.

Liquid form preparations include solutions, suspensions, and emulsions, for example, water or water-propylene glycol solutions. For example, parenteral injection liquid preparations can be formulated as solutions in aqueous polyethylene glycol solution.

The compounds according to the present invention may thus be formulated for parenteral administration (e.g. by injection, for example bolus injection or continuous infusion) and may be presented in unit dose form in ampoules, pre-filled syringes, small volume infusion or in multi-dose containers with an added preservative. The compositions may take such forms as suspensions, solutions, or emulsions in oily or aqueous vehicles, and may contain formulatory agents such as suspending, stabilising and/or dispersing agents. Alternatively, the active ingredient may be in powder form, obtained by aseptic isolation of sterile solid or by lyophilisation from solution, for constitution with a suitable vehicle, e.g. sterile, pyrogen-free water, before use.

Aqueous solutions suitable for oral use can be prepared by dissolving the active component in water and adding suitable colorants, flavours, stabilizing and thickening agents, as desired.

Aqueous suspensions suitable for oral use can be made by dispersing the finely divided active component in water with viscous material, such as natural or synthetic gums, resins, methylcellulose, sodium carboxymethylcellulose, or other well known suspending agents.

Also included are solid form preparations which are intended to be converted, shortly before use, to liquid form preparations for oral administration. Such liquid forms include solutions, suspensions, and emulsions. These preparations may contain, in addition to the active component, colorants, flavours, stabilizers, buffers, artificial and natural sweeteners, dispersants, thickeners, solubilizing agents, and the like.

For topical administration to the epidermis the compounds according to the invention may be formulated as ointments, creams or lotions, or as a transdermal patch. Ointments and creams may, for example, be formulated with an aqueous or oily base with the addition of suitable thickening and/or gelling agents. Lotions may be formulated with an aqueous or oily base and will in general also contain one or more emulsifying agents, stabilising agents, dispersing agents, suspending agents, thickening agents, or colouring agents.

Formulations suitable for topical administration in the mouth include lozenges comprising active agent in a flavoured base, usually sucrose and acacia or tragacanth; pastilles comprising the active ingredient in an inert base such as gelatin and glycerin or sucrose and acacia; and mouthwashes comprising the active ingredient in a suitable liquid carrier.

Solutions or suspensions are applied directly to the nasal cavity by conventional means, for example with a dropper, pipette or spray. The formulations may be provided in single or multidose form. In the latter case of a dropper or pipette, this may be achieved by the patient administering an appropriate, predetermined volume of the solution or suspension. In the case of a spray, this may be achieved for example by means of a metering atomising spray pump. To improve nasal delivery and retention the compounds according to the invention may be encapsulated with cyclodextrins, or formulated with their agents expected to enhance delivery and retention in the nasal mucosa.

Administration to the respiratory tract may also be achieved by means of an aerosol formulation in which the active ingredient is provided in a pressurised pack with a suitable propellant such as a chlorofluorocarbon (CFC) for example, dichlorodifluoromethane, trichlorofluoromethane, or dichlorotetrafluoroethane, carbon dioxide, or other suitable gas. The aerosol may conveniently also contain a surfactant such as lecithin. The dose of drug may be controlled by provision of a metered valve.

Alternatively the active ingredients may be provided in the form of a dry powder, for example a powder mix of the compound in a suitable powder base such as lactose, starch, starch derivatives such as hydroxypropylmethyl cellulose and polyvinylpyrrolidone (PVP).

Conveniently the powder carrier will form a gel in the nasal cavity. The powder composition may be presented in unit dose form for example in capsules or cartridges of, e.g., gelatin, or blister packs from which the powder may be administered by means of an inhaler.

In formulations intended for administration to the respiratory tract, including intranasal formulations, the compound will generally have a small particle size for example of the order of 1 to 10 microns or less. Such a particle size may be obtained by means known in the art, for example by micronization.

The active compounds of the invention and of the composition of this invention are present in an amount sufficient to prevent, inhibit or ameliorate one or more diseases or conditions selected from the group consisting of: a bacterial infection, a protozoal infection, a parasitic infestation, a cell proliferative disorder, an inflammatory disorder or a pest infestation. Suitable dosages of the compounds of the invention and the pharmaceutical compositions containing such may be readily determined by those skilled in the art.

In a further aspect of the invention, there is provided a method of treating or preventing of a disease or condition comprising administering to a subject in need of such treatment an effective amount of one or more compounds according to the invention, or a pharmaceutically acceptable salt thereof.

In yet another aspect of the invention, there is provided the use of one or more of the compounds according to the invention, or a pharmaceutically acceptable salt thereof, in the manufacture of a medicament for the treatment or prophylaxis of a disease or condition.

In non-limiting embodiments compounds of the invention have one or more activities selected from antiparasitic activity (e.g., against an endoparasite and/or an ectoparasite, such as, *Haemonchus contortus*), antibiotic activity (e.g., against *Bacillus subtilis*), antiprotozoal activity (e.g., against *Giardia* sp. Portland) cytotoxic activity (e.g., against a basal cell carcinoma and/or a squamous cell carcinoma and/or a melanoma and/or a fibrosarcoma and/or a murine myeloma, and/or anti-tumor activity (e.g., against a leukemia, a melanoma, a prostate cancer, a breast cancer, an ovarian cancer and/or other solid tumor cancers), anti-inflammatory or immunosuppressive activity and/or pesticidal activity.

In one aspect of the invention, there is provided a method of treating or preventing a bacterial infection comprising administering to a subject a compound of the invention or a pharmaceutically acceptable salt thereof.

In preferred embodiments, the compound of formula (I) and formula (II) is one of EBI-23, EBI-24 and EBI-25.

The bacterial infection may be caused by a Gram positive or Gram negative bacteria, especially Gram positive bacteria including bacteria of the Genus *Bacillus* (e.g. *B. subtilis, B. anthracis, B. cereus, B. firmis, B. licheniformis, B. megaterium, B. pumilus, B. coagulans, B. pantothenticus, B. alvei, B. brevis, B. circulans, B. laterosporus, B. macerans, B. polymyxa, stearothermophilus, B. thuringiensis, sphaericus*), *Staphylococcus* (e.g. *S. aureus, S. epidermidis, S. haemolyticus, S. saprophyticus*), *Streptococcus* (e.g. *S. pyogenes, S. pneumoniae, S. agalactiae, S. pyogenes, S. agalactiae, S. dysgalactiae, S. equisimilis, S. equi, S. zooepidemicus, S. anginosus, S. salivarius, S. milleri, S. sanguis, S. mitior, S. mutans, S. faecalis, S. faecium, S. bovis, S. equinus, S. uberus, S. avium*), *Aerococcus, Gemella, Corynebacterium, Listeria, Kurthia, Lactobacillus, Erysipelothrix, Arachnia, Actinomyces, Propionibacterium, Rothia, Bifidobacterium, Clostridium, Eubacterium, Nocardia, Mycobacterium*.

In another aspect of the invention there is provided a method of treating or preventing a parasitic infection comprising administering to a subject a compound of the invention or a pharmaceutically acceptable salt thereof.

In preferred embodiments, the parasite is a helminth (worm), especially nematodes, trematodes and cestodes, especially *Haemonchus contortus, Trichinella spiralis, H. placei, Bursaphelenchus xylophilus, Ostertagia circumcincta, O. ostertagi, Mecistocirrus digitatus, Trychostrongylus axei, Trichuris trichiura, T vulpis, T. campanula, T. suis, T. ovis, Bunostomum trigonocephalum, B. phleboyomum, Oesophagostomum columbianum, O. radiatum, Cooperia curticei, C. punctata, C. oncophora, C. pectinata, Strongyloides papillosus, Chabertia ovina, Ancylostoma duodenale, A. braziliense. A. tubaeforme, A. caninum, Ascaris lumbricoides, Enterobius vermicularis, E. gregorii, Ascaris lumbricoides, Paragonimus Westermani, Clonorchis sinensis, Fasciola hepatica, Taenia solium, T. saginata, Capillaria aerophile, Necator americanus*, species of the genus *Trichuris, Baylisascaris, Aphelenchoides, Meliodogyne, Heterodera, Globodera, Nacobbus, Pratylenchus, Ditylenchus, Xiphinema, Longidorus, Trichodorus, Nematodirus*.

In this embodiment, preferred compounds include EBI-23 and EBI-24.

In yet another aspect of the invention, there is provided a method of treating or preventing a cell proliferative disorder comprising administering to a subject a compound of the invention or a pharmaceutically acceptable salt thereof.

In a preferred embodiment, the cell proliferative disorder is a cancer, especially where the cancer is selected from leukaemia, melanoma, prostate cancer, breast cancer, ovarian cancer, basal cell carcinoma, squamous cell carcinoma, fibrosarcoma, colon cancer, lung cancer, a neoplasm and other solid tumor cancers.

In this embodiment, preferred compounds include EBI-23, EBI-24, EBI-25 and EBI-42.

The present invention further contemplates a combination of therapies, such as the administration of the compounds of the invention or pharmaceutically acceptable salts thereof together with the subjection of the subject to other agents or procedures which are useful in the treatment of cell proliferative disorders such as tumors. For example, the compounds of the present invention may be administered in combination with other chemotherapeutic drugs, or with other treatments such as radiotherapy. Suitable chemotherapeutic drugs include, but are not limited to, cyclophosphamide, doxorubicine, etoposide phosphate, paclitaxel, topotecan, camptothecins, 5-fluorouracil, tamoxifen, staurosporine, avastin, erbitux, imatinib and vincristine. The compounds of the invention may be administered simultaneously, separately or sequentially with the chemotherapeutic drug.

In yet another embodiment of the present invention, there is provided a method of treating or preventing a protozoan infection comprising administering to a subject a compound of the invention or a pharmaceutically acceptable salt thereof.

In a preferred embodiment, the protozoan infection is selected from *Giardia* spp., *Trichomonas* spp., *African trypanosomiasis*, amoebic dysentery, babesiosis, balantidial dysentery, Chaga's disease, coccidiosis, malaria and toxoplasmosis, especially *Giardia* spp. and *Trichomonas* spp. infections.

In this embodiment, preferred compounds include EBI-23, EBI-24 and EBI-25.

In yet another aspect of the present invention, there is provided a use of a compound of the invention in the manufacture of a medicament for treating or preventing a bacterial infection, a parasitic infection, a protozoan infection or a cell proliferative disorder.

In yet another aspect of the invention, there is provided a method of treating or preventing an inflammatory disorder comprising administering to a subject a compound of the invention or a pharmaceutically acceptable salt thereof.

In a preferred embodiment, the inflammatory disorder is general inflammation, rheumatoid arthritis, colitis, or a disorder associated with a malfunctioning immune system, such as an autoimmune disorder. In a preferred embodiment, the compound of the invention is capable of immunomodulation, especially immunosuppression. The compounds of the invention are also useful as immunosuppressive agents in organ transplantation.

Without wishing to be bound by theory, the presence in the taglienone compounds of an alpha-beta unsaturated ketone moiety, susceptible to nucleophilic substitution by reactive protein thiols, parallels the reactive structure and potentially the pharmacological activities of ethacrynic acid. The latter compound inhibits glutathione transferase and other thiol-sensitive proteins, potentiates anticancer agents such as ionising radiation due to depletion of thiol content, and is used clinically as a diuretic. Ethacrynic acid also inhibits the pro-inflammatory NF-kappa B signalling pathway, including inhibition of the secretion of the pro-inflammatory mediators IL-6, IL-10, nitric oxide, and HMGB1 from macrophages (Killeen et al., J. Pharmacol. Exp. Ther., 2006, 316:1070-9).

The compounds of the invention are a preferred structural class because many variations in structure of the hydrophobic tail may confer potential for a range of bioactivities depending on the microenvironment of the protein binding site. For example, ethacrynic acid required a 10-fold higher concentration than EBI-23 to achieve cell arrest, and showed no selectivity against tumor cells.

In yet another aspect of the invention, there is provided a method of diuresis comprising administering to a subject, a compound according to the invention or a pharmaceutically acceptable salt thereof.

Use of a compound of the invention or a pharmaceutically acceptable salt thereof in the manufacture of a diuretic medicament.

The term "subject" as used herein includes humans, primates, livestock animals (e.g., sheep, pigs, cattle, horses, donkeys), laboratory test animals (e.g., mice, rabbits, rats, guinea pigs), companion animals (e.g., dogs, cats), birds (e.g., chickens, ducks, geese, parrots, cockatoos, pigeons, finches, raptors, ratites, quail, canaries), captive wild animals (e.g., foxes, kangaroos, deer) and reptiles (e.g., lizards and snakes). Preferably, the subject is human, a companion animal, a livestock animal or a laboratory test animal. Even more preferably, the subject is a human, a companion animal or livestock animal.

An "effective amount" means an amount necessary at least partly to attain the desired response, or to delay the onset or inhibit progression or halt altogether, the onset or progression of a particular condition being treated. The amount varies depending upon the health and physical condition of the individual to be treated, the taxonomic group of individual to be treated, the degree of protection desired, the formulation of the composition, the assessment of the medical situation, and other relevant factors. It is expected that the amount will fall in a relatively broad range that can be determined through routine trials. An effective amount in relation to a human patient, for example, may lie in the range of about 0.1 ng per kg of body weight to 1 g per kg of body weight per dosage. The dosage is preferably in the range of 1 µg to 1 g per kg of body weight per dosage, such as is in the range of 1 mg to 1 g per kg of body weight per dosage. In one embodiment, the dosage is in the range of 1 mg to 500 mg per kg of body weight per dosage. In another embodiment, the dosage is in the range of 1 mg to 250 mg per kg of body weight per dosage. In yet another embodiment, the dosage is in the range of 1 mg to 100 mg per kg of body weight per dosage, such as up to 50 mg per kg of body weight per dosage. In yet another embodiment, the dosage is in the range of 1 µg to 1 mg per kg of body weight per dosage. Dosage regimes may be adjusted to provide the optimum therapeutic response. For example, several divided doses may be administered daily, weekly, monthly or other suitable time intervals, or the dose may be proportionally reduced as indicated by the exigencies of the situation.

Reference herein to "treatment" and "prophylaxis" is to be considered in its broadest context. The term "treatment" does not necessarily imply that a subject is treated until total recovery. Similarly, "prophylaxis" does not necessarily mean that the subject will not eventually contract a disease condition. Accordingly, treatment and prophylaxis include amelioration of the symptoms of a particular condition or preventing or otherwise reducing the risk of developing a particular condition. The term "prophylaxis" may be considered as reducing the severity or onset of a particular condition. "Treatment" may also reduce the severity of an existing condition.

In another aspect of the invention, the compounds of the invention are suitable for use as a pesticide. The invention therefore further provides a pesticidal composition comprising a compound of the invention or a pharmaceutically, an agriculturally or pesticidally acceptable salt thereof and a pharmaceutically, an agriculturally or pesticidally acceptable carrier.

The pesticidal composition may be in the form of an emulsifiable concentrate, a flowable, a wettable powder, a soluble powder, a solution, an aerosol, a dust, a granule or a bait. A person skilled in the formulation of pesticidal compositions would be able to prepare such formulations.

Suitable carriers for pesticidal compositions include, but are not limited to, oils, especially petroleum oils, emulsifiers, solvents such as water or hydrocarbons, surfactants, aerosol spray components such as CFCs, talc or clay.

In yet another aspect of the invention, there is provided a method of controlling pests comprising applying an effective amount of a compound of the invention or a pharmaceutically, an agriculturally or pesticidally acceptable salt thereof to a subject and/or an agricultural or other environment infested with the pest.

The pest is preferably an insect, especially flies, beetles, grasshoppers, locusts, butterflies and moths and their larvae or nymphs, especially the flies (*Diptera*) such as true flies, fleas, lice, ticks, mosquitoes, gnats and midges.

In some embodiments, the pest infests plants. Examples of such pests include, but are not limited to, *Acyrthosiphon kondoi* (blue-green aphid), *Acyrthosiphon pisum* (pea aphid), *Agrotis* spp. (cutworm), *Agrypnus variabilis* (sugarcane wireworm), *Anoplognathus* spp. (christmas beetles), *Aphodius tasmaniae* (blackheaded pasture cockchafer), *Austroasca alfalfae* (lucerne leaf hopper), *Bathytricha truncate* (sugarcane and maize stemborer), *Bemisia tabaci* (whitefly), *Brachycaudus helichrysi* (leaf curl plum aphid), *Brevicoryne brassicae* (cabbage aphid), *Bruchophagus roddi* (lucerne seed wasp), *Bruchus pisorum* (pea weevil), *Bryobia* spp. (bryobia mite), *Clampa arietaria* (brown pasture looper), *Chortoicetes terminifera* (Australian plague locust), *Chrysodeitis angentifena* (tobacco looper), *Chrysodeitis eriosoma* (green looper), *Contarinia sorghicola* (sorghum midge), *Deroceras* spp. (slugs), *Diachrysia oricalcea* (soybean looper), *Etiella behrii* (lucerne seed-web moth), *Frankliniella schultzei* (tomato thrips), *Graphognathus leucoloma* (white fringed weevil), *Halotydeus destructor* (redlegged earth mite), *Hednota pedionoma* (pasture webworm), *Helicoverpa armigera* (corn earworm), *Helicoverpa punctigera* (native budworm), *Helix* spp. (snails), *Heteronychus arator* (African black beetle), *Leucania convecta* (common armyworm), *Lipaphis erysimi* (turnip aphid), *Listroderes difficilis* (vegetable weevil), *Melanacanthus scutellaris* (brown bean bug), *Merophyas divulsana* (lucerne leaf roller), *Myzus persicae* (green peach aphid), *Nala lividipes* (black field earwig), *Mythimna convector* (common armyworm), *Nezara viridula* (green vegetable bug), *Nysius vinitor* (rutherglen bug), *Nysius clevelandensis* (grey cluster bug), *Oncopera rufobrunnea* (underground grass grub), *Orondina* spp. (false wireworm), *Othnonius batesi* (black soil scarabs), *Penthaleus major* (blue oat mite), *Persectania ewingii* (southern armyworm), *Petrobia lateens* (brown wheat mite), *Pieris rapae* (cabbage white butterfly), *Piezodorus hybneri* (redbanded shield bug), *Plutella xylostella* (cabbage moth/diamondback moth), *Rhopalosiphum maidis* (corn aphid), *Sericesthis* spp. (small brownish cockchafers), *Sitona discoideus* (sitona weevil), *Sminthurus viridis* (lucerne flea), *Spodoptera exigua* (lesser armyworm), *Spodoptera letura* (cluster caterpillar *Spodoptera mauritia* (lawn armyworm), *Stomopteryx simplexella* (soybean moth), *Tetranychus ludeni* (bean spider mite), *Tetranychus urticae* (two spotted mite), *Therioaphis trifolii f. maculata* (spotted alfalfa aphid), *Thrips tabaci* (onion thrips), *Thrips imaginis* (plague thrips), *Zizina labradus* (grass blue butterfly), *Zygrita diva* (lucerne crown borer).

In other embodiments, the pests infest subject and/or environments other than plants. Examples of such pests include, but are not limited to, lice, ants including *Camponotus* spp., *Lasius alienus, Acanthomyops interjectus, Monomorium pharaonis, Solenopsis molesta, Tetramorium caepitum, Monomorium minimum, Prenolepis impairs, Formica exsectoides, Iridomyrmex pruinosus, Cremastogaster lineolata, Tapinoma sessile, Paratrechina longicornis*, cockroaches, mosquitos, bed bugs including *Leptoglassus occidentalis, Acrosternum hiare, Chlorochroa sayi, Podius maculiventris, Murgantia histrionica, Oncopeltus fasciatus, Nabis alternatus, Leptopterna dolabrata, Lygus lineolaris, Adelpocoris rapidus, Poecilocapsus lineatus, Orius insidiosus, Corythucha ciliata*, bees, wasps, black widow spider, booklice, boxelder bug, brown recluse spider, clothes moths including *Tineola* spp., *Tinea* spp., *Trichophaga* spp., carpet beetles, centipedes, clover mites, cluster and face flies, cigarette and drugstore beetles, crickets including *Acheta* spp., *Gryllus* spp., *Gryllus* spp., *Nemobius* spp., *Oecanthus* spp., *Ceuthophilus* spp., *Neocurfilla* spp., daddy-long-legs, domestic flies, drain flies, earwigs, European hornet, fleas including *Ctenocephalides felis, Ctenocephalides canis, Ctenocephalides* spp., *Nosopsyllus fasciatus, Nosopsyllus* spp., *Xenopsylla cheopis, Xenopsylla* spp., *Cediopsylla simplex, Cediopsylla* spp., fungus gnats, ground beetles, hide and larder beetles, horse/cattle/deer/pig flies, house dust mites including *Dermatophagoides farinae, Dermatophagoides pteronyssinus, Dermatophagoides* spp., mites including *Ornithonyssus sylviarum, Dermanyssus gallinae, Ornithonyssus bacoti, Liponyssoides sanuineus, Demodex folliculorum, Sarcoptes scabiei hominis, Pyemotes tritici, Acarus siro, Tyrophagus putrescentiae, Dermatophagoides* sp., human lice, humbacked flies, Indian meal moth, millipedes, mud daubers, multicolored asian lady beetle, house borer, midges and crane flies, periodical and "dog-day" cicadas, powderpost beetles, roundheaded and flatheaded borers, pseudoscorpions, psyllids or jumping plant lice, spider beetles, sac spiders, sap beetles, termites, silverfish and firebrats, sowbugs and pillbugs, springtails, stinging hair caterpillars, tarantulas, vinegar flies, wasps and hornets, wharf borer, woods cockroach, yellowjacket wasps, fungus beetles, seed weevils, sawtoothed and merchant grain beetles, confused and red flour beetles, granery and rice weevils, indian meal moth, mealworms, drain flies, ticks including *Dermacentar* spp., *Ixodes* spp., *Rhipicenphalus* spp., carpenter bees, fleas, assassin bugs, human lice, chiggers, mystery bugs, european hornet, stinging hair caterpillars, black-legged tick, mayflies, black flies, horsehair worms, crickets, gypsy moths, grasshoppers, gnats, midges, locusts, mosquitoes including *Aedes albopictus, Aedes Canadensis Aedes triseriatus, Aedes tivittatus, Aedes vexans, Aedes* spp., *Anopheles quadrimaculatus, Anopheles* spp., *Coquillettidia perturbans, Coquillettidia* spp., *Culex pipiens, Culex* spp.

An agriculturally effective amount may be determined by those skilled in the art using known methods and would typically range from 5 g to 500 g per hectare.

The environment that is infested with a pest may be an agricultural environment, a household environment or an industrial environment.

As used herein, the term "agricultural environment" refers to an environment in which agriculture is carried out, for example, the growing of crops, trees, and other plants of commercial importance. The agricultural environment includes not only the plant itself, but also the soil and area around the plants as they grow and also areas where parts of plants, for example, seeds, grains, leaves or fruit, may be stored.

A "household environment" includes environments that are inhabited by humans or animals and may include indoor environments such as carpets, curtains, cupboards, bedding and the air inside a house. An "industrial environment" includes environments which are used for industrial purposes such as manufacture, storage or vending of products. Industrial environments include warehouses, manufacturing plants, shops, storage facilities and the like.

In this aspect, preferred compounds of the invention include EBI-24 and EBI-25.

The invention further provides use of a compound of the invention as an agrochemical.

Accordingly, the compound of the invention may be formulated in an appropriate manner for delivery to crops, pastures, forests and other agricultural environments, preferably for the alleviation and/or eradication of one or more insect pests.

DETAILED DESCRIPTION

Activity Screening

Figure 1:
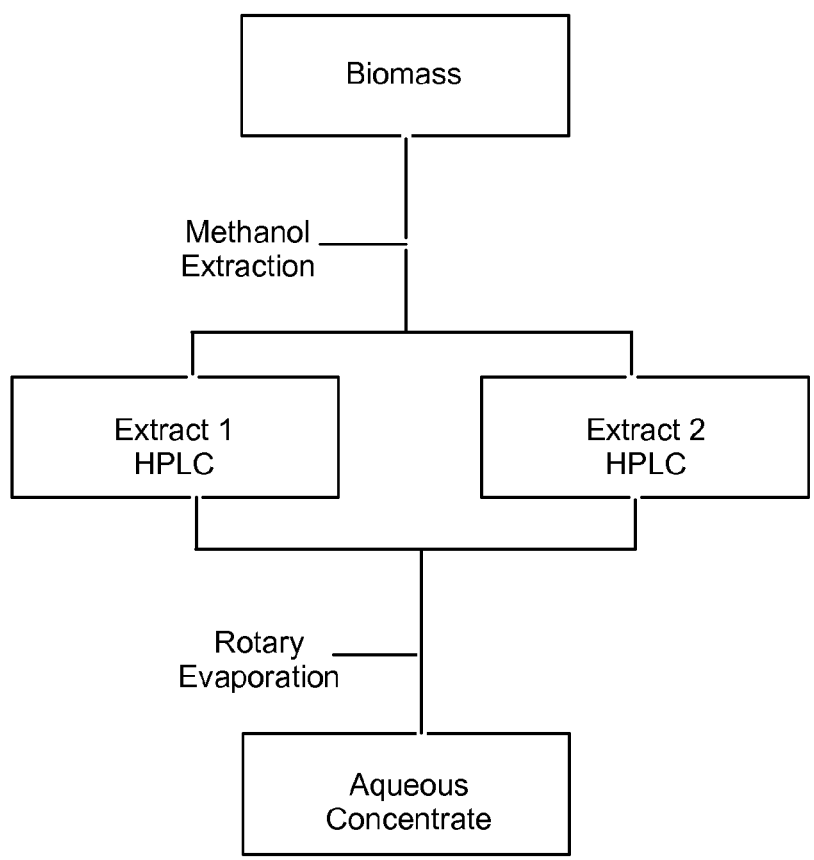
FIG. 1: Flowchart for initial solvent extraction of compounds of formula

Solvent extraction samples from *Litsea leefeana* (epicarp and mesocarp), *Cinnamomum laubatii* (seed) and *Cryptocarya lividula* (epicarp and mesocarp) containing compounds of formula (I) and formula (II) were tested to determine therapeutic activity by screening in a range of Microbial Screening Technologies bioassays, notably NemaTOX, ProTOX, MycoTOX, CyTOX, DipteraTOX and TriTOX. For ease of description these bioassays will be described briefly prior to the extraction and chemical structure elucidation methodologies.

NemaTOX (alternatively referred to herein as Ne) is an anthelmintic bioassay, applicable to all parasitic nematodes with free-living life cycle stages, and can be used as a screen to detect activity and define the species spectrum of compounds against parasitic nematodes and examine the impact of pre-existing resistance to other anthelmintic classes on potency. *Haemonchus contortus* was utilised for this assay.

The effect on larval development is determined in this assay by the method described by Gill et al. (1995) *Int. J. Parasitol.* 25: 463-470. Briefly, in this assay nematode eggs were applied to the surface of an agar matrix containing the test sample and allowed to develop through to the L3, infective stage (6 days). At this time the stage of larval development reached and any unusual features (deformity, paralysis, toxicity) were noted by microscopic examination.

ProTOX, (alternatively referred to herein as Bs) is an antibacterial bioassay, broadly applicable to most aerobic and anaerobic bacteria. The bioassay features a solid phase agar base into which the test compound has been incorporated together with a chromogen. As the bacteria multiply in the well, the chromogen is metabolised from blue in a two-step process to a colourless compound. Compounds with potent bactericidal activity inhibit bacterial metabolism of the chromogen while bacteriostatic compounds induce limited metabolism as indicated by an intermediate pink colour. ProTOX is broadly applicable to a range of gram-positive and gram-negative bacteria under aerobic and microaerophilic conditions. ProTOX assays were carried out using *Bacillus subtilis*.

Briefly, in ProTOX, the bacteria (24 hour broth) were applied to the surface of an agar matrix containing the test sample and allowed to grow for 48 h. The assay was monitored at 24 and 48 hours and the active wells noted. Known antibiotics yield consistent colour transitions which are concentration and time dependent. These patterns provided an important guide to the early recognition of interesting characteristics. Generally bactericidal actives give no colour change at both 24 and 48 hours while bacteriostatic actives are active at 24 hours but less potent or inactive at 48 hours.

MycoTOX (alternatively referred to herein as Tr) is a non-chromogenic bioassay used to detect activity against filamentous fungal pathogens of plants and animals. The bioassay features a solid phase agar base into which the test compound has been incorporated. As the growth patterns of filamentous fungi are readily apparent on the agar surface the extent of mycelial growth, sporulation (if relevant to the species under investigation) and colour changes with maturation are measured. Compounds with potent antifungal activity inhibit germination of fungal spores and provide a stark contrast to wells containing inactive compounds with the excessive fungal growth. Lower concentrations of such compounds, or compounds exhibiting a more fungistatic mode of action, show reductions in mycelial growth, extent of sporulation or reductions in other characteristic patterns of colony maturation.

MycoTOX, involves a fungus (spore suspension or mycelial fragments) applied to the surface of an agar matrix containing the test chemical and allowed to grow for a period of up to a week (depending on species). The assay was monitored at two discrete times to identify key development phases in the life cycle (for example mycelial growth and extent of sporulation) and the active wells noted. The monitoring times were dependent on the fungal species under investigation.

The MycoTOX assays were carried out using *Trichophyton rubrum*.

CyTOX (alternatively referred to herein as Cy) is a microtitre plate bioassay use to identify potential antitumor actives. CyTOX is a chromogenic bioassay with broad application to a wide range of tumor and non-tumor cell lines. The colour transitions in CyTOX are proportional to cell metabolism and turnover and hence offer useful recognition patterns to support the diagnostic classification of actives within a framework of known cytotoxic and antitumor actives.

CyTOX features a liquid media into which the test compound has been incorporated together with a novel chromogen. As the cells grow and divide the chromogen is metabolised from purple in a single step process to a colourless metabolite. CyTOX is routinely undertaken using NS1 murine myeloma cell line as a guide to mammalian cell toxicity.

Briefly, in CyTOX the cells were applied to the media containing the test chemical and allowed to grow for 72 hours. The assay was monitored at 24, 48 and 72 hours and the active wells identified.

DipteraTOX. DipteraTOX is referred to herein as DipG, DipP and DipH. DipG represents no grazing of larva. DipP represents no pupae formation and Dip H represents no hatching of flies. A value of A in DipG, Dip P or Dip H represents very active and a value of P represents active. In DipteraTox the fly eggs are applied to the surface of an agar matrix containing 250 µg per mL of the test chemical and allowed to hatch, develop and pupate for a period up of two weeks. The assay was monitored at two discrete times to determine the extent of grazing of the agar matrix at Week 1 and the presence of adult flies at Week 2. Activity was scored qualitatively as active or inactive at Days 7 and 14 to denote failure to feed and failure to development to the adult stage, respectively. *Drosophila melanogaster* was utilised for this assay.

TriTOX (alternatively referred to herein as Gi) is a microtitre plate based chromogenic bioassay for the screening of anti-protozoan activity of pathogenic, anaerobic/microaerophilic protozoans for example *Giardia* spp. and *Trichomonas* spp. The bioassays are run under anaerobic conditions and features species specific chromogens. The minimum inhibitory concentrations (approximate LD99) are determined by the following method: stock solutions of the unknowns are serially diluted 1/2 to give 12 concentrations over a 2,048-fold range. Aliquots of each concentration(s) are applied to the wells of 96-well microtitre plates and diluted with media. Test substances are scored as active or inactive based on the chromogen colour change. The lowest concentration at which the compound is active is noted as the minimum inhibitory concentration (MIC). Additionally, microscopic inspection is carried out to identify any patterns of morphological change that may be consistent with a type of toxicity and therefore mode of action. *Giardia* spp. was utilized for this assay.

In order that the invention may be readily understood and put into practical effect, particular preferred embodiments will now be described by way of the following non-limiting examples.

Example 1

Methods
Extraction

Biomass samples, including seeds, leaves and bark, from *Litsea leefeana* (epicarp and mesocarp), *Cinnamomum laubatii* (seed) and *Cryptocarya lividula* (epicarp and mesocarp) where collected and subject to the following extraction process. These samples and their subsequent fractions are referred in the below examples as EB116, EB115 and EB 77 for samples and subsequent fractions from *Litsea leefeana*, *Cinnamomum laubatii* and *Cryptocarya lividula* respectively.

Phase 1—Extraction

The biomass was generously covered with methanol and shaken (~2 L, overnight) followed by filtration to give the first extract. This process was repeated a second time (~2 L, ~5 hours) to generate the second extract. Each extract was examined by analytical HPLC and bioassayed (FIG. 1). The sequential methanol extracts are combined and the solvent removed by rotary evaporation to afford an aqueous concentrate.

Phase 2—Solvent Partition

Figure 2A:
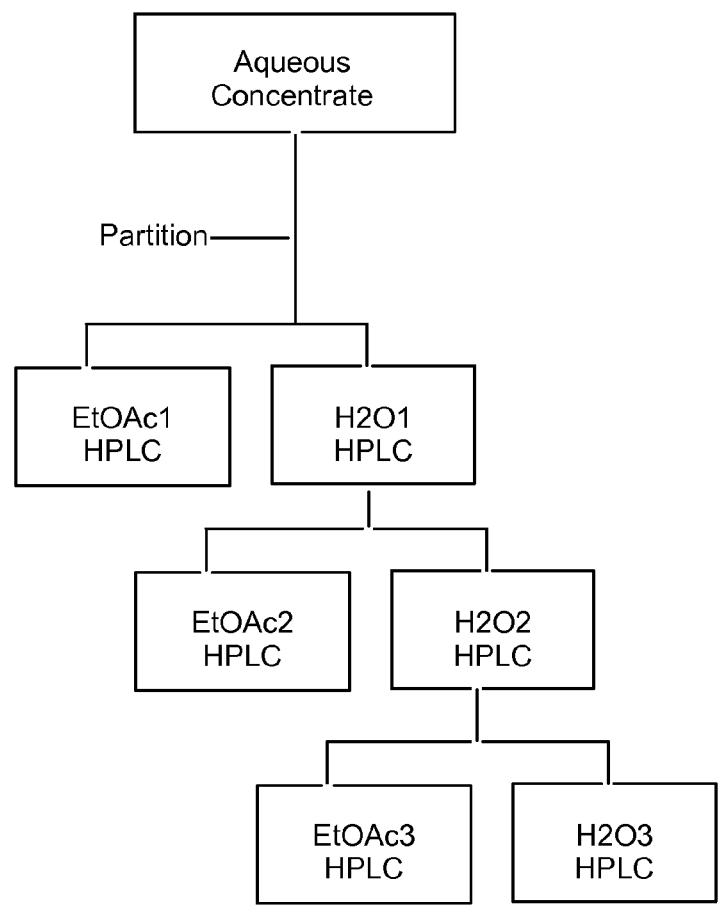
FIG. 2A: Flowchart showing the solvent partition for the aqueous concentrate obtained from FIG. 1.

The aqueous concentrate from the extraction was diluted with water to 400 mL. The diluted sample (code 'Cr') was subsampled for HPLC and bioassay, then shaken with an equal volume of ethyl acetate (EtOAc) in a reparatory funnel and the individual layers, EtOAc1 and H2O1, collected. Note, occasionally a precipitate would form that was insoluble in either layer. This precipitate was collected by filtration and dissolved in methanol (code 'Me'). The lower aqueous layer (H2O1) was twice more extracted with ethyl acetate to give EtOAc2 and EtOAc3 along with the remaining H2O3 layer. Subsamples of all layers were examined by analytical HPLC and bioassay (FIG. 2A).

Figure 2B:
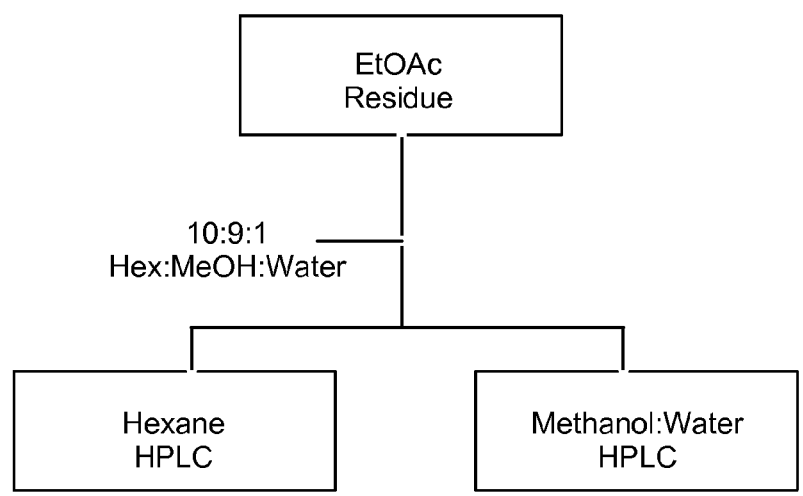
FIG. 2B: Flowchart showing the solvent partition for the ethyl acetate residue obtained from FIG. 1.

The sequential ethyl acetate extracts were pooled and the solvent removed by rotary evaporation to afford a residue that is weighed. On occasions, analytical HPLC indicated the EtOAc extract contained considerable amounts of extremely lipophilic (RT>9 minutes) material. To remove this material a 10:9:1-hexane:methanol:water partition was performed (FIG. 2B).

Phase 3—Preparative HPLC Fractionation

Figure 3:
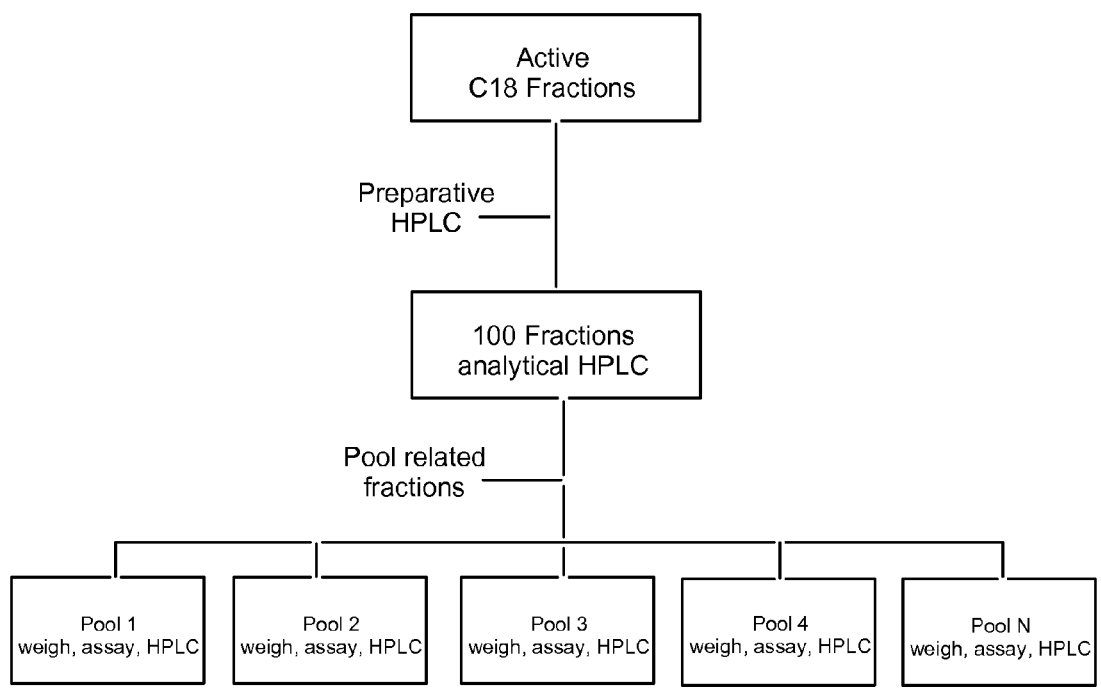
FIG. 3: Flowchart showing the steps in preparative HPLC chromatography.

The residue from the solvent partition was investigated by analytical HPLC to find optimum chromatographic conditions for separation of the metabolites present. Using these optimum conditions the residue (~2 g) was fractionated by preparative reverse phase HPLC (C18, single injection) into 100 fractions (FIG. 3). Subsamples of all 100 fractions are examined by analytical HPLC. After analysis of the HPLC traces, the 100 fractions were consolidated into 20 to 30 pooled fractions (pools), some of which may be >80% pure. These pooled fractions were weighed, bioassayed and examined by analytical HPLC.

Solvent Partition Summary for EB116, EB115 and EB 77

Biomass samples of *Litsea leefeana* (EB116), *Cinnamomum laubatii* (EB115), and *Cryptocarya lividula* (EB77) under went extraction and solvent partitioning, using phase 1 and 2 described above. Table 1 summarises the amounts of extractable material obtained after solvent partitioning with ethyl acetate.

TABLE 1

Weights after Ethyl Acetate Partition of Extracts

| Sample | Weight[1] | EtOAc[2] | % Ext.[3] | HPLC Comment |
|---|---|---|---|---|
| EB116 | 780 | 32.8 | 4.2 | Very complex[#] |
| EB115 | 902 | 39.6 | 4.4 | Good[%] |
| EB77 | 416 | 11.4 | 2.7 | Excellent |

[1]Weight: Total sample weight in grams of plant material supplied and used for the study.
[2]EtOAc: Ethyl acetate extractables.
[3]% Ext.: Ethyl acetate extractables expressed as a percentage of the total sample weight.
[#]0.6 g of material precipitation during ethyl acetate extraction.
[%]31.6 g of material precipitation during ethyl acetate extraction.

Preparative HPLC

The preparative HPLC was carried out on a system consisting of two Shimadzu LC-8A Preparative Liquid Chromatographs with static mixer, Shimadzu SPD-M10AVP Diode Array Detector and Shimadzu SCL-10AVP System Controller. The column used was 50×100 mm (diameter× length) packed with C18 Platinum EPS (Alltech).

Approximately 2 grams of ethyl acetate extracted material was dissolved in dimethyl sulphoxide (4 mL) and subjected to preparative HPLC with typically conditions being 60 mL/minute with gradient elution of 30% to 100% acetonitrile/water over 20 minutes followed by acetonitrile for 10 minutes. One hundred fractions (20 mL) were collected, evaporated under nitrogen, and then combined on the basis of HPLC analysis.

UV Analysis

UV spectra were acquired during HPLC with the Shimadzu SPD-M10AVP Diode Array Detector as mentioned above.

NMR Analysis

All NMR spectra were acquired in d6-dimethyl sulphoxide and referenced to the residual dimethyl sulphoxide signals or deuterated chloroform ($CDCl_3$) and referenced to residual chloroform signals. 1D NMR spectra, $^1H$ and $^{13}C$ [APT], were acquired at 300 and 75 MHz respectively on a Varian Gemini 300BB (Palo Alto C.A. USA) spectrometer. 2D NMR spectra, HSQC, HMBC, COSY and TOCSY, and a 1D NMR $^1H$ spectrum were acquired on a Bruker DRX600 (600 MHz) NMR spectrometer.

Analysis of NMR data was performed using ACD/SpecManager and ACD/Structure Elucidator, both version 6.0 from Advanced Chemistry Development, Inc. (Toronto, ON, Canada).

Electrospray Mass Spectrometry Analysis (ES-MS)

All positive electrospray mass spectra were performed on a Finnigan/Mat TSQ7000 LCMS/MS (San Jose C.A. USA).

Example 2

EB116: Extraction and Solvent Partition

Extraction and solvent partitioning of EB116 afforded 780 g of material. Each of the extraction and solvent partition layers were tested for bioactivity using the above bioassays. It can be seen from Table 2 that the extracts and ethyl acetate layers of the solvent partition all contain high Ne, Bs, Tr and Cy activity.

TABLE 2

Activity of Extracts and Solvent Partitions.

| Sample | Ne[4] | Bs[4] | Tr[4] | Cy[4] |
|---|---|---|---|---|
| EB116.PY1.7-Ext1 | 4 | 64 | 2 | 256 |
| EB116.PY1.7-Ext2 | 16 | 128 | 8 | 1024 |
| EB116.PY1.19-Cr | 0 | 0 | 0 | 8 |
| EB116.PY1.19-EtOAc1 | 64 | 2048 | 16 | 2048 |
| EB116.PY1.19-EtOAc2 | 32 | 128 | 8 | 2048 |
| EB116.PY1.19-EtOAc3 | 1 | 2 | 1 | 64 |
| EB116.PY1.19-H2O1 | 1 | 0 | 2 | 16 |
| EB116.PY1.19-H2O2 | 0 | 0 | 0 | 4 |
| EB116.PY1.19-H2O3 | 0 | 1 | 0 | 8 |
| EB116.PY1.19-Me | 0 | 0 | 0 | 0 |

[4]$LD_{99}$ in µg/mL calculated as weight of chemical in last well with activity, however the real value may be lower as end point not attained.

The successive aqueous concentrated extracts were subjected to HPLC. The column used was 50×100 mm (diameter×length) packed with C18 Platinum EPS (Alltech). Approximately 2 grams of extracted material was dissolved in dimethyl sulphoxide (4 mL) and subjected to preparative HPLC with typical conditions being 60 mL/minute with gradient elution of 30% to 100% acetonitrile/water over 20 minutes followed by acetonitrile for 10 minutes.

For comparison purposes the first ethyl acetate partition and the third water layers were analysed by HPLC. There were little or no compounds of interest remaining in the third water layer of the third water/ethyl acetate solvent partition.

EB116: Preparative HPLC Fractionation

In a manner similar to that described in Phase 3 above the EB116 ethyl acetate solvent partition samples where pooled and further worked up using preparative HPLC chromatograph.

The preparative HPLC was used to produce 100 fractions. These fractions were pooled depending on the relative concentration of compounds indicated in the preparative HPLC chromatograph.

The bioactivity of each fraction or pooled fraction resulting from the preparative HPLC was determined using the above bioassay method. The results are summarised below at Table 3.

TABLE 3

Activity of Preparative HPLC Pools.

| Sample | Weight[5] | Ne[4] | Bs[4] | Tr[4] | Cy[4] |
|---|---|---|---|---|---|
| EB116.LA2.139-1/12 | 64 | 1 | 0 | 0 | 4 |
| EB116.LA2.139-13/14 | 15 | 0 | 0 | 0 | 4 |
| EB116.LA2.139-15/16 | 22 | 0 | 0 | 2 | 8 |
| EB116.LA2.139-17/21 | 19 | 0 | 0 | 0 | 4 |
| EB116.LA2.139-22/26 | 21 | 0 | 0 | 0 | 16 |
| EB116.LA2.139-27/31 | 37 | 1 | 0 | 0 | 32 |
| EB116.LA2.139-32/33 | 29 | 4 | 2 | 0 | 256 |
| EB116.LA2.139-34/35 | 29 | 1 | 1 | 0 | 32 |
| EB116.LA2.139-36 | 1022 | 1 | 4 | 2 | 32 |
| EB116.LA2.139-37 | 27 | 2 | 8 | 2 | 64 |
| EB116.LA2.139-38/40 | 70 | 16 | 32 | 32 | 256 |
| EB116.LA2.139-41/45 | 205 | 32 | 1024 | 32 | 1024 |
| EB116.LA2.139-46/47 | 74 | 16 | 256 | 32 | 1024 |
| EB116.LA2.139-48/50 | 146 | 16 | 126 | 64 | 512 |
| EB116.LA2.139-51/56 | 287 | 64 | 2048 | 32 | 2048 |
| EB116.LA2.139-57/58 | 120 | 16 | 512 | 8 | 2048 |
| EB116.LA2.139-59/63 | 370 | 16 | 2048 | 4 | 2048 |
| EB116.LA2.139-64/70 | 102 | 8 | 128 | 0 | 2048 |
| EB116.LA2.139-71/80 | 53 | 0 | 2 | 0 | 2048 |
| EB116.LA2.139-81/90 | 17 | 0 | 0 | 0 | 32 |
| EB116.LA2.139-91/100 | 55 | 1 | 0 | 0 | 128 |

[4]$LD_{99}$ in µg/mL calculated as weight of chemical in last well with activity; however, the real value may be lower as end point not attained.
[5]Weight in mg.

EB115: Extraction and Solvent Partition

Extraction and solvent partitioning of EB115 afforded 902 g of material. Each of the extraction and solvent partition layers were tested for bioactivity using the above bioassays. It can be seen from Table 4 that the extracts and ethyl acetate layers of the solvent partition all contain high Ne, Bs, Tr and Cy activity.

TABLE 4

Activity of Extracts and Solvent Partitions.

| Sample | Ne[4] | Bs[4] | Tr[4] | Cy[4] |
|---|---|---|---|---|
| EB115.PY1.6-Ext1 | 8 | 16 | 128 | 256 |
| EB115.PY1.6-Ext2 | 8 | 16 | 128 | 256 |
| EB115.PY1.18-Cr | 1 | 0 | 4 | 8 |
| EB115.PY1.18-EtOAc1 | 16 | 128 | 256 | 1024 |
| EB115.PY1.18-EtOAc2 | 8 | 8 | 64 | 128 |
| EB115.PY1.18-EtOAc3 | 0 | 0 | 8 | 8 |
| EB115.PY1.18-H2O3 | 1 | 0 | 4 | 8 |
| EB115.PY1.18-Me | 0 | 0 | 1 | 8 |

[4]$LD_{99}$ µg/mL calculated as weight of chemical in last well with activity, however the real value may be lower as end point not attained.

The successive aqueous concentrated extracts were subjected to HPLC. The column used was 50×100 mm (diameter×length) packed with C18 Platinum EPS (Alltech). Approximately 2 grams of extracted material was dissolved in dimethyl sulphoxide (4 mL) and subjected to preparative HPLC with typical conditions being 60 mL/minute with gradient elution of 30% to 100% acetonitrile/water over 20 minutes followed by acetonitrile for 10 minutes.

For comparison purposes the first ethyl acetate partition and the third water layers were analysed by HPLC. There were little or no compounds of interest remaining in the third water layer of the third water/ethyl acetate solvent partition.

EB115: Preparative HPLC Fractionation

In a manner similar to that described in Phase 3 above the EB115 ethyl acetate solvent partition samples where pooled and further worked up using preparative HPLC chromatograph.

The preparative HPLC was used to produce 100 fractions. These fractions were pooled depending on the relative concentration of compounds indicated in the preparative HPLC chromatograph.

The bioactivity of each fraction or pooled fraction resulting from the preparative HPLC was determined using the above bioassay method. The results are summarised below at Table 5.

TABLE 5

Activity of Preparative HPLC Pools.

| Sample | Weight[5] | Ne[4] | Bs[4] | Tr[4] | Cy[4] |
|---|---|---|---|---|---|
| EB115.LA2.138-1/13 | 44 | 1 | 0 | 8 | 4 |
| EB115.LA2.138-14/21 | 9 | 0 | 0 | 0 | 0 |
| EB115.LA2.138-22 | 2 | 0 | 0 | 0 | 0 |
| EB115.LA2.138-23/28 | 12 | 0 | 0 | 0 | 2 |
| EB115.LA2.138-29/33 | 29 | 0 | 0 | 4 | 16 |
| EB115.LA2.138-34/36 | 22 | 0 | 0 | 4 | 16 |
| EB115.LA2.138-37 | 45 | 1 | 0 | 16 | 32 |
| EB115.LA2.138-38 | 151 | 4 | 8 | 32 | 512 |
| EB115.LA2.138-39 | 88 | 0 | 2 | 32 | 512 |
| EB115.LA2.138-40 | 70 | 4 | 4 | 32 | 256 |
| EB115.LA2.138-41 | 64 | 0 | 16 | 64 | 512 |
| EB115.LA2.138-42 | 56 | 0 | 8 | 32 | 256 |
| EB115.LA2.138-43 | 10 | 0 | 8 | 0 | 64 |
| EB115.LA2.138-44/47 | 137 | 4 | 16 | 128 | 128 |
| EB115.LA2.138-48/49 | 185 | 4 | 32 | 1024 | 128 |
| EB115.LA2.138-50/52 | 148 | 16 | 16 | 1024 | 512 |
| EB115.LA2.138-53/56 | 48 | 8 | 128 | 128 | 1024 |
| EB115.LA2.138-57/60 | 130 | 0 | 32 | 32 | 1024 |
| EB115.LA2.138-61/65 | 130 | 4 | 256 | 64 | 2048 |
| EB115.LA2.138-66/70 | 16 | 2 | 32 | 0 | 128 |
| EB115.LA2.138-71/80 | 16 | 0 | 2 | 0 | 128 |
| EB115.LA2.138-81/90 | 5 | 0 | 0 | 0 | 4 |
| EB115.LA2.138-91/100 | 12 | 0 | 0 | 0 | 8 |

[4]$LD_{99}$ in μg/mL calculated as weight of chemical in last well with activity, however the real value may be lower as end point not attained.
[5]Weight in mg.

EB77: Extraction and Solvent Partition

Extraction and solvent partitioning of EB77 afforded 416 g of material. Each of the extraction and solvent partition layers were tested for bioactivity using the above bioassays. It can be seen from Table 6 that the extracts and ethyl acetate layers of the solvent partition all contain high Ne, Bs, Tr and Cy activity.

TABLE 6

Activity of Extracts and Solvent Partitions.

| | Ne | | Bs | | Tr | | Cy | |
|---|---|---|---|---|---|---|---|---|
| Sample | Titre | $LD_{99}$[4] | Titre | $LD_{99}$[4] | Titre | $LD_{99}$[4] | Titre | $LD_{99}$[4] |
| EB77.MG1.41-Ext1 | 4 | 440 | 64 | 27 | 16 | 110 | 256 | 6.8 |
| EB77.MG1.41-Ext2 | 2 | 340 | 32 | 21 | 16 | 43 | 128 | 5.3 |
| EB77.MG1.57-EtOAc1 | 64 | 140 | 512 | 17 | 256 | 34 | 2048 | 4.3 |
| EB77.MG1.57-EtOAc2 | 1 | 250 | 4 | 62 | 4 | 62 | 32 | 7.7 |
| EB77.MG1.57-EtOAc3 | 0 | | 1 | 110 | 2 | 55 | 8 | 14 |
| EB77.MG1.57-H2O1 | 1 | 4200 | 0 | | 2 | 2100 | 8 | 530 |
| EB77.MG1.57-H2O2 | 1 | 4200 | 0 | | 2 | 2100 | 8 | 530 |
| EB77.MG1.57-H2O3 | 1 | 4300 | 0 | | 0 | | 8 | 530 |

[4]$LD_{99}$ in μg/mL calculated as weight of chemical in last well with activity; however, the real value may be lower as end point not attained.

The successive aqueous concentrated extracts were subjected to HPLC. The column used was 50×100 mm (diameter×length) packed with C18 Platinum EPS (Alltech). Approximately 2 grams of extracted material was dissolved in dimethyl sulphoxide (4 mL) and subjected to preparative HPLC with typical conditions being 60 mL/minute with gradient elution of 30% to 100% acetonitrile/water over 20 minutes followed by acetonitrile for 10 minutes.

For comparison purposes the first ethyl acetate partition and the third water layers were analysed by HPLC. There were little or no compounds of interest remaining in the third water layer of the third water/ethyl acetate solvent partition.

EB77: Preparative HPLC Fractionation

In a manner similar to that described in Phase 3 above the EB77 ethyl acetate solvent partition samples where pooled and further worked up using preparative HPLC chromatograph.

The preparative HPLC was used to produce 100 fractions. These fractions were pooled depending on the relative concentration of compounds indicated in the preparative HPLC chromatograph.

The bioactivity of each fraction or pooled fraction resulting from the preparative HPLC was determined using the above bioassay method. The results are summarised below at Table 7.

TABLE 7

Activity of Preparative HPLC Pools.

| | | Ne | | Bs | | Tr | | Cy | |
|---|---|---|---|---|---|---|---|---|---|
| Sample | Weight[5] | Titre | $LD_{99}$[4] | Titre | $LD_{99}$[4] | Titre | $LD_{99}$[4] | Titre | $LD_{99}$[4] |
| EB77.LA3.110-1/11 | 68.6 | 2 | 1110 | 0 | | 4 | 540 | 32 | 67 |
| EB77.LA3.110-12/13 | 11.7 | 0 | | 0 | | 0 | | 4 | 92 |
| EB77.LA3.110-14/15 | 12.7 | 0 | | 0 | | 0 | | 4 | 99 |
| EB77.LA3.110-16/22 | 28.0 | 0 | | 1 | 880 | 1 | 880 | 128 | 6.8 |
| EB77.LA3.110-23/26 | 40.7 | 0 | | 1 | 1300 | 4 | 320 | 1024 | 1.2 |
| EB77.LA3.110-27/28 | 22.6 | 0 | | 8 | 88 | 256 | 2.8 | 512 | 1.4 |
| EB77.LA3.110-29/33 | 68.9 | 2 | 1100 | 2 | 1100 | 64 | 34 | 1024 | 2.1 |
| EB77.LA3.110-34/35 | 116.5 | 64 | 57 | 32 | 110 | 512 | 7.1 | 2048 | 1.8 |
| EB77.LA3.110-36 | 46.2 | 32 | 45 | 32 | 45 | 512 | 2.8 | 1024 | 1.4 |
| EB77.LA3.110-37 | 41.4 | 32 | 40 | 32 | 40 | 128 | 10 | 512 | 2.5 |
| EB77.LA3.110-38 | 40.8 | 64 | 20 | 16 | 80 | 512 | 2.5 | 1024 | 1.2 |
| EB77.LA3.110-39 | 36.6 | 32 | 36 | 32 | 36 | 512 | 2.2 | 1024 | 1.1 |
| EB77.LA3.110-40 | 18.4 | 8 | 72 | 8 | 72 | 8 | 72 | 256 | 2.2 |
| EB77.LA3.110-41/43 | 102.4 | 128 | 25 | 128 | 25 | 8 | 400 | 2048 | 1.6 |
| EB77.LA3.110-44/45 | 87.6 | 128 | 21 | 256 | 11 | 8 | 340 | 1024 | 2.7 |
| EB77.LA3.110-46/48 | 116.0 | 128 | 28 | 512 | 7.1 | 8 | 450 | 2048 | 1.8 |
| EB77.LA3.110-49/51 | 94.3 | 256 | 12 | 512 | 5.8 | 8 | 370 | 2048 | 1.4 |
| EB77.LA3.110-52 | 21.0 | 32 | 20 | 128 | 5.1 | 4 | 160 | 512 | 1.3 |

TABLE 7-continued

Activity of Preparative HPLC Pools.

| Sample | Weight[5] | Ne Titre | Ne $LD_{99}$[4] | Bs Titre | Bs $LD_{99}$[4] | Tr Titre | Tr $LD_{99}$[4] | Cy Titre | Cy $LD_{99}$[4] |
|---|---|---|---|---|---|---|---|---|---|
| EB77.LA3.110-53 | 31.2 | 32 | 31 | 256 | 3.8 | 2 | 490 | 2048 | 0.48 |
| EB77.LA3.110-54 | 37.0 | 64 | 18 | 128 | 9.0 | 2 | 580 | 2048 | 0.57 |
| EB77.LA3.110-55 | 42.1 | 128 | 10 | 256 | 5.1 | 2 | 660 | 2048 | 0.64 |
| EB77.LA3.110-56/58 | 142.7 | 256 | 17 | 1024 | 4.4 | 1 | 4500 | 2048 | 2.2 |
| EB77.LA3.110-59/60 | 66.8 | 64 | 33 | 256 | 8.2 | 0 | | 2048 | 1.0 |
| EB77.LA3.110-61/62 | 23.5 | 16 | 46 | 64 | 11 | 0 | | 1024 | 0.72 |
| EB77.LA3.110-63/70 | 50.8 | 4 | 400 | 64 | 25 | 0 | | 2048 | 0.77 |
| EB77.LA3.110-71/80 | 11.5 | 0 | | 0 | | 0 | | 64 | 5.6 |
| EB77.LA3.110-81/90 | 8.9 | 0 | | 0 | | 0 | | 64 | 4.3 |
| EB77.LA3.110-91/100 | 29.2 | 0 | | 1 | 910 | 0 | | 128 | 7.1 |

[4]$LD_{99}$ in μg/mL calculated as weight of chemical in last well with activity; however, the real value may be lower as end point not attained.
[5]Weight in mg.

Example 3

Chemical Structural Elucidation
EBI-23

The pool of like material (fractions 59-63, 370 mg) from the gradient preparative HPLC run was dissolved in methanol and subjected to preparative HPLC (10 an ectoparasite and/or an endoparasites of humans and/or animals, (C) an antibiotic and therefore would be useful in treatment or prophylaxis of an infection by bacteria of humans and/or animals, (D) an antiprotozoal and therefore would be useful in treatment or prophylaxis of an infection by protozoa of humans and/or animals, (E) an anti-inflammatory and therefore would be useful in treatment or prophylaxis of an anti-inflammatory condition, and (F) an immunosuppressive agent.

TABLE 9

Bioassay of EBI-23

| Sample | Weight[5] | Ne LD$_{99}$[4] | BS LD$_{99}$[4] | Tr LD$_{99}$[4] | Cy LD$_{99}$[4] | Gi LD$_{99}$[4] |
|---|---|---|---|---|---|---|
| EB116.LA3.31-27/32 | 82.1 | 100 | 3.1 | — | 0.78 | 50 |

[4]LD$_{99}$ in μg/mL calculated as weight of chemical in last well with activity, however the real value may be lower as end point not attained.
[5]Weight in mg.

EBI-24

From the preparative HPLC described above fractions 36 to 40 were combined. Fractions 36 to 40 which were concentrated under vacuum, freeze dried and the resulting product was analysed by UV spectroscopy, HPLC analysis, ES-MS and NMR (Table 10). From the HPLC, ES-MS and NMR analysis it was determined that EB116.LA3.31-36/40 contained the following compound referred to herein as EBI-24.

TABLE 10

NMR Data for EBI-24 in DMSO-d6 at 75/600 MHz

| No. | $^{13}$C | $^1$H | Multiplicity (J Hz) |
|---|---|---|---|
| 2 | 161.3 | | |
| 3 | 123.2 | 6.14 | d (10.0) |
| 4 | 140.8 | 7.04 | dd (10.0, 5.2) |
| 5 | 67.9 | 4.37 | t (4.9) |
| 6 | 78.9 | 5.09 | m |
| 7 | 47.6 | 2.42, 2.04 | dd (14.6, 6.9) |
|  |  |  | dd (14.6, 2.5) |
| 8 | 105.2 | | |
| 9 | 40.0 | 1.86, 1.79 | m |
| 10 | 62.2 | 3.94 | m |
| 11 | 37.0 | 1.59, 1.31 | m |
| 12 | 63.4 | 4.20 | m |
| 13 | 43.2 | 1.54, 1.33 | m |
| 14 | 66.9 | 3.51 | m |
| 15 | 37.2 | 1.30 | m |
| 16 | 25.1 | 1.35, 1.23 | m |
| 17 | ~29 | 1.22 | m |
| 18 | ~29 | 1.22 | m |
| 19 | ~29 | 1.22 | m |
| 20 | ~29 | 1.22 | m |
| 21 | ~29 | 1.22 | m |
| 22 | ~29 | 1.22 | m |
| 23 | ~29 | 1.22 | m |
| 24 | ~29 | 1.22 | m |
| 25 | 31.9 | 1.91 | m |
| 26 | 128.9 | 5.36 | m |
| 27 | 131.5 | 5.39 | m |
| 28 | 25.0 | 1.94 | m |
| 29 | 13.8 | 0.91 | t (7.4) |
| 10-OH | | n.d. | |
| 12-OH | | n.d. | |

The bioassay results of Table 11 and those stated in Example 4 'Additional in vitro activity' and in Example 5 "Details and results of anti-inflammatory screening of EBI-23 and EBI-24" and Example 18 "Immunomudulation inhibition of the mixed lymphocyte reaction" clearly indicate that compound EBI-24 has efficacy as (A) a cytotoxic agent and therefore would be useful in the treatment and prophylaxis of cell proliferative diseases such as tumors, leukaemia, lymphoma and related disorders, (B) an antiparasitic and therefore would be useful in the treatment of infestation by a parasite, such as an ectoparasite and/or an endoparasites of humans and/or animals, (C) an antibiotic and therefore would be useful in treatment or prophylaxis of an infection by bacteria of humans and/or animals, (D) an antiprotozoal and

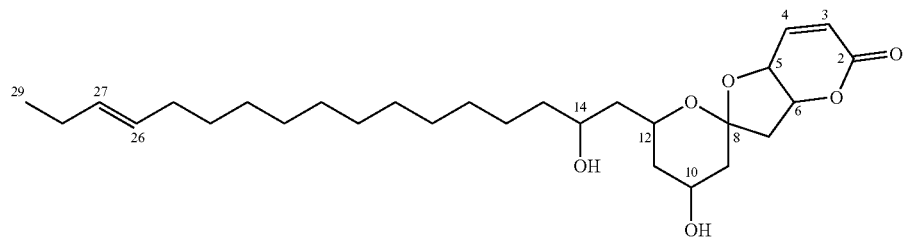 [SMILES: CC/C=C/CCCCCCCCCCCC(O)CC1CC(O)CC2(CC3OC(=O)C=CC3O2)O1]

therefore would be useful in treatment or prophylaxis of an infection by protozoa of humans and/or animals, (E) an insecticide and therefore would be useful use in the eradication and/or growth inhibition of an insect including a broad range of insect species, (F) an anti-inflammatory and therefore would be useful in treatment or prophylaxis of an anti-inflammatory condition, and (G) an immunosuppressive agent.

TABLE 11

Bioassay of EBI-24

| Sample | Weight[5] | Ne LD$_{99}$[4] | BS LD$_{99}$[4] | Tr LD$_{99}$[4] | Cy LD$_{99}$[4] | Gi LD$_{99}$[4] | DipP[4]/ DipH[4] |
|---|---|---|---|---|---|---|---|
| EB116.LA3.31-36/40 | 43.5 | 100 | 13 | — | 0.78 | 100 | P/P |

[4]LD$_{99}$ μg/mL calculated as weight of chemical in last well with activity, however the real value may be lower as end point not attained.
[5]Weight in mg.

EBI-25

From the preparative HPLC described above fractions 56 to 63 were combined. Fractions 56 to 63 which were concentrated under vacuum, freeze dried and the resulting product was analysed by UV spectroscopy, HPLC analysis, ES-MS and NMR (Table 12). From the HPLC, ES-MS and NMR analysis it was determined that EB116.LA3.31-56/63 contained the following compound referred to herein as EBI-25:

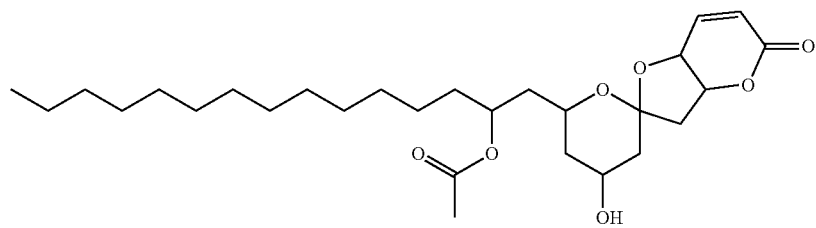 [SMILES: CCCCCCCCCCCCCC(CC1CC(O)CC2(CC3OC(=O)C=CC3O2)O1)OC(C)=O]

TABLE 12

NMR Data for EBI-25 in DMSO-d6 at 75/600 MHz

| No. | $^{13}$C | $^{1}$H | Multiplicity (J Hz) |
|---|---|---|---|
| 2 | 161.3 | | |
| 3 | 123.2 | 6.14 | d (9.9) |
| 4 | 140.7 | 7.05 | dd (9.9, 5.3) |
| 5 | 68.0 | 4.38 | t (4.9) |
| 6 | 78.9 | 5.09 | m |
| 7 | 47.6 | 2.40, 2.06 | dd (14.6, 6.8) |
| | | | dd (14.6, 2.4) |
| 8 | 105.2 | | m |
| 9 | 38.9 | 1.85, 1.78 | m |
| 10 | 62.0 | 3.93 | m |
| 11 | 37.0 | 1.52, 1.34 | m |
| 12 | 63.1 | 4.14 | m |
| 13 | 39.3 | 1.61, 1.54 | m |
| 14 | 70.8 | 4.92 | m |
| 15 | 33.5 | 1.53, 1.47 | m |
| 16 | 24.6 | 1.24 | m |
| 17 | ~29 | 1.22 | m |
| 18 | ~29 | 1.22 | m |
| 19 | ~29 | 1.22 | m |
| 20 | ~29 | 1.22 | m |
| 21 | ~29 | 1.22 | m |
| 22 | ~29 | 1.22 | m |
| 23 | ~29 | 1.22 | m |
| 24 | ~29 | 1.22 | m |
| 25 | 31.3 | 1.22 | m |
| 26 | 22.1 | 1.25 | m |
| 27 | 13.9 | 0.84 | t (7.0) |
| 10-OH | | n.d. | |
| 12-OH | | n.d. | |

The bioassay results of Table 13 and those stated in Example 4 'Additional in vitro activity' clearly indicate that compound EBI-25 has efficacy as (A) a cytotoxic agent and therefore would be useful in the treatment and prophylaxis of cell proliferative diseases such as tumors, leukaemia, lymphoma and related disorders, (B) an antibiotic and therefore would be useful in treatment or prophylaxis of an infection by bacteria of humans and/or animals, (C) an antiprotozoal and therefore would be useful in treatment or prophylaxis of an infection by protozoa of humans and/or animals, and (D) an insecticide and therefore would be useful use in the eradication and/or growth inhibition of an insect including a broad range of insect species.

TABLE 13

Bioassay of EBI-25

| Sample | Weight[5] | Ne LD$_{99}$[4] | BS LD$_{99}$[4] | Tr LD$_{99}$[4] | Cy LD$_{99}$[4] | Gi LD$_{99}$[4] | DipH[4] |
|---|---|---|---|---|---|---|---|
| EB116.LA3.31-56/63 | 44.6 | — | 25 | — | 1.6 | 50 | P |

[4]LD$_{99}$ in μg/mL calculated as weight of chemical in last well with activity, however the real value may be lower as end point not attained.
[5]Weight in mg.

EBI-37

Pooled fractions 42 to 44 of EB115 (*Cinnamomum laubatii*) were isolated and analysed by UV spectroscopy, HPLC analysis, ES-MS and NMR. From the HPLC, ES-MS and NMR analysis it was determined that EB115.LA3.31-60-40/42 contained a compound referred to as EBI-37 which was identical to EBI-23.

The bioassay results of Table 14 clearly indicate that compound EBI-37 has efficacy as (A) a cytotoxic agent and therefore would be useful in the treatment and prophylaxis of cell proliferative diseases such as tumors, leukaemia, lymphoma and related disorders, (B) an antibiotic and therefore would be useful in treatment or prophylaxis of an infection by bacteria of humans and/or animals, and (C) an antiprotozoal and therefore would be useful in treatment or prophylaxis of an infection by protozoa of humans and/or animals.

TABLE 14

Bioassay of EBI-37

| Sample | Weight[5] | Ne LD$_{99}$[4] | BS LD$_{99}$[4] | Tr LD$_{99}$[4] | Cy LD$_{99}$[4] | Gi LD$_{99}$[4] |
|---|---|---|---|---|---|---|
| EB115.LA3.60-40/42 | 130 | — | 6.3 | — | 0.78 | 50 |

[4]LD$_{99}$ in μg/mL calculated as weight of chemical in last well with activity; however, the real value may be lower as end point not attained.
[5]Weight in mg.

EBI-38

Fractions 47 to 49 of EB115 were pooled and concentrated under vacuum, freeze dried and the resulting product was analysed by UV spectroscopy, HPLC analysis, ES-MS and NMR. From the HPLC, ES-MS and NMR analysis it was determined that EB115.LA3.60-47/49 contained a compound referred to herein as EBI-38 and found to be identical to EBI-24.

The bio assay results of Table 15 clearly indicate that compound EBI-38 has efficacy as (A) a cytotoxic agent and therefore would be useful in the treatment and prophylaxis of cell proliferative diseases such as tumors, leukaemia, lymphoma and related disorders, (B) an antiparasitic and therefore would be useful in the treatment of infestation by a parasite, such as an ectoparasite and/or an endoparasites of humans and/or animals, (C) an antibiotic and therefore would be useful in treatment or prophylaxis of an infection by bacteria of humans and/or animals, and (D) an antiprotozoal and therefore would be useful in treatment or prophylaxis of an infection by protozoa of humans and/or animals.

TABLE 15

Bioassay of EBI-38

| Sample | Weight[5] | Ne LD$_{99}$[4] | BS LD$_{99}$[4] | Tr LD$_{99}$[4] | Cy LD$_{99}$[4] | Gi LD$_{99}$[4] |
|---|---|---|---|---|---|---|
| EB115.LA3.60-47/49 | 7.7 | 50 | 13 | — | 0.78 | 50 |

[4]LD$_{99}$ in µg/mL calculated as weight of chemical in last well with activity; however, the real value may be lower as end point not attained.
[5]Weight in mg.

EBI-39

Fractions 62 to 64 of EB115 were concentrated under vacuum, freeze dried and the resulting product was analysed by UV spectroscopy, HPLC analysis, ES-MS and NMR. From the HPLC, ES-MS and NMR analysis it was determined that EB115.LA3.60-62/64 contained a compound referred to herein as EBI-39 which was found to be identical to EBI-25.

The bioassay results of Table 16 clearly indicate that compound EBI-39 has efficacy as (A) a cytotoxic agent and therefore would be useful in the treatment and prophylaxis of cell proliferative diseases such as tumors, leukaemia, lymphoma and related disorders, (B) an antibiotic and therefore would be useful in treatment or prophylaxis of an infection by bacteria of humans and/or animals, and (C) an antiprotozoal and therefore would be useful in treatment or prophylaxis of an infection by protozoa of humans and/or animals.

TABLE 16

Bioassay of EBI-31

| Sample | Weight[5] | Ne LD$_{99}$[4] | BS LD$_{99}$[4] | Tr LD$_{99}$[4] | Cy LD$_{99}$[4] | Gi LD$_{99}$[4] |
|---|---|---|---|---|---|---|
| EB115.LA3.60-62/64 | 7.7 | — | 13 | — | 1.6 | 50 |

[4]LD$_{99}$ in µg/mL calculated as weight of chemical in last well with activity, however the real value may be lower as end point not attained.
[5]Weight in mg.

EBI-42

Fractions 83 to 86 of EB115 were combined, concentrated under vacuum, freeze dried and the resulting product was analysed by UV spectroscopy, HPLC analysis, ES-MS and NMR (Table 17). From the HPLC, ES-MS and NMR analysis it was determined that EB115.LA3.60-83/86 contained the following compound referred to herein as EBI-42:

TABLE 17

NMR Data for EBI-42 in DMSO-d6 at 75/600 MHz

| No. | $^{13}$C | $^{1}$H | Multiplicity (J Hz) |
|---|---|---|---|
| 2 | 161.3 | | |
| 3 | 123.1 | 6.15 | d (9.8) |
| 4 | 140.7 | 4.01 | dd (9.8, 5.1) |
| 5 | 67.7 | 4.44 | t (4.8) |
| 6 | 80.1 | 5.21 | m |
| 7 | 45.6 | 2.42, 2.25 | dd (14.8, 6.5) dd (14.8, 2.5) |
| 8 | 102.9 | | |
| 9 | 29.2 | 1.97, 1.86 | m |
| 10 | 127.3 | 5.62 | m |
| 11 | 128.5 | 5.96 | m |
| 12 | 66.4 | 3.86 | m |
| 13 | 38.9 | 1.78, 1.66 | m |
| 14 | 70.5 | 4.93 | m |
| 15 | 33.4 | 1.52 | m |
| 16 | 24.5 | 1.24 | m |
| 17 | ~29 | 1.23 | m |
| 18 | ~29 | 1.23 | m |
| 19 | ~29 | 1.23 | m |
| 20 | ~29 | 1.23 | m |
| 21 | ~29 | 1.23 | m |
| 22 | ~29 | 1.23 | m |
| 23 | ~29 | 1.23 | m |
| 24 | ~29 | 1.23 | m |
| 25 | 31.2 | 1.22 | m |
| 26 | 22.0 | 1.25 | m |
| 27 | 13.9 | 0.84 | t (7.0) |
| 28 | 170.0 | | |
| 29 | 20.9 | 1.98 | s |

The bioassay results of Table 18 and those stated in Example 4 'Additional in vitro activity' clearly indicate that compound EBI-42 has efficacy as a cytotoxic agent and therefore would be useful in the treatment and prophylaxis of cell proliferative diseases such as tumors, leukaemia, lymphoma and related disorders.

TABLE 18

Bioassay of EBI-42

| Sample | Weight[5] | Ne LD$_{99}$[4] | BS LD$_{99}$[4] | Tr LD$_{99}$[4] | Cy LD$_{99}$[4] | Gi LD$_{99}$[4] |
|---|---|---|---|---|---|---|
| EB115.LA3.60-62/64 | 1.8 | — | — | — | 1.6 | — |

[4]LD$_{99}$ in µg/mL calculated as weight of chemical in last well with activity; however, the real value may be lower as end point not attained.
[5]Weight in mg.

EBI-69

Fractions 92 to 100 of EB77 were combined, concentrated under vacuum, freeze dried and the resulting product was analysed by UV spectroscopy, HPLC analysis, ES-MS and NMR. From the HPLC, ES-MS and NMR analysis it was

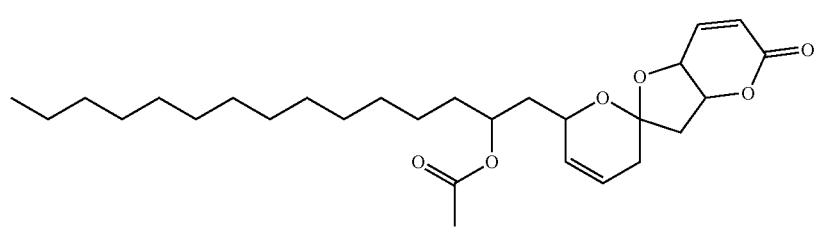 [SMILES: CCCCCCCCCCCCCC(CC1C=CCC2(CC3OC(=O)C=CC3O2)O1)OC(C)=O]

determined that EB77.LA4.92-100 contained the following compound referred to herein as EBI-69 which was found to be identical to EBI-23.

The bioassay results of Table 19 and those stated in Example 4 'Additional in vitro activity' clearly indicate that compound EBI-69 has efficacy as (A) a cytotoxic agent and therefore would be useful in the treatment and prophylaxis of cell proliferative diseases such as tumors, leukaemia, lymphoma and related disorders, (B) an antiparasitic and therefore would be useful in the treatment of infestation by a parasite, such as an ectoparasite and/or an endoparasites of humans and/or animals, (C) an antibiotic and therefore would be useful in treatment or prophylaxis of an infection by bacteria of humans and/or animals, (D) an antiprotozoal and therefore would be useful in treatment or prophylaxis of an infection by protozoa of humans and/or animals, and (E) an insecticide and therefore would be useful use in the eradication and/or growth inhibition of a an insect including a broad range of insect species.

TABLE 19

| Sample | Bioassay of EBI-69 | | | | | |
|---|---|---|---|---|---|---|
| | Wt[5] | Ne Titre/ $LD_{99}^4$ | BS Titre/ $LD_{99}^4$ | Tr Titre/ $LD_{99}^4$ | Cy Titre/ $LD_{99}^4$ | DipP[4] | Gi Titre/ $LD_{99}^4$ |
| EB77.LA4.92-100 | 28 | 1/63 | 16/3.9 | 0/— | 256/0.24 | P | 4/16 |

[4]$LD_{99}$ in μg/mL calculated as weight of chemical in last well with activity; however, the real value may be lower as end point not attained.
[5]Wt is weight in mg.

Fraction 9 of EB116 was concentrated, under vacuum, freeze dried and the resulting product was analysed by ES-MS and NMR. From the NMR and mass spectrometric data, this fraction yielded a compound comprising one or both of the following compounds referred herein as EBI-72.

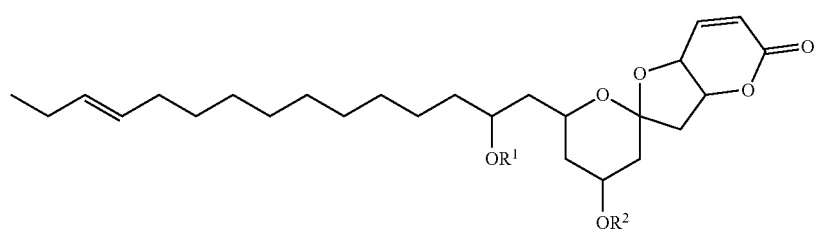

$R^1$ is Ac and $R^2$ is H or $R^1$ is H and $R^2$ is Ac.
$^1$H NMR (CDCl$_3$, 300 MHz) 0.94 (t, 3H), 1.23 (vbs, 15H), 1.30-1.63 (m, 4H), 1.67-2.00 (m, 7H), 2.00 (s, 3H), 2.22 (dd, J 14.6, 2.7 Hz, 1H), 2.50 (s, 3H), 2.22 (dd, J 14.6, 6.9 Hz, 1H), 3.1 (bs, 1H), 4.08 (bs, 1H), 4.10-4.12 (m, 1H), 4.52 (t, J 4.9 Hz, 1H), 4.98-5.06 (m, 2H), 5.27-5.50 (m, 2H), 6.18 (d, J 9.9 Hz, 1H), 6.86 (dd, J 9.9, 5.2 Hz, 1H).
ES-MS C28H44O7 515 (M+Na), 1006 (2M+Na).

Fractions 10 and 11 of EB116 were pooled and concentrated under vacuum, freeze dried and the resulting product was analysed by ES-MS and NMR. From the NMR and mass spectrometric data, this fraction yielded a compound comprising one or both of the following compounds referred herein as EBI-73.

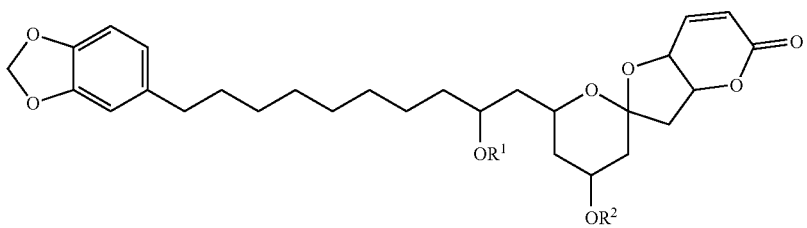

$R^1$ is Ac and $R^2$ is H or $R^1$ is H and $R^2$ is Ac.
$^1$H NMR (CDCl$_3$, 300 MHz) 1.17-1.63 (m, 16H), 1.8 (bd, 2H), 1.87-2.00 (m, 2H), 2.03 (s, 3H), 2.10-2.27 (m, 2H), 2.43-2.63 (m, 3H), 3.73-3.87 (m, 1H), 4.30-4.43 (m, 1H), 4.47 (t, J 5.1 Hz, 1H), 4.97-5.10 (m, 2H), 5.90 (s, 2H), 6.14 (d, J 5.1 Hz, 1H), 6.57-6.77 (m, 3H), 6.86 (dd, J 9.9, 5.1 Hz, 1H).
ES-MS C30H40O9 566 (M+Na−1).

Example 4

Additional In Vitro Activity
EBI-23

Additional in vitro assays were performed and demonstrated that EBI-23 has: cytotoxic activity against normal human fibroblasts (NFF) at 30 μg/mL; and antitumor activity against the following cell lines:
  leukemia K562 at 3 μg/mL;
  melanoma MM96L at 1 μg/mL;
  melanoma MM418c5 at 1 μg/mL;
  prostate DU145 at 3 μg/mL;
  breast MCF-7 at 1 μg/mL;
  ovarian C180-135 at 1 μg/mL.
EBI-24

Additional in vitro assays were performed and demonstrated that EBI-24 has: cytotoxic activity against normal human fibroblasts (NFF) at 10 μg/mL; and antitumor activity against the following cell lines:
  leukemia K562 at 10 μg/mL;
  melanoma MM96L at 3 μg/mL;

melanoma MM418c5 at 10 µg/mL;
prostate DU145 at 10 µg/mL;
breast MCF-7 at 10 µg/mL;
ovarian C180-13S at 3 µg/mL.

EBI-25

Additional in vitro assays were performed and demonstrated that EBI-25 has: cytotoxic activity against normal human fibroblasts (NFF) at 30 µg/mL; and antitumor activity against the following cell lines:
leukemia K562 at 30 µg/mL;
melanoma MM96L at 10 µg/mL;
melanoma MM418c5 at 10 µg/mL;
prostate DU145 at 30 µg/mL;
breast MCF-7 at 300 µg/mL;
ovarian C180-13S at 3 µg/mL.

EBI-42

Additional in vitro assays were performed and demonstrated that EBI-42 has:
no cytotoxic activity against normal human fibroblasts (NFF) at 10 µg/mL; and
antitumor activity against the following cell lines;
melanoma MM96L at 10 µg/mL; and
ovarian C180-13S at 10 µg/mL.

Example 5

Details and Results of Antiinflammatory Screening of EBI-23 and EBI-24

Three main assays were performed; transformation, regression and mixed lymphocyte reactions (MLRs). Reference is made to Moss et al., (D J, Rickinson A B, Pope J H: Long-term T-cell-mediated immunity to Epstein-Barr virus in man. III. Activation of cytotoxic T cells in virus-infected leukocyte cultures. Int J Cancer 1979, 23:618-625). Complete regression of virus-induced transformation in cultures of seropositive donor leukocytes Both regression and MLR quantitative experimental results were obtained visually and by the addition of [methyl-$^3$H]thymidine (3H-T). 3H-T is a nucleoside analogue and is incorporated into the DNA of proliferating cells. If cells are proliferating, the counts/minute (cpm) is high; if cells are dead, the cpm is low.

Transformation and Regression
Transformation Background

EBV seronegative and seropositive donors' peripheral blood mononuclear cells (PBMCs) were infected with EBV. A small percent of the B-cells contained within the PBMC population were transformed into immortalised lymphoblastoid cell lines (LCLs).

Regression Background

TABLE 21

Regression in EBV sero-positive PMBCs induced by EBV specific memory T-cells

| | Day 8-10 | Day 14 | Day 28 |
|---|---|---|---|
| EBV sero + donor PBMC + EBV | transformation | regression/death | death |
| EBV sero − donor PBMC + EBV | transformation | transformation | growth |

Regression only occurs in EBV sero-positive PBMCs induced by EBV specific memory T-cells.
Experiments with EBI-23 and EBI-24 Isolated from Both EB116 and EB115

Methods:

EBI-23 and EBI-24 were added at 2 µg/mL concentration individually to EBV seropositive and seronegative donors PBMCs previously infected with EBV, to monitor the inhibition of transformation and/or regression.

The cells were then incubated for 28 days when results were determined visually and by the addition of 3H-T to obtain quantitative data.

Results:

The individual transformation summaries were determined by visual data and 3H-T cpm data from EBV seronegative donors' peripheral blood mononuclear cells (PBMC). The control used was these PBMCs minus chemical. The 3H-T cpm cut-off values were determined for each individual assay by this control value, plus and minus a five (5)-fold difference. This 5-fold difference was chosen as it compared the 3H-T cpm data from controls and visual inspection of all test wells.

The individual regression summaries were determined by visual data and 3H-T cpm data from EBV seropositive donors' PBMC. The control was these PBMCs minus chemical. The 3H-T cpm cut of values were determined for each individual assay by this control value, plus and minus a one hundred (100)-fold difference. This 100-fold difference was chosen as it compared the 3H-T cpm and visual data from controls with the 3H-T cpm and visual data of all test wells. The positive control was the cpm from cells incubated with cyclosporine (CSA), a chemical known to inhibit regression, while the negative control was PBMC minus virus and chemical.

Mixed Lymphocyte Reaction (MLR):

MLR Background and Method

Studying the Effect of EBI-23 and EBI-24 Isolated from EB115 and EB116 on Allogeneic T-Cell Responses.

PBMCs were mixed with irradiated, HLA mismatched LCLs and monitored for T-cell activation/growth after six (6) days.

Results

The individual MLR summaries were determined by visual data and 3H-T cpm from PBMCs+HLA mismatched LCLs plus EB chemical. The control was these PBMCs+LCLs minus chemical. The 3H-T cpm cut of values were determined for each individual assay by this control value, plus and minus a five (5)-fold difference. This 5-fold difference was chosen as it compared the 3H-T cpm and visual data from controls with the 3H-T cpm and visual data of all test wells. The positive control was the cpm from cells incubated with cyclosporine (CSA), a chemical known to inhibit MLR, while the negative control was PBMC alone and LCL alone Results of Screening for Specific Chemicals:

EBI-23 and EBI-24 showed strong inhibition of transformation.

Example 6

Derivatisation of EBI-23 by Hydrogenation 1 mg of EBI-23 in 200 µL methanol was treated with 4 mg PtO$_2$ for 24 hours at room temperature to give:

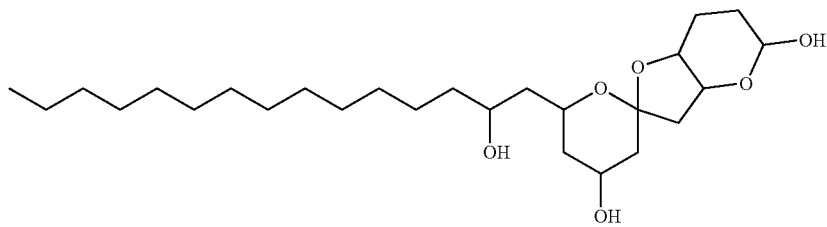 [SMILES: CCCCCCCCCCCCCC(O)CC1CC(O)CC2(CC3OC(O)CCC3O2)O1]

$C_{26}H_{48}O_6$; Exact mass: 456.3451; Molecular weight: 456.6557; C, 68.38; H, 10.59; O, 21.02. MS (ESI): 479, (M+Na).

Example 7

Derivatisation of EBI-23 by Acetylation 1 mg of EBI-23 in 400 µL acetic anhydride and pyridine (1:1) was stirred at room temperature for 17 hours to give:

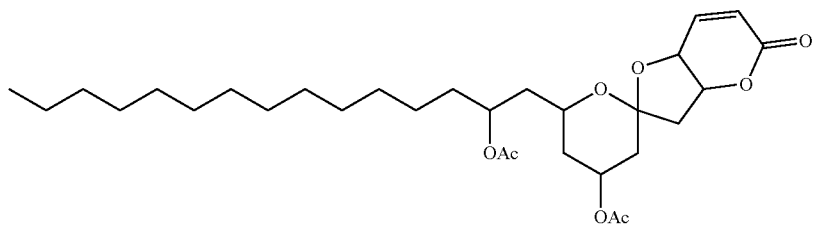 [SMILES: CCCCCCCCCCCCCC(CC1CC(OC(C)=O)CC2(CC3OC(=O)C=CC3O2)O1)OC(C)=O]

$C_{30}H_{48}O_8$; Exact mass: 536.3349; Molecular weight: 536.6973; C, 67.14; H, 9.01; O, 23.85. MS (ESI): 559, (M+Na).

Example 8

Derivatisation of EBI-24 by Hydrogenation 1 mg of EBI-24 in 200 µL methanol was treated with 4 mg $PtO_2$ for 24 hours at room temperature to give:

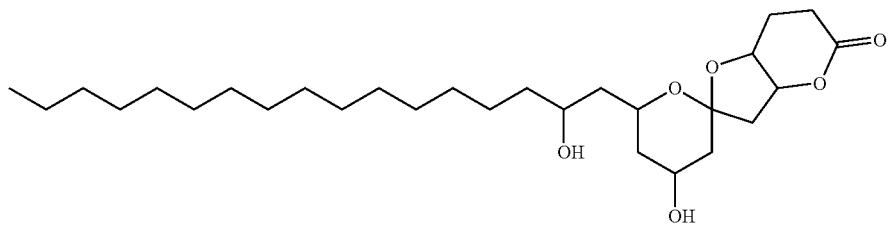 [SMILES: CCCCCCCCCCCCCCCC(O)CC1CC(O)CC2(CC3OC(=O)CCC3O2)O1]

$C_{28}H_{46}O_6$; Exact mass: 478.33; Molecular weight: 478.66; MS (ESI): 501, (M+Na), 533 (M+Na$^+$ MeOH), 565 (M+Na+ 2MeOH).

Example 9

Derivatisation of EBI-24 by Oxidation 1 mg of EBI-24 in 200 µL acetone was treated with 50 µL freshly prepared dimethyldioxirane (DMDO) solution and stirred for 1 hour at 0° C. and 3 hours at room temperature to give:

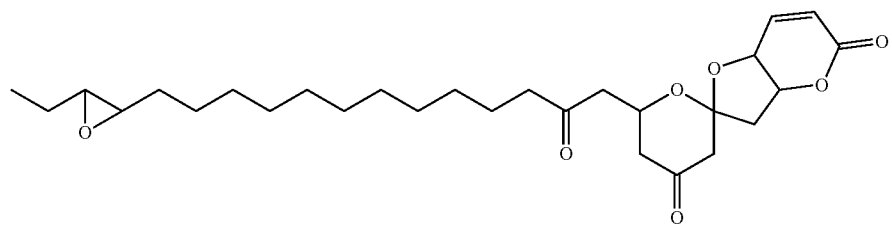

and/or

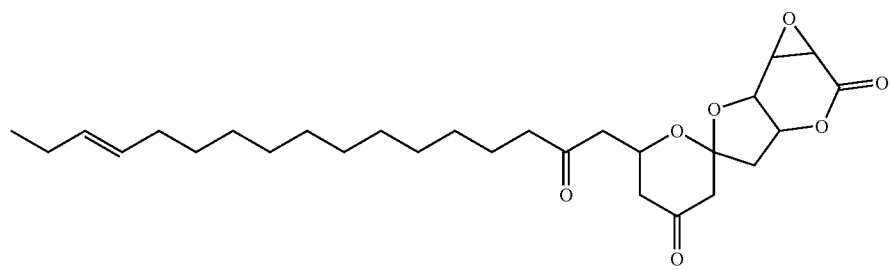

C$_{28}$H$_{42}$O$_7$; Exact mass: 490.2931; Molecular weight: 490.6289; MS (ESI): 513, (M+Na), 1003 (2M+Na).

Example 10

Derivatisation of EBI-24 by Acetylation 1 mg of EBI-24 in 400 µL acetic anhydride and pyridine (1:1) was stirred at room temperature for 17 hours to give:

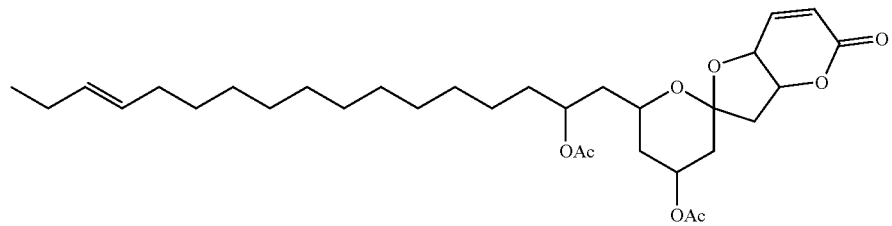 [SMILES: CC/C=C/CCCCCCCCCCCC(CC1CC(OC(C)=O)CC2(CC3OC(=O)C=CC3O2)O1)OC(C)=O]

C$_{32}$H$_{50}$O$_8$; Exact mass: 562.3506; Molecular weight: 562.7346; MS (ESI): 585, (M+Na).

Example 11

Derivatisation of EBI-24 by Hydrogenation 1 mg of EBI-25 in 200 µL methanol was treated with 4 mg PtO$_2$ for 24 hours at room temperature to give.

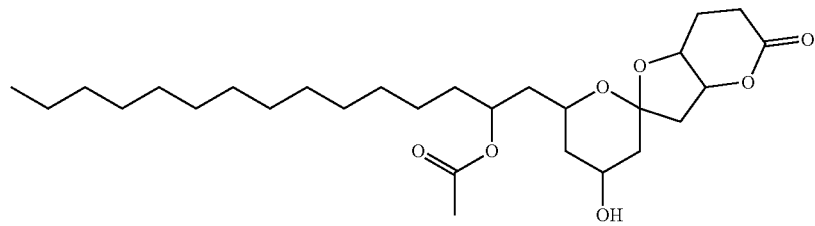 [SMILES: CCCCCCCCCCCCCC(CC1CC(O)CC2(CC3OC(=O)CCC3O2)O1)OC(C)=O]

C$_{28}$H$_{48}$O$_7$; Exact mass: 496.34; Molecular weight: 496.6765; MS (ESI): 551, (M+Na+MeOH), 1079 (2M+Na+ 2MeOH).

Example 12

Derivatisation of EBI-25 by Oxidation 1 mg of EBI-25 in 200 µL acetone was treated with 50 µL freshly prepared dimethyldioxirane (DMDO) solution and stirred for 1 hour at 0° C. and 3 hours at room temperature to give:

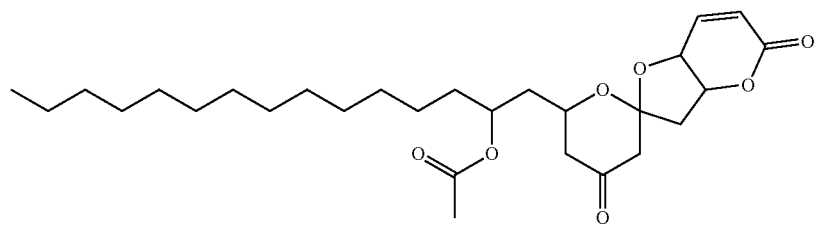 [SMILES: CCCCCCCCCCCCCC(CC1CC(=O)CC2(CC3OC(=O)C=CC3O2)O1)OC(C)=O]

$C_{28}H_{44}O_7$; Exact mass: 492.3087; Molecular weight: 492.6448; MS (ESI): 515, (M+Na), 1007 (2M+Na).

Example 13

Derivatisation of EBI-25 by Acetylation 1 mg of EBI-25 in 400 µL acetic anhydride and pyridine (1:1) was stirred at room temperature for 17 hours to give:

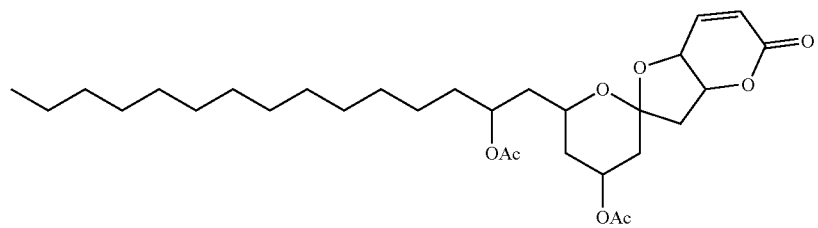 [SMILES: CCCCCCCCCCCCCC(CC1CC(OC(C)=O)CC2(CC3OC(=O)C=CC3O2)O1)OC(C)=O]

$C_{30}H_{48}O_8$; Exact mass: 536.3349; Molecular weight: 536.6973; MS (ESI): 559, (M+Na)

Example 14

Effects of Derivatisation of EBI-23, EBI-24 and EBI-25

A series of derivatisation reactions were conducted on 1 mg amounts of EBI-23, EBI-24, and EBI-25. Mass spectra were run to confirm the nature of the derivatives but the product(s) weren't purified for this preliminary screen of growth-inhibiting activity in a human tumor cell line. The results were compared on the assumption that no losses occurred during derivatisation.

EBI-23 lost most of its activity with hydrogenation and oxidation (presumably due to loss of the double bond) whereas acetylation of the OH or epoxidation of the double bond had less effect. The related structure EBI-24 with a double bond in the long side chain was 10-fold less potent than EBI-23 and only hydrogenation caused loss of activity. EBI-25 was the least potent of this series. It became more active after epoxidation, perhaps as a consequence of increased polarity counteracting the acetylated OH.

Example 15

Morphological and Cell Cycle Effects of EBI-23

At doses close to the IC50, no distinctive change in morphology such as apoptosis was observed with these compounds. This tends to rule out targets such as PKC (prototype compound PMA), DNA damage (prototype cisplatin), kinases (prototype staurosporine), mitochondria or the plasma membrane (cell lysis).

Flow cytometry of several cell lines after 24 hour treatment with 1 µg/mL EBI-23 suggests a variable degree of G2/M arrest. This was not accompanied, however, by the typical rounded morphology of cells treated with tubulin ligands. No DNA fragments were detected, reinforcing the visual observation that little if any apoptosis occurred.

Example 16

Inhibition of B16 Melanoma Growth by EBI-23 in C57BL/6 Mice

After a preliminary experiment to determine the MTD in mice, C57BL/6 mice were implanted with B16 melanoma cells (0.5 million cells per site, 2 sites per mouse sc, 3 mice/group) and treatment commenced 24 hours later. For this initial study, EBI-23 was prepared by diluting an ethanol solution into saline, such that the final ethanol level was 2%. The cloudy solution thus obtained was injected intraperitoneally into mice every day for 7 days. Tumor size and body weight were measured over time.

Figure 4:
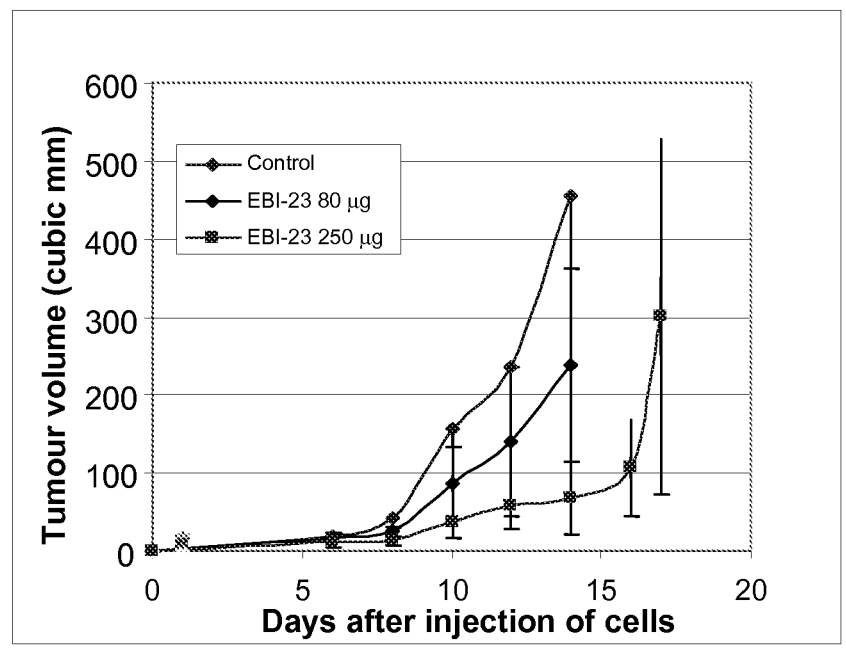
FIG. 4: Graphically represents the treatment of B16 melanoma cells with EBI-23 in C57BL/6 mice.

The results (FIG. 4) showed a dose-related response, with a significant reduction in B16 growth by a dose of 250 µg/mouse/day, and a measurable response at 80 µg.

The mice tolerated this regime well, except there was some weight loss at the higher dose. Treatment was discontinued at 13 days because of limited supply of EBI-23.

Example 17

Treatment of DU145 Prostate Tumors in Nude Mice

Figure 5:
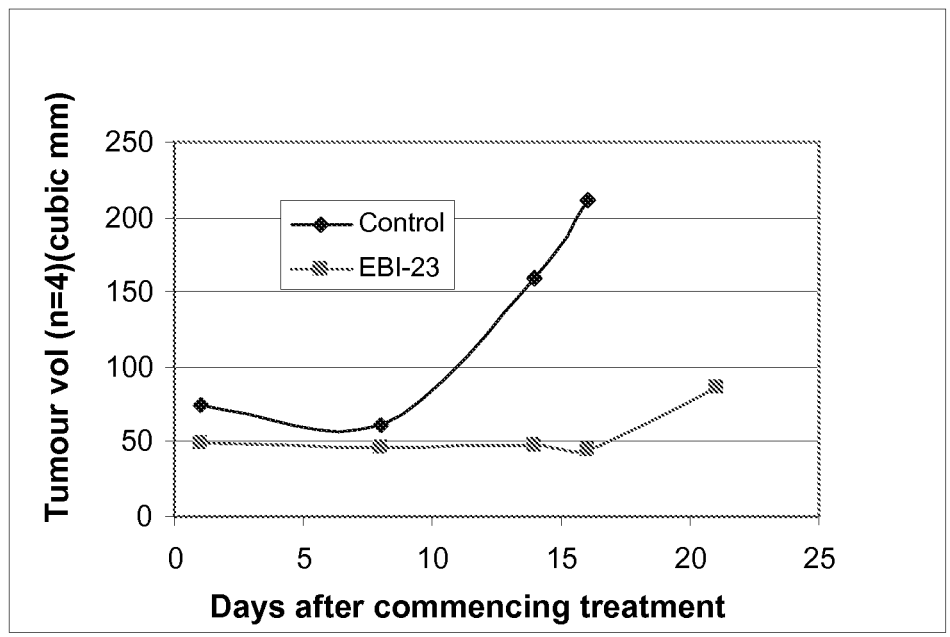
FIG. 5: Graphically represents the treatment of DU145 prostate tumors in nude mice as depicted from the time of commencing treatment.
Figure 6:
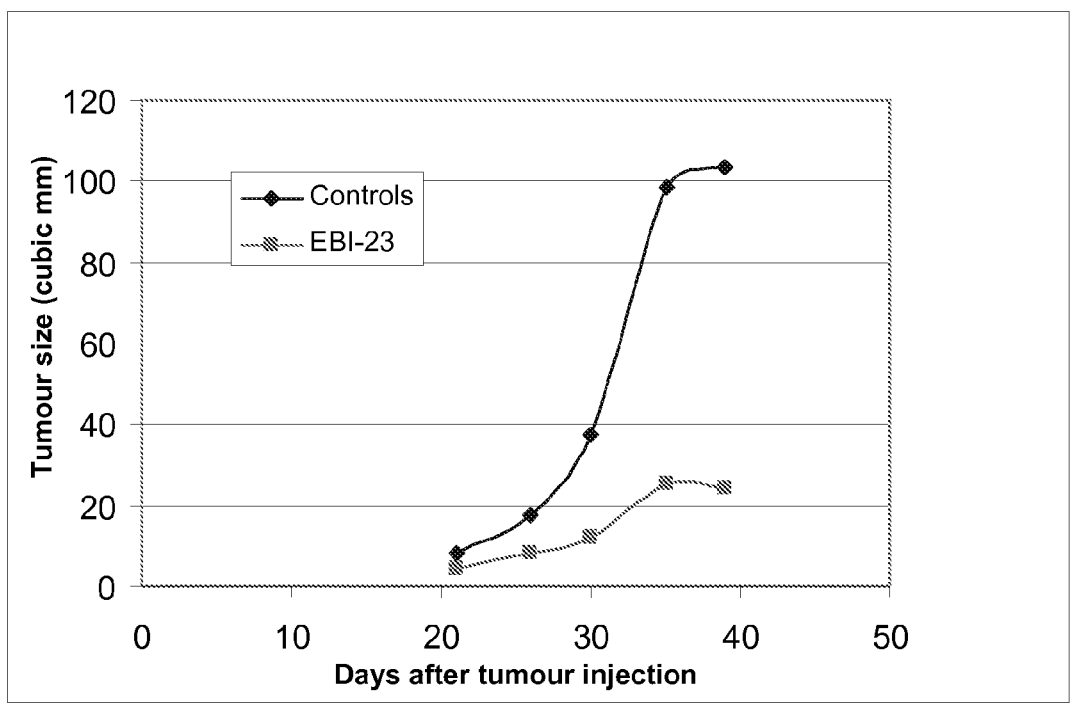
FIG. 6: Graphically represents the treatment of DU145 prostate tumors in nude mice as depicted from the time of tumor cell injection.

The action of EBI-23 on DU145 prostate tumors in nude mice was investigated. Mice were treated with 200 mg/mouse/day to day 14 then 400 mg/mouse/day. The results are shown in FIGS. 5 and 6.

Example 18

Immunomodulation: Inhibition of the Mixed Lymphocyte Reaction

Gamma-irradiated lymphoblastoid cells (LCL, Esptein-Barr virus-transformed B-cells; 17,000) were added to human peripheral blood lymphocytes (PBMC; 50,000 per microtitre well), then the drug, incubated at 37 C as above and labeled with [3H]-thymidine on Day 4. Cells were lysed and washed onto glass fibre mats for scintillation counting. The same drug concentrations were tested for direct toxicity by assay on control LCL (10,000 cells/well).

The MLR measures the ability of normal human T-cells to undergo a proliferative response to allo antigens expressed by a non-proliferating B-cell line. A positive control compound, the clinically-used immunosuppressive drug cyclosporine A, completely inhibited the MLR. EBI-23 was found to inhibit the MLR at 1 µg/mL. This was not due to general toxicity because the growth of control LCLs was unaffected.

Inhibition of MLR by EBI-23 at a dose somewhat higher than the level required to inhibit cell growth suggests that EBI-23 has potential as an immunosuppressive drug. Without wishing to be bound by theory, such reactivity, and indeed anticancer activity, may arise at the molecular level from the potential for beta substitution by nucleophiles in the lactone ring. Such nucleophiles could include amino or reactive thiol groups in specific cellular proteins, with specificity conferred by the chemical reactivity and aliphatic tail of individual members of the EBI-23 family.

Gradient:

| Method: | | | | | | |
|---|---|---|---|---|---|---|
| EBA.M | | | | | | |
| Time (min) | 0 | 20 | 40 | 50 | 51 | 55 |
| % Methanol | 90 | 90 | 100 | 100 | 90 | 90 |
| EBC.M | | | | | | |
| Time (min) | 0 | 10 | 40 | 55 | 56 | 65 |
| % Methanol | 70 | 90 | 100 | 100 | 70 | 70 |
| EBB.M | | | | | | |
| Time (min) | 0 | 30 | 40 | 45 | 50 | 51 | 55 |
| % Methanol | 85 | 90 | 90 | 100 | 100 | 85 | 85 |

The isolated compounds were tested against a number of human and non-human cancer cell lines. The human tumor cell lines were: MCF-7, MDA-MB-231 and T47D, breast cancer; DU145 and PC3, prostate cancer; CI80-13S, ovarian cancer; MM96L, D04, SkMel5, MM418c5 melanoma; HT29, colon cancer; K562 and HL60, leukemia. Mouse cell lines were the B16 mouse melanoma and LK2 UV-induced squamous cell carcinoma (SCC). Neonatal foreskin fibroblasts (NFF) were used as normal control cells. Cells were cultured at 37° C. in 5% carbon dioxide/air, in RPMI 1640 medium containing 10% fetal calf serum.

The results are shown in Table 22.

TABLE 22

Description and anticancer activities of spiroketals

| Compound | HPLC Retention Time (min) | HPLC EB Method | IC50 (ug/ml) for each cell line (drug dose which inhibits cell growth by 50%) | | | | | | | |
|---|---|---|---|---|---|---|---|---|---|---|
| | | | NFF | MCF7 | T47D | DU145 | PC3 | K562 | CI80-13S | MM96L | B16 |
| EBI-23 | | | 2 | 0.5 | | 0.7 | 1.0 | 1.7 | 0.2 | 0.15 | 0.5 |
| EBI-24 | | | 0.8 | 0.2 | | 0.7 | | 0.6 | 0.75 | 1.3 | |
| EBI-25 | | | 3 | 0.34 | | 1 | | 6.1 | 5 | 1.6 | |
| EBI-42 | | | >10 | 6 | | >10 | | >10 | 6 | 6 | |
| EBI-72 | 21.5 | A | 45 | 6 | | | 32 | | | 25 | |
| EBI-73 | 10.7 | A | 6 | 1.7 | 6 | 2 | | | 7 | 1.7 | |
| EB99-EBB_30.3 | 30.3 | B | 25 | 1.5 | 3 | | 3 | 7 | 2 | | 1.5 |
| EB99-EBB_33.3 | 33.3 | B | 4 | 2 | 0.3 | | 2 | 3.5 | 0.3 | | 0.3 |
| EB120_EBC_29.9 | 29.9 | C | 3 | 0.3 | 0.4 | | 0.7 | 4 | 0.3 | | 0.2 |
| EB116/11/5b_5-7.5 | 6 | A | 8 | 1 | 10 | 1.1 | | | | 1 | |
| EB116/11/5b_13-14 | 13.5 | A | 8 | 1.2 | 12 | 1.5 | | | 9 | | |
| EB116_EBA_16.3 | 16.3 | A | 1.1 | 0.9 | 1 | 1.2 | | | 0.7 | 1 | |
| EB116_EBA_24.6 | 24.6 | A | 1.2 | 0.92 | 0.9 | 1.1 | | | 0.37 | 0.5 | |
| EB116_EBA_32.2 | 32.2 | A | 1 | 1 | 1 | 1 | | | 0.1 | 0.11 | |
| EB116_EBA_17.9 | 17.9 | A | 30 | 3.2 | | | 10.8 | | | 30 | |
| EB116_EBA_38.2 | 38.2 | A | 6 | 1.1 | 2 | 8 | | | 1 | 1 | |
| EB116_EBA_35.5 | 35.5 | A | 6 | 3 | | | 6 | | | 3.5 | |

Example 19

A number of plant extracts were subjected to purification by HPLC with one of the following HPLC separation systems:

Column: Phenomenex luna 5u 250×4.60 mm C18
Flow: 0.5 ml/min
Solvent System: Methanol/water Throughout this specification, unless the context requires otherwise, the word "comprises", and variations such as "comprise" or "comprising", will be understood to imply the inclusion of a stated integer or group of integers or steps but not to the exclusion of any other integer or group of integers.

The invention claimed is:

1. A method of treating a bacterial, parasitic or protozoan infection comprising administering to a subject compound of formula (II):

II

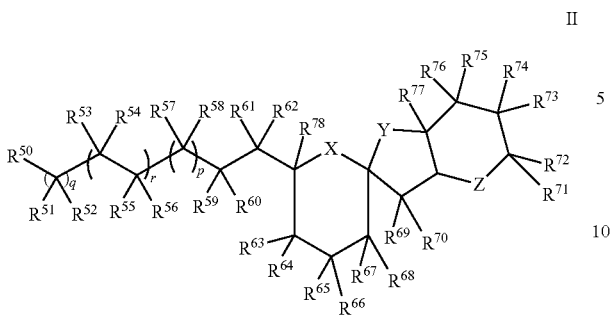

wherein
X, Y and Z are independently selected from —O—, —S—, —NH—, —N($C_1$-$C_6$ alkyl)- and —$CH_2$—;

$R^{50}$ is selected from —$CH_3$, —$C_3$-$C_8$ cycloalkyl, aryl, heterocyclyl and heteroaryl;

$R^{51}$, $R^{52}$, $R^{57}$, $R^{58}$, $R^{61}$, $R^{62}$, $R^{67}$, $R^{68}$, $R^{69}$ and $R^{70}$ are independently selected from hydrogen, —$C_1$-$C_{20}$ alkyl, —$C_2$-$C_{20}$ alkenyl, —$C_2$-$C_{20}$ alkynyl, —$C_3$-$C_8$ cycloalkyl, —$C_6$-$C_{14}$ aryl, —$C_5$-$C_{14}$ heteroaryl, —$C_3$-$C_{14}$ heterocyclyl, arylalkyl, heteroarylalkyl, heterocyclylalkyl, alkoxyalkyl, halo, —CN, —$NO_2$, —$C_1$-$C_{10}$ haloalkyl, —$C_1$-$C_{10}$ dihaloalkyl, —$C_1$-$C_{10}$ trihaloalkyl, —COR, —$CO_2$R, —OR, —SR, —N(R)$_2$, —NROR, —ON(R)$_2$, —SOR, —$SO_2$R, —$SO_3$R, —SON(R)$_2$, —$SO_2$N(R)$_2$, —$SO_3$N(R)$_2$, —P(R)$_3$, —P(O)(R)$_3$, —OSi(R)$_3$, —OB(R)$_2$, —C(W)R and —WC(W)R;

$R^{53}$ to $R^{56}$ are independently selected from hydrogen, —$C_1$-$C_{20}$ alkyl, —$C_2$-$C_{20}$ alkenyl, —$C_2$-$C_{20}$ alkynyl, —$C_3$-$C_8$ cycloalkyl, —$C_6$-$C_{14}$ aryl, —$C_5$-$C_{14}$ heteroaryl, —$C_3$-$C_{14}$ heterocyclyl, arylalkyl, heteroarylalkyl, heterocyclylalkyl, alkoxyalkyl, halo, —CN, —$NO_2$, —$C_1$-$C_{10}$ haloalkyl, —$C_1$-$C_{10}$ dihaloalkyl, —$C_1$-$C_{10}$ trihaloalkyl, —COR, —$CO_2$R, —OR, —SR, —N(R)$_2$, —NROR, —ON(R)$_2$, —SOR, —$SO_2$R, —$SO_3$R, —SON(R)$_2$, —$SO_2$N(R)$_2$, —$SO_3$N(R)$_2$, —P(R)$_3$, —P(O)(R)$_3$, —OSi(R)$_3$, —OB(R)$_2$, —C(W)R and —WC(W)R; or $R^{54}$ and $R^{55}$ taken together form a double bond or are —O—; or $R^{53}$ and $R^{54}$ or $R^{55}$ and $R^{56}$ taken together form a carbonyl group;

$R^{59}$ and $R^{60}$ are independently selected from hydrogen, —$C_1$-$C_{20}$ alkyl, —$C_2$-$C_{20}$ alkenyl, —$C_2$-$C_{20}$ alkynyl, —$C_3$-$C_8$ cycloalkyl, —$C_6$-$C_{14}$ aryl, —$C_5$-$C_{14}$ heteroaryl, —$C_3$-$C_{14}$ heterocyclyl, arylalkyl, heteroarylalkyl, heterocyclylalkyl, alkoxyalkyl, halo, —CN, —$NO_2$, —$C_1$-$C_{10}$ haloalkyl, —$C_1$-$C_{10}$ dihaloalkyl, —$C_1$-$C_{10}$ trihaloalkyl, —COR, —$CO_2$R, —OR, —SR, —N(R)$_2$, —NROR, —ON(R)$_2$, —SOR, —$SO_2$R, —$SO_3$R, —SON(R)$_2$, —$SO_2$N(R)$_2$, —$SO_3$N(R)$_2$, —P(R)$_3$, —P(O)(R)$_3$, —OSi(R)$_3$, —OB(R)$_2$, —C(W)R and —WC(W)R; or $R^{59}$ and $R^{60}$ taken together form a carbonyl group;

$R^{63}$ to $R^{66}$ are independently selected from hydrogen, —$C_1$-$C_{20}$ alkyl, —$C_2$-$C_{20}$ alkenyl, —$C_2$-$C_{20}$ alkynyl, —$C_3$-$C_8$ cycloalkyl, —$C_6$-$C_{14}$ aryl, —$C_5$-$C_{14}$ heteroaryl, —$C_3$-$C_{14}$ heterocyclyl, arylalkyl, heteroarylalkyl, heterocyclylalkyl, alkoxyalkyl, halo, —CN, —$NO_2$, —$C_1$-$C_{10}$ haloalkyl, —$C_1$-$C_{10}$ dihaloalkyl, —$C_1$-$C_{10}$ trihaloalkyl, —COR, —$CO_2$R, —OR, —SR, —N(R)$_2$, —NROR, —ON(R)$_2$, —SOR, —$SO_2$R, —$SO_3$R, —SON(R)$_2$, —$SO_2$N(R)$_2$, —$SO_3$N(R)$_2$, —P(R)$_3$, —P(O)(R)$_3$, —OSi(R)$_3$, —OB(R)$_2$, —C(W)R and —WC(W)R; or $R^{64}$ and $R^{65}$ taken together form a double bond or are —O—; or $R^{63}$ and $R^{64}$ or $R^{65}$ and $R^{66}$ taken together form a carbonyl group;

$R^{71}$ and $R^{72}$ are independently selected from hydrogen, —$C_1$-$C_{20}$ alkyl, —$C_2$-$C_{20}$ alkenyl, —$C_2$-$C_{20}$ alkynyl, —$C_3$-$C_8$ cycloalkyl, —$C_6$-$C_{14}$ aryl, —$C_5$-$C_{14}$ heteroaryl, —$C_3$-$C_{14}$ heterocyclyl, arylalkyl, heteroarylalkyl, heterocyclylalkyl, alkoxyalkyl, halo, —CN, —$NO_2$, —$C_1$-$C_{10}$ haloalkyl, —$C_1$-$C_{10}$ dihaloalkyl, —$C_1$-$C_{10}$ trihaloalkyl, —COR, —$CO_2$R, —OR, —SR, —N(R)$_2$, —NROR, —ON(R)$_2$, —SOR, —$SO_2$R, —$SO_3$R, —SON(R)$_2$, —$SO_2$N(R)$_2$, —$SO_3$N(R)$_2$, —P(R)$_3$, —P(O)(R)$_3$, —OSi(R)$_3$, —OB(R)$_2$, —C(W)R and —WC(W)R; or $R^{71}$ and $R^{72}$ taken together form a carbonyl group;

$R^{73}$ to $R^{76}$ are independently selected from hydrogen, —$C_1$-$C_{20}$ alkyl, —$C_2$-$C_{20}$ alkenyl, —$C_2$-$C_{20}$ alkynyl, —$C_3$-$C_8$ cycloalkyl, —$C_6$-$C_{14}$ aryl, —$C_5$-$C_{14}$ heteroaryl, —$C_3$-$C_{14}$ heterocyclyl, arylalkyl, heteroarylalkyl, heterocyclylalkyl, alkoxyalkyl, halo, —CN, —$NO_2$, —$C_1$-$C_{10}$ haloalkyl, —$C_1$-$C_{10}$ dihaloalkyl, —$C_1$-$C_{10}$ trihaloalkyl, —COR, —$CO_2$R, —OR, —SR, —N(R)$_2$, —NROR, —ON(R)$_2$, —SOR, —$SO_2$R, —$SO_3$R, —SON(R)$_2$, —$SO_2$N(R)$_2$, —$SO_3$N(R)$_2$, —P(R)$_3$, —P(O)(R)$_3$, —OSi(R)$_3$, —OB(R)$_2$, —C(W)R and —WC(W)R; or $R^{74}$ and $R^{75}$ taken together form a double bond or are —O—; or $R^{73}$ and $R^{74}$ or $R^{75}$ and $R^{76}$ taken together form a carbonyl group;

$R^{77}$ and $R^{78}$ are independently selected from hydrogen, —$C_1$-$C_{10}$ alkyl, —$C_2$-$C_{10}$ alkenyl and —$C_2$-$C_{10}$ alkynyl;

W is selected from —O—, —S—, —NH— and —N($C_1$-$C_6$ alkyl)-;

R is selected from hydrogen, —$C_1$-$C_{20}$ alkyl, —$C_2$-$C_{20}$ alkenyl, —$C_2$-$C_{20}$ alkynyl, —$C_3$-$C_8$ cycloalkyl, —$C_6$-$C_{14}$ aryl, —$C_5$-$C_{14}$ heteroaryl, —$C_3$-$C_{14}$ heterocyclyl, arylalkyl, heteroarylalkyl, heterocyclylalkyl, —$C_1$-$C_{10}$ haloalkyl, —$C_1$-$C_{10}$ dihaloalkyl and —$C_1$-$C_{10}$ trihaloalkyl;

p and q are independently 0 or 1; and
r is an integer from 1 to 8;
wherein each alkyl, alkenyl, alkynyl, cycloalkyl, aryl, heterocyclyl and heteroaryl is optionally substituted;
or a pharmaceutically acceptable salt thereof.

2. The method according to claim 1, wherein in the compound of formula (II), X, Y and Z are independently selected from —O— and —S—;

$R^{50}$ is selected from —$CH_3$, —$C_3$-$C_8$ cycloalkyl, aryl, heterocyclyl and heteroaryl;

$R^{51}$, $R^{52}$, $R^{57}$, $R^{58}$, $R^{61}$, $R^{62}$, $R^{67}$, $R^{68}$, $R^{69}$ and $R^{70}$ are independently selected from hydrogen, —$C_1$-$C_{20}$ alkyl, —$C_2$-$C_{20}$ alkenyl, —$C_2$-$C_{20}$ alkynyl, —$C_3$-$C_8$ cycloalkyl, —$C_6$-$C_{14}$ aryl, —$C_5$-$C_{14}$ heteroaryl, —$C_3$-$C_{14}$ heterocyclyl, arylalkyl, heteroarylalkyl, heterocyclylalkyl, alkoxyalkyl, halo, —CN, —$NO_2$, —$C_1$-$C_{10}$ haloalkyl, —$C_1$-$C_{10}$ dihaloalkyl, —$C_1$-$C_{10}$ trihaloalkyl, —COR, —$CO_2$R, —OR, —SR, —N(R)$_2$, —NROR, —ON(R)$_2$, —SOR, —$SO_2$R, —$SO_3$R, —SON(R)$_2$, —$SO_2$N(R)$_2$, —$SO_3$N(R)$_2$, —P(R)$_3$, —P(O)(R)$_3$, —OSi(R)$_3$, —OB(R)$_2$, —C(W)R and —WC(W)R;

$R^{53}$ to $R^{56}$ are independently selected from hydrogen, —$C_1$-$C_{20}$ alkyl, —$C_2$-$C_{20}$ alkenyl, —$C_2$-$C_{20}$ alkynyl, —$C_3$-$C_8$ cycloalkyl, —$C_6$-$C_{14}$ aryl, —$C_5$-$C_{14}$ heteroaryl, —$C_3$-$C_{14}$ heterocyclyl, arylalkyl, heteroarylalkyl, heterocyclylalkyl, alkoxyalkyl, halo, —CN, —$NO_2$, —$C_1$-$C_{10}$ haloalkyl, —$C_1$-$C_{10}$ dihaloalkyl, —$C_1$-$C_{10}$ trihaloalkyl, —COR, —$CO_2$R, —OR, —SR, —N(R)$_2$, —NROR, —ON(R)$_2$, —SOR, —$SO_2$R, —SO$_3$R, —SON(R)$_2$, —SO$_2$N(R)$_2$, —SO$_3$N(R)$_2$, —P(R)$_3$, —P(O)(R)$_3$, —OSi(R)$_3$, —OB(R)$_2$, —C(W)R and —WC(W)R; or R$^{54}$ and R$^{55}$ taken together form a double bond or —O—;

R$^{59}$ is hydrogen and R$^{60}$ is selected from —OH, —OC$_1$-C$_{10}$ alkyl, —OC$_2$-C$_{10}$ alkenyl, —Ocycloalkyl, —Oaryl, —Oheterocyclyl, —Oheteroaryl, —OC$_1$-C$_{10}$ alkylcycloalkyl, —OC$_1$-C$_{10}$ alkylaryl, —OC$_1$-C$_{10}$ alkylheterocyclyl, —OC$_1$-C$_{10}$ alkylheteroaryl and —OC(O)R; or R$^{59}$ and R$^{60}$ taken together form a carbonyl group;

R$^{63}$ and R$^{64}$ are independently selected from hydrogen, —C$_1$-C$_{20}$ alkyl, —C$_2$-C$_{20}$ alkenyl, —C$_2$-C$_{20}$ alkynyl, —C$_3$-C$_8$ cycloalkyl, —C$_6$-C$_{14}$ aryl, —C$_5$-C$_{14}$ heteroaryl, —C$_3$-C$_{14}$ heterocyclyl, arylalkyl, heteroarylalkyl, heterocyclylalkyl, alkoxyalkyl, halo, —CN, —NO$_2$, —C$_1$-C$_{10}$ haloalkyl, —C$_1$-C$_{10}$ dihaloalkyl, —C$_1$-C$_{10}$ trihaloalkyl, —COR, —CO$_2$R, —OR, —SR, —N(R)$_2$, —NROR, —ON(R)$_2$, —SOR, —SO$_2$R, —SO$_3$R, —SON(R)$_2$, —SO$_2$N(R)$_2$, —SO$_3$N(R)$_2$, —P(R)$_3$, —P(O)(R)$_3$, —OSi(R)$_3$, —OB(R)$_2$, —C(W)R and —WC(W)R;

R$^{65}$ is hydrogen and R$^{66}$ is selected from —OH, —OC$_1$-C$_{10}$ alkyl, —OC$_2$-C$_{10}$ alkenyl, —Ocycloalkyl, —Oaryl, —Oheterocyclyl, —Oheteroaryl, —OC$_1$-C$_{10}$ alkylcycloalkyl, —OC$_1$-C$_{10}$ alkylaryl, —OC$_1$-C$_{10}$ alkylheterocyclyl, —OC$_1$-C$_{10}$ alkylheteroaryl and —OC(O)R; or R$^{65}$ and R$^{66}$ taken together form a carbonyl group; or R$^{64}$ and R$^{65}$ taken together form a double bond;

R$^{71}$ is hydrogen and R$^{72}$ is selected from —OH, —OC$_1$-C$_{10}$ alkyl, —OC$_2$-C$_{10}$ alkenyl, —Ocycloalkyl, —Oaryl, —Oheterocyclyl, —Oheteroaryl, —OC$_1$-C$_{10}$ alkylcycloalkyl, —OC$_1$-C$_{10}$ alkylaryl, —OC$_1$-C$_{10}$ alkylheterocyclyl, —OC$_1$-C$_{10}$ alkylheteroaryl and —OC(O)R; or R$^{71}$ and R$^{72}$ taken together form a carbonyl group;

R$^{73}$ to R$^{76}$ are independently selected from hydrogen, —C$_1$-C$_{20}$ alkyl, —C$_2$-C$_{20}$ alkenyl, —C$_2$-C$_{20}$ alkynyl, —C$_3$-C$_8$ cycloalkyl, —C$_6$-C$_{14}$ aryl, —C$_5$-C$_{14}$ heteroaryl, —C$_3$-C$_{14}$ heterocyclyl, arylalkyl, heteroarylalkyl, heterocyclylalkyl, alkoxyalkyl, halo, —CN, —NO$_2$, —C$_1$-C$_{10}$ haloalkyl, —C$_1$-C$_{10}$ dihaloalkyl, —C$_1$-C$_{10}$ trihaloalkyl, —COR, —CO$_2$R, —OR, —SR, —N(R)$_2$, —NROR, —ON(R)$_2$, —SOR, —SO$_2$R, —SO$_3$R, —SON(R)$_2$, —SO$_2$N(R)$_2$, —SO$_3$N(R)$_2$, —P(R)$_3$, —P(O)(R)$_3$, —OSi(R)$_3$, —OB(R)$_2$, —C(W)R and —WC(W)R; or R$^{74}$ and R$^{75}$ taken together form a double bond or —O—;

R$^{77}$ and R$^{78}$ are independently selected from hydrogen and —C$_1$-C$_{10}$ alkyl;

W is selected from —O—, —S—, —NH— and —N(C$_1$-C$_6$ alkyl)-;

R is selected from hydrogen, —C$_1$-C$_{20}$ alkyl, —C$_2$-C$_{20}$ alkenyl, —C$_2$-C$_{20}$ alkynyl, —C$_3$-C$_8$ cycloalkyl, —C$_6$-C$_{14}$ aryl, —C$_5$-C$_{14}$ heteroaryl, —C$_3$-C$_{14}$ heterocyclyl, arylalkyl, heteroarylalkyl, heterocyclylalkyl, —C$_1$-C$_{10}$ haloalkyl, —C$_1$-C$_{10}$ dihaloalkyl and —C$_1$-C$_{10}$ trihaloalkyl;

p and q are 0 or 1; and r is an integer from 1 to 8;

wherein each alkyl, alkenyl, alkynyl, cycloalkyl, aryl, heterocyclyl and heteroaryl is optionally substituted;

or a pharmaceutically, agriculturally or pesticidally acceptable salt thereof.

3. The method according to claim 1 wherein the compound of formula (II) is a compound of formula (III):

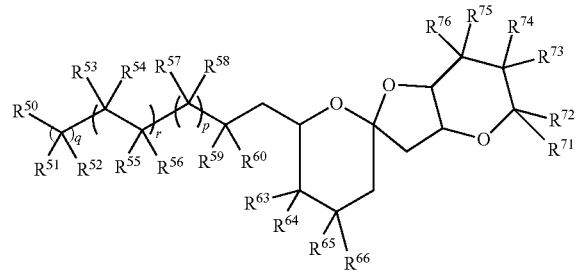

III wherein:

R$^{50}$ is selected from —CH$_3$, —C$_3$-C$_8$ cycloalkyl, aryl, heterocyclyl and heteroaryl;

R$^{51}$, R$^{52}$, R$^{57}$ and R$^{58}$ are independently selected from hydrogen, —C$_1$-C$_{20}$ alkyl, —C$_2$-C$_{20}$ alkenyl, —C$_2$-C$_{20}$ alkynyl, —C$_3$-C$_8$ cycloalkyl, —C$_6$-C$_{14}$ aryl, —C$_5$-C$_{14}$ heteroaryl, —C$_3$-C$_{14}$ heterocyclyl, arylalkyl, heteroarylalkyl, heterocyclylalkyl, alkoxyalkyl, halo, —CN, —NO$_2$, —C$_1$-C$_{10}$ haloalkyl, —C$_1$-C$_{10}$ dihaloalkyl, —C$_1$-C$_{10}$ trihaloalkyl, —COR, —CO$_2$R, —OR, —SR, —N(R)$_2$, —NROR, —ON(R)$_2$, —SOR, —SO$_2$R, —SO$_3$R, —SON(R)$_2$, —SO$_2$N(R)$_2$, —SO$_3$N(R)$_2$, —P(R)$_3$, —P(O)(R)$_3$, —OSi(R)$_3$, —OB(R)$_2$, —C(O)R and —OC(O)R;

R$^{53}$ to R$^{56}$ are independently selected from hydrogen, —C$_1$-C$_{20}$ alkyl, —C$_2$-C$_{20}$ alkenyl, —C$_2$-C$_{20}$ alkynyl, —C$_3$-C$_8$ cycloalkyl, —C$_6$-C$_{14}$ aryl, —C$_5$-C$_{14}$ heteroaryl, —C$_3$-C$_{14}$ heterocyclyl, arylalkyl, heteroarylalkyl, heterocyclylalkyl, alkoxyalkyl, halo, —CN, —NO$_2$, —C$_1$-C$_{10}$ haloalkyl, —C$_1$-C$_{10}$ dihaloalkyl, —C$_1$-C$_{10}$ trihaloalkyl, —COR, —CO$_2$R, —OR, —SR, —N(R)$_2$, —NROR, —ON(R)$_2$, —SOR, —SO$_2$R, —SO$_3$R, —SON(R)$_2$, —SO$_2$N(R)$_2$, —SO$_3$N(R)$_2$, —P(R)$_3$, —P(O)(R)$_3$, —OSi(R)$_3$, —OB(R)$_2$, —C(O)R and —OC(O)R; or R$^{54}$ and R$^{55}$ taken together form a double bond or —O—;

R$^{59}$ is hydrogen and R$^{60}$ is selected from —OH, —OC$_1$-C$_{10}$ alkyl, —OC$_2$-C$_{10}$ alkenyl, —Ocycloalkyl, —Oaryl, —Oheterocyclyl, —Oheteroaryl, —OC$_1$-C$_{10}$ alkylcycloalkyl, —OC$_1$-C$_{10}$ alkylaryl, —OC$_1$-C$_{10}$ alkylheterocyclyl, —OC$_1$-C$_{10}$ alkylheteroaryl and —OC(O)R; or R$^{59}$ and R$^{60}$ taken together form a carbonyl group;

R$^{63}$ and R$^{64}$ hydrogen;

R$^{65}$ is hydrogen and R$^{66}$ is selected from —OH, —OC$_1$-C$_{10}$ alkyl, —OC$_2$-C$_{10}$ alkenyl, —Ocycloalkyl, —Oaryl, —Oheterocyclyl, —Oheteroaryl, —OC$_1$-C$_{10}$ alkylcycloalkyl, —OC$_1$-C$_{10}$ alkylaryl, —OC$_1$-C$_{10}$ alkylheterocyclyl, —OC$_1$-C$_{10}$ alkylheteroaryl and —OC(O)R; or R$^{65}$ and R$^{66}$ taken together form a carbonyl group; or R$^{64}$ and R$^{65}$ taken together form a double bond;

R$^{71}$ is hydrogen and R$^{72}$ is selected from —OH, —OC$_1$-C$_{10}$ alkyl, —OC$_2$-C$_{10}$ alkenyl, —Ocycloalkyl, —Oaryl, —Oheterocyclyl, —Oheteroaryl, —OC$_1$-C$_{10}$ alkylcycloalkyl, —OC$_1$-C$_{10}$ alkylaryl, —OC$_1$-C$_{10}$ alkylheterocyclyl, —OC$_1$-C$_{10}$ alkylheteroaryl and —OC(O)R; or R$^{71}$ and R$^{72}$ taken together form a carbonyl group;

R$^{73}$ to R$^{76}$ are independently selected from hydrogen, —C$_1$-C$_{20}$ alkyl, —C$_2$-C$_{20}$ alkenyl, —C$_2$-C$_{20}$ alkynyl, —C$_3$-C$_8$ cycloalkyl, —C$_6$-C$_{14}$ aryl, —C$_5$-C$_{14}$ heteroaryl, —C$_3$-C$_{14}$ heterocyclyl, arylalkyl, heteroarylalkyl, heterocyclylalkyl, alkoxyalkyl, halo, —CN, —NO$_2$, —C$_1$-C$_{10}$ haloalkyl, —C$_1$-C$_{10}$ dihaloalkyl, —$C_1$-$C_{10}$ trihaloalkyl, —COR, —$CO_2$R, —OR, —SR, —N(R)$_2$, —NROR, —ON(R)$_2$, —SOR, —$SO_2$R, —$SO_3$R, —SON(R)$_2$, —$SO_2$N(R)$_2$, —$SO_3$N(R)$_2$, —P(R)$_3$, —P(O)(R)$_3$, —OSi(R)$_3$, —OB(R)$_2$, —C(W)R and —WC(W)R; or $R^{74}$ and $R^{75}$ taken together form a double bond or —O—;

R is selected from hydrogen, —$C_1$-$C_{20}$ alkyl, —$C_2$-$C_{20}$ alkenyl, —$C_2$-$C_{20}$ alkynyl, —$C_3$-$C_8$ cycloalkyl, —$C_6$-$C_{14}$ aryl, —$C_5$-$C_{14}$ heteroaryl, —$C_3$-$C_{14}$ heterocyclyl, arylalkyl, heteroarylalkyl, heterocyclylalkyl, —$C_1$-$C_{10}$ haloalkyl, —$C_1$-$C_{10}$ dihaloalkyl and —$C_1$-$C_{10}$ trihaloalkyl;

p and q are 0 or 1; and r is an integer from 1 to 8;

wherein each alkyl, alkenyl, alkynyl, cycloalkyl, aryl, heterocyclyl and heteroaryl is optionally substituted;

or a pharmaceutically, agriculturally or pesticidally acceptable salt thereof.

4. The method according to claim 1, wherein in the compound of formula (II), X, Y and Z are oxygen.

5. The method according to claim 1 wherein in the compound of formula (II), $R^{50}$ is —$CH_3$, phenyl or heteroaryl.

6. The method according to claim 1 wherein in the compound of formula (II), $R^{51}$, $R^{52}$, $R^{57}$ and $R^{58}$ are hydrogen.

7. The method according to claim 1 wherein in the compound of formula (II), $R^{53}$ to $R^{56}$ are independently selected from hydrogen, —$C_1$-$C_6$ alkyl, —$COC_1$-$C_6$ alkyl, —$CO_2$H, $CO_2C_1$-$C_6$ alkyl, —OH, —$OC_1$-$C_6$ alkyl and —OC(O)$C_1$-$C_6$ alkyl or $R^{54}$ and $R^{55}$ taken together form a double bond or —O—.

8. The method according to claim 1 wherein in the compound of formula (II), $R^{59}$ is hydrogen and $R^{60}$ is selected from —OH, —$OC_1$-$C_{10}$ alkyl, —$OC_2$-$C_{10}$ alkenyl, —Ocycloalkyl, —Oaryl, —Oheterocyclyl, —Oheteroaryl, —$OC_1$-$C_{10}$ alkylcycloalkyl, —$OC_1$-$C_{10}$ alkylaryl, —$OC_1$-$C_{10}$ alkylheterocyclyl, —$OC_1$-$C_{10}$ alkylheteroaryl and —OC(O)R; or $R^{59}$ and $R^{60}$ taken together form a carbonyl group.

9. The method according to claim 1 wherein in the compound of formula (II), $R^{61}$, $R^{62}$, $R^{67}$, $R^{68}$, $R^{69}$ and $R^{70}$ are hydrogen.

10. The method according to claim 1 wherein in the compound of formula (II), $R^{63}$ and $R^{64}$ are hydrogen.

11. The method according to claim 1 wherein in the compound of formula (II), $R^{65}$ is hydrogen and $R^{66}$ is selected from —OH, —$OC_1$-$C_{10}$ alkyl, —$OC_2$-$C_{10}$ alkenyl, —Ocycloalkyl, —Oaryl, —Oheterocyclyl, —Oheteroaryl, —$OC_1$-$C_{10}$ alkylcycloalkyl, —$OC_1$-$C_{10}$ alkylaryl, —$OC_1$-$C_{10}$ alkylheterocyclyl, —$OC_1$-$C_{10}$ alkylheteroaryl and —OC(O)R; or $R^{59}$ and $R^{60}$ taken together form a carbonyl group.

12. The method according to claim 1 wherein in the compound of formula (II), $R^{64}$ and $R^{65}$ form a double bond.

13. The method according to claim 1 wherein in the compound of formula (II), $R^{71}$ is hydrogen and $R^{72}$ is selected from —OH, —$OC_1$-$C_{10}$ alkyl, —$OC_2$-$C_{10}$ alkenyl, —Ocycloalkyl, —Oaryl, —Oheterocyclyl, —Oheteroaryl, —$OC_1$-$C_{10}$ alkylcycloalkyl, —$OC_1$-$C_{10}$ alkylaryl, —$OC_1$-$C_{10}$ alkylheterocyclyl, —$OC_1$-$C_{10}$ alkylheteroaryl and —OC(O)R; or $R^{71}$ and $R^{72}$ taken together form a carbonyl group.

14. The method according to claim 1 wherein in the compound of formula (II), $R^{73}$, $R^{74}$, $R^{75}$ and $R^{76}$ are hydrogen, or $R^{73}$ and $R^{76}$ are hydrogen and $R^{74}$ and $R^{75}$ taken together form a double bond or —O—.

15. The method according to claim 1 wherein in the compound of formula (II), $R^{77}$ and $R^{78}$ are independently hydrogen or methyl.

16. The method according to claim 1 wherein the infection being treated is a bacterial infection.

17. The method according to claim 16 wherein the bacterial infection is caused by a bacteria selected from a Genus from the groups of *Bacillus*, *Staphylococcus*, *Streptococcus*, *Aerococcus*, *Gemella*, *Corynebacterium*, *Listeria*, *Kurthia*, *Lactobacillus*, *Erysipelothrix*, *Arachnia*, *Actinomyces*, *Propionibacterium*, *Rothia*, *Bifidobacterium*, *Clostridium*, *Eubacterium*, *Nocardia* and *Mycobacterium*.

18. The method according to claim 17 wherein the bacteria is selected from the group consisting of *Bacillus subtilis*, *Bacillus anthracis*, *Bacillus cereus*, *Bacillus fermis*, *Bacillus licheniformis*, *Bacillus megaterium*, *Bacillus pumilus*, *Bacillus coagulans*, *Bacillus pantothenticus*, *Bacillus alvei*, *Bacillus brevis*, *Bacillus circulans*, *Bacillus laterosporus*, *Bacillus macerans*, *Bacillus polymyxa*, *Bacillus stearothermophilus*, *Bacillus thuringiensis*, *Bacillus sphaericus*, *Staphylococcus aureus*, *Staphylococcus epidermidis*, *Staphylococcus haemolyticus*, *Staphylococcus saprophyticus*, *Streptococcus pyogenes*, *Streptococcus pneumoniae*, *Streptococcus agalactiae*, *Streptococcus pyogenes*, *Streptococcus agalactiae*, *Streptococcus dysgalactiae*, *Streptococcus equisimilis*, *Streptococcus equi*, *Streptococcus zooepidemicus*, *Streptococcus anginosus*, *Streptococcus salivarius*, *Streptococcus milleri*, *Streptococcus sanguis*, *Streptococcus mitior*, *Streptococcus mutans*, *Streptococcus faecalis*, *Streptococcus faecium*, *Streptococcus bovis*, *Streptococcus equinus*, *Streptococcus uberus* and *Streptococcus avium*.

19. The method according to claim 1 wherein the infection is a parasitic infection caused by a helminth selected from the group consisting of nematodes, trematodes and cestodes.

20. The method according to claim 19 wherein the helminth is selected from the group consisting of *Haemonchus contortus*, *Trichinella spiralis*, *Haemonchus placei*, *Bursaphelenchus xylophilus*, *Ostertagia circumcincta*, *Ostertagi ostertagi*, *Mecistocirrus digitatus*, *Trychostrongylus axei*, *Trichuris trichiura*, *Trichuris vulpis*, *Trichuris campanula*, *Trichuris suis*, *Trichuris ovis*, *Bunostomum trigonocephalum*, *Bunostomum phleboyomum*, *Oesophagostomum columbianum*, *Oesophagostomum radiatum*, *Cooperia curticei*, *Cooperia punctata*, *Cooperia oncophora*, *Cooperia pectinata*, *Strongyloides papillosus*, *Chabertia ovina*, *Ancylostoma duodenale*, *Ancylostoma braziliense*, *Ancylostoma tubaeforme*, *Ancylostoma caninum*, *Ascaris lumbricoides*, *Enterobius vermicularis*, *Enterobius gregorii*, *Ascaris lumbricoides*, *Paragonimus Westermani*, *Clonorchis sinensis*, *Fasciola hepatica*, *Taenia solium*, *Taenia saginata*, *Capillaria aerophile*, *Necator americanus* or from a species of the genus *Trichuris*, *Baylisascaris*, *Aphelenchoides*, *Meliodogyne*, *Heterodera*, *Globodera*, *Nacobbus*, *Pratylenchus*, *Ditylenchus*, *Xiphinema*, *Longidorus*, *Trichodorus* and *Nematodirus*.

21. The method according to claim 1 wherein the infection is a protozoan infection is caused by a protozoa selected from the group consisting of *Giardia* spp., *Trichomonas* spp., African trypanosomiasis, amoebic dysentery, babesiosis, balantidial dysentery, Chaga's disease, coccidiosis, malaria and toxoplasmosis.

22. The method according to claim 21 wherein the protozoan infection is caused by *Giardia* spp. or *Trichomonas* spp.

23. A method of treating an inflammatory disorder comprising administering to a subject compound of formula (II):

II

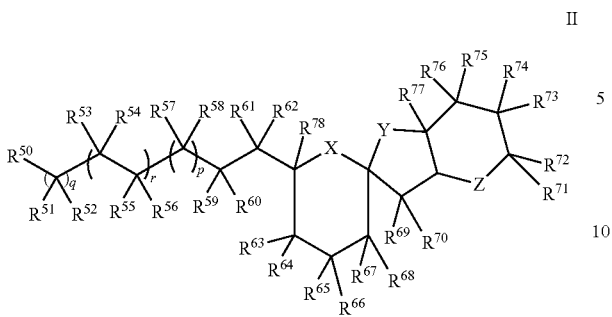

wherein

X, Y and Z are independently selected from —O—, —S—, —NH—, —N($C_1$-$C_6$ alkyl)- and —CH$_2$—;

$R^{50}$ is selected from —CH$_3$, —$C_3$-$C_8$ cycloalkyl, aryl, heterocyclyl and heteroaryl;

$R^{51}$, $R^{52}$, $R^{57}$, $R^{58}$, $R^{61}$, $R^{62}$, $R^{67}$, $R^{68}$, $R^{69}$ and $R^{70}$ are independently selected from hydrogen, —$C_1$-$C_{20}$ alkyl, —$C_2$-$C_{20}$ alkenyl, —$C_2$-$C_{20}$ alkynyl, —$C_3$-$C_8$ cycloalkyl, —$C_6$-$C_{14}$ aryl, —$C_5$-$C_{14}$ heteroaryl, —$C_3$-$C_{14}$ heterocyclyl, arylalkyl, heteroarylalkyl, heterocyclylalkyl, alkoxyalkyl, halo, —CN, —NO$_2$, —$C_1$-$C_{10}$ haloalkyl, —$C_1$-$C_{10}$ dihaloalkyl, —$C_1$-$C_{10}$ trihaloalkyl, —COR, —CO$_2$R, —OR, —SR, —N(R)$_2$, —NROR, —ON(R)$_2$, —SOR, —SO$_2$R, —SO$_3$R, —SON(R)$_2$, —SO$_2$N(R)$_2$, —SO$_3$N(R)$_2$, —P(R)$_3$, —P(O)(R)$_3$, —OSi(R)$_3$, —OB(R)$_2$, —C(W)R and —WC(W)R;

$R^{53}$ to $R^{56}$ are independently selected from hydrogen, —$C_1$-$C_{20}$ alkyl, —$C_2$-$C_{20}$ alkenyl, —$C_2$-$C_{20}$ alkynyl, —$C_3$-$C_8$ cycloalkyl, —$C_6$-$C_{14}$ aryl, —$C_5$-$C_{14}$ heteroaryl, —$C_3$-$C_{14}$ heterocyclyl, arylalkyl, heteroarylalkyl, heterocyclylalkyl, alkoxyalkyl, halo, —CN, —NO$_2$, —$C_1$-$C_{10}$ haloalkyl, —$C_1$-$C_{10}$ dihaloalkyl, —$C_1$-$C_{10}$ trihaloalkyl, —COR, —CO$_2$R, —OR, —SR, —N(R)$_2$, —NROR, —ON(R)$_2$, —SOR, —SO$_2$R, —SO$_3$R, —SON(R)$_2$, —SO$_2$N(R)$_2$, —SO$_3$N(R)$_2$, —P(R)$_3$, —P(O)(R)$_3$, —OSi(R)$_3$, —OB(R)$_2$, —C(W)R and —WC(W)R; or $R^{54}$ and $R^{55}$ taken together form a double bond or are —O—; or $R^{53}$ and $R^{54}$ or $R^{55}$ and $R^{56}$ taken together form a carbonyl group;

$R^{59}$ and $R^{60}$ are independently selected from hydrogen, —$C_1$-$C_{20}$ alkyl, —$C_2$-$C_{20}$ alkenyl, —$C_2$-$C_{20}$ alkynyl, —$C_3$-$C_8$ cycloalkyl, —$C_6$-$C_{14}$ aryl, —$C_5$-$C_{14}$ heteroaryl, —$C_3$-$C_{14}$ heterocyclyl, arylalkyl, heteroarylalkyl, heterocyclylalkyl, alkoxyalkyl, halo, —CN, —NO$_2$, —$C_1$-$C_{10}$ haloalkyl, —$C_1$-$C_{10}$ dihaloalkyl, —$C_1$-$C_{10}$ trihaloalkyl, —COR, —CO$_2$R, —OR, —SR, —N(R)$_2$, —NROR, —ON(R)$_2$, —SOR, —SO$_2$R, —SO$_3$R, —SON(R)$_2$, —SO$_2$N(R)$_2$, —SO$_3$N(R)$_2$, —P(R)$_3$, —P(O)(R)$_3$, —OSi(R)$_3$, —OB(R)$_2$, —C(W)R and —WC(W)R; or $R^{59}$ and $R^{60}$ taken together form a carbonyl group;

$R^{63}$ to $R^{66}$ are independently selected from hydrogen, —$C_1$-$C_{20}$ alkyl, —$C_2$-$C_{20}$ alkenyl, —$C_2$-$C_{20}$ alkynyl, —$C_3$-$C_8$ cycloalkyl, —$C_6$-$C_{14}$ aryl, —$C_5$-$C_{14}$ heteroaryl, —$C_3$-$C_{14}$ heterocyclyl, arylalkyl, heteroarylalkyl, heterocyclylalkyl, alkoxyalkyl, halo, —CN, —NO$_2$, —$C_1$-$C_{10}$ haloalkyl, —$C_1$-$C_{10}$ dihaloalkyl, —$C_1$-$C_{10}$ trihaloalkyl, —COR, —CO$_2$R, —OR, —SR, —N(R)$_2$, —NROR, —ON(R)$_2$, —SOR, —SO$_2$R, —SO$_3$R, —SON(R)$_2$, —SO$_2$N(R)$_2$, —SO$_3$N(R)$_2$, —P(R)$_3$, —P(O)(R)$_3$, —OSi(R)$_3$, —OB(R)$_2$, —C(W)R and —WC(W)R; or $R^{64}$ and $R^{65}$ taken together form a double bond or are —O—; or $R^{63}$ and $R^{64}$ or $R^{65}$ and $R^{66}$ taken together form a carbonyl group;

$R^{71}$ and $R^{72}$ are independently selected from hydrogen, —$C_1$-$C_{20}$ alkyl, —$C_2$-$C_{20}$ alkenyl, —$C_2$-$C_{20}$ alkynyl, —$C_3$-$C_8$ cycloalkyl, —$C_6$-$C_{14}$ aryl, —$C_5$-$C_{14}$ heteroaryl, —$C_3$-$C_{14}$ heterocyclyl, arylalkyl, heteroarylalkyl, heterocyclylalkyl, alkoxyalkyl, halo, —CN, —NO$_2$, —$C_1$-$C_{10}$ haloalkyl, —$C_1$-$C_{10}$ dihaloalkyl, —$C_1$-$C_{10}$ trihaloalkyl, —COR, —CO$_2$R, —OR, —SR, —N(R)$_2$, —NROR, —ON(R)$_2$, —SOR, —SO$_2$R, —SO$_3$R, —SON(R)$_2$, —SO$_2$N(R)$_2$, —SO$_3$N(R)$_2$, —P(R)$_3$, —P(O)(R)$_3$, —OSi(R)$_3$, —OB(R)$_2$, —C(W)R and —WC(W)R; or $R^{71}$ and $R^{72}$ taken together form a carbonyl group;

$R^{73}$ to $R^{76}$ are independently selected from hydrogen, —$C_1$-$C_{20}$ alkyl, —$C_2$-$C_{20}$ alkenyl, —$C_2$-$C_{20}$ alkynyl, —$C_3$-$C_8$ cycloalkyl, —$C_6$-$C_{14}$ aryl, —$C_5$-$C_{14}$ heteroaryl, —$C_3$-$C_{14}$ heterocyclyl, arylalkyl, heteroarylalkyl, heterocyclylalkyl, alkoxyalkyl, halo, —CN, —NO$_2$, —$C_1$-$C_{10}$ haloalkyl, —$C_1$-$C_{10}$ dihaloalkyl, —$C_1$-$C_{10}$ trihaloalkyl, —COR, —CO$_2$R, —OR, —SR, —N(R)$_2$, —NROR, —ON(R)$_2$, —SOR, —SO$_2$R, —SO$_3$R, —SON(R)$_2$, —SO$_2$N(R)$_2$, —SO$_3$N(R)$_2$, —P(R)$_3$, —P(O)(R)$_3$, —OSi(R)$_3$, —OB(R)$_2$, —C(W)R and —WC(W)R; or $R^{74}$ and $R^{75}$ taken together form a double bond or are —O—; or $R^{73}$ and $R^{74}$ or $R^{75}$ and $R^{76}$ taken together form a carbonyl group;

$R^{77}$ and $R^{78}$ are independently selected from hydrogen, —$C_1$-$C_{10}$ alkyl, —$C_2$-$C_{10}$ alkenyl and —$C_2$-$C_{10}$ alkynyl;

W is selected from —O—, —S—, —NH— and —N($C_1$-$C_6$ alkyl)-;

R is selected from hydrogen, —$C_1$-$C_{20}$ alkyl, —$C_2$-$C_{20}$ alkenyl, —$C_2$-$C_{20}$ alkynyl, —$C_3$-$C_8$ cycloalkyl, —$C_6$-$C_{14}$ aryl, —$C_5$-$C_{14}$ heteroaryl, —$C_3$-$C_{14}$ heterocyclyl, arylalkyl, heteroarylalkyl, heterocyclylalkyl, —$C_1$-$C_{10}$ haloalkyl, —$C_1$-$C_{10}$ dihaloalkyl and —$C_1$-$C_{10}$ trihaloalkyl;

p and q are independently 0 or 1; and r is an integer from 1 to 8;

wherein each alkyl, alkenyl, alkynyl, cycloalkyl, aryl, heterocyclyl and heteroaryl is optionally substituted;

or a pharmaceutically acceptable salt thereof.

24. The method according to claim 23 wherein the inflammatory disorder is selected from the group consisting of general inflammation, rheumatoid arthritis, colitis or an autoimmune disorder.

25. The method according to claim 23 wherein the inflammatory disorder requires immunosuppression.

26. A method of diuresis comprising administering to a subject, a compound of formula (II):

II

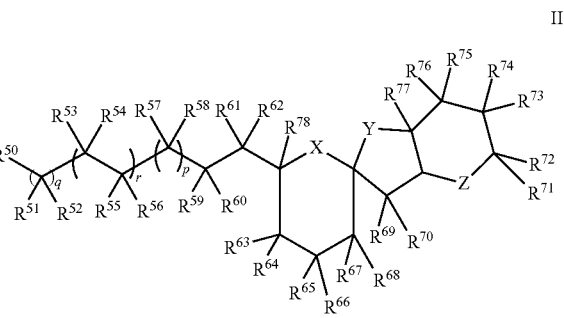

wherein
- X, Y and Z are independently selected from —O—, —S—, —NH—, —N($C_1$-$C_6$ alkyl)- and —$CH_2$—;
- $R^{50}$ is selected from —$CH_3$, —$C_3$-$C_8$ cycloalkyl, aryl, heterocyclyl and heteroaryl;
- $R^{51}$, $R^{52}$, $R^{57}$, $R^{58}$, $R^{61}$, $R^{62}$, $R^{67}$, $R^{68}$, $R^{69}$ and $R^{70}$ are independently selected from hydrogen, —$C_1$-$C_{20}$ alkyl, —$C_2$-$C_{20}$ alkenyl, —$C_2$-$C_{20}$ alkynyl, —$C_3$-$C_8$ cycloalkyl, —$C_6$-$C_{14}$ aryl, —$C_5$-$C_{14}$ heteroaryl, —$C_3$-$C_{14}$ heterocyclyl, arylalkyl, heteroarylalkyl, heterocyclylalkyl, alkoxyalkyl, halo, —CN, —$NO_2$, —$C_1$-$C_{10}$ haloalkyl, —$C_1$-$C_{10}$ dihaloalkyl, —$C_1$-$C_{10}$ trihaloalkyl, —COR, —$CO_2$R, —OR, —SR, —N(R)$_2$, —NROR, —ON(R)$_2$, —SOR, —$SO_2$R, —$SO_3$R, —SON(R)$_2$, —$SO_2$N(R)$_2$, —$SO_3$N(R)$_2$, —P(R)$_3$, —P(O)(R)$_3$, —OSi(R)$_3$, —OB(R)$_2$, —C(W)R and —WC(W)R;
- $R^{53}$ to $R^{56}$ are independently selected from hydrogen, —$C_1$-$C_{20}$ alkyl, —$C_2$-$C_{20}$ alkenyl, —$C_2$-$C_{20}$ alkynyl, —$C_3$-$C_8$ cycloalkyl, —$C_6$-$C_{14}$ aryl, —$C_5$-$C_{14}$ heteroaryl, —$C_3$-$C_{14}$ heterocyclyl, arylalkyl, heteroarylalkyl, heterocyclylalkyl, alkoxyalkyl, halo, —CN, —$NO_2$, —$C_1$-$C_{10}$ haloalkyl, —$C_1$-$C_{10}$ dihaloalkyl, —$C_1$-$C_{10}$ trihaloalkyl, —COR, —$CO_2$R, —OR, —SR, —N(R)$_2$, —NROR, —ON(R)$_2$, —SOR, —$SO_2$R, —$SO_3$R, —SON(R)$_2$, —$SO_2$N(R)$_2$, —$SO_3$N(R)$_2$, —P(R)$_3$, —P(O)(R)$_3$, —OSi(R)$_3$, —OB(R)$_2$, —C(W)R and —WC(W)R; or $R^{54}$ and $R^{55}$ taken together form a double bond or are —O—; or $R^{53}$ and $R^{54}$ or $R^{55}$ and $R^{56}$ taken together form a carbonyl group;
- $R^{59}$ and $R^{60}$ are independently selected from hydrogen, —$C_1$-$C_{20}$ alkyl, —$C_2$-$C_{20}$ alkenyl, —$C_2$-$C_{20}$ alkynyl, —$C_3$-$C_8$ cycloalkyl, —$C_6$-$C_{14}$ aryl, —$C_5$-$C_{14}$ heteroaryl, —$C_3$-$C_{14}$ heterocyclyl, arylalkyl, heteroarylalkyl, heterocyclylalkyl, alkoxyalkyl, halo, —CN, —$NO_2$, —$C_1$-$C_{10}$ haloalkyl, —$C_1$-$C_{10}$ dihaloalkyl, —$C_1$-$C_{10}$ trihaloalkyl, —COR, —$CO_2$R, —OR, —SR, —N(R)$_2$, —NROR, —ON(R)$_2$, —SOR, —$SO_2$R, —$SO_3$R, —SON(R)$_2$, —$SO_2$N(R)$_2$, —$SO_3$N(R)$_2$, —P(R)$_3$, —P(O)(R)$_3$, —OSi(R)$_3$, —OB(R)$_2$, —C(W)R and —WC(W)R; or $R^{59}$ and $R^{60}$ taken together form a carbonyl group;
- $R^{63}$ to $R^{66}$ are independently selected from hydrogen, —$C_1$-$C_{20}$ alkyl, —$C_2$-$C_{20}$ alkenyl, —$C_2$-$C_{20}$ alkynyl, —$C_3$-$C_8$ cycloalkyl, —$C_6$-$C_{14}$ aryl, —$C_5$-$C_{14}$ heteroaryl, —$C_3$-$C_{14}$ heterocyclyl, arylalkyl, heteroarylalkyl, heterocyclylalkyl, alkoxyalkyl, halo, —CN, —$NO_2$, —$C_1$-$C_{10}$ haloalkyl, —$C_1$-$C_{10}$ dihaloalkyl, —$C_1$-$C_{10}$ trihaloalkyl, —COR, —$CO_2$R, —OR, —SR, —N(R)$_2$, —NROR, —ON(R)$_2$, —SOR, —$SO_2$R, —$SO_3$R, —SON(R)$_2$, —$SO_2$N(R)$_2$, —$SO_3$N(R)$_2$, —P(R)$_3$, —P(O)(R)$_3$, —OSi(R)$_3$, —OB(R)$_2$, —C(W)R and —WC(W)R; or $R^{64}$ and $R^{65}$ taken together form a double bond or are —O—; or $R^{63}$ and $R^{64}$ or $R^{65}$ and $R^{66}$ taken together form a carbonyl group;
- $R^{71}$ and $R^{72}$ are independently selected from hydrogen, —$C_1$-$C_{20}$ alkyl, —$C_2$-$C_{20}$ alkenyl, —$C_2$-$C_{20}$ alkynyl, —$C_3$-$C_8$ cycloalkyl, —$C_6$-$C_{14}$ aryl, —$C_5$-$C_{14}$ heteroaryl, —$C_3$-$C_{14}$ heterocyclyl, arylalkyl, heteroarylalkyl, heterocyclylalkyl, alkoxyalkyl, halo, —CN, —$NO_2$, —$C_1$-$C_{10}$ haloalkyl, —$C_1$-$C_{10}$ dihaloalkyl, —$C_1$-$C_{10}$ trihaloalkyl, —COR, —$CO_2$R, —OR, —SR, —N(R)$_2$, —NROR, —ON(R)$_2$, —SOR, —$SO_2$R, —$SO_3$R, —SON(R)$_2$, —$SO_2$N(R)$_2$, —$SO_3$N(R)$_2$, —P(R)$_3$, —P(O)(R)$_3$, —OSi(R)$_3$, —OB(R)$_2$, —C(W)R and —WC(W)R; or $R^{71}$ and $R^{72}$ taken together form a carbonyl group;
- $R^{73}$ to $R^{76}$ are independently selected from hydrogen, —$C_1$-$C_{20}$ alkyl, —$C_2$-$C_{20}$ alkenyl, —$C_2$-$C_{20}$ alkynyl, —$C_3$-$C_8$ cycloalkyl, —$C_6$-$C_{14}$ aryl, —$C_5$-$C_{14}$ heteroaryl, —$C_3$-$C_{14}$ heterocyclyl, arylalkyl, heteroarylalkyl, heterocyclylalkyl, alkoxyalkyl, halo, —CN, —$NO_2$, —$C_1$-$C_{10}$ haloalkyl, —$C_1$-$C_{10}$ dihaloalkyl, —$C_1$-$C_{10}$ trihaloalkyl, —COR, —$CO_2$R, —OR, —SR, —N(R)$_2$, —NROR, —ON(R)$_2$, —SOR, —$SO_2$R, —$SO_3$R, —SON(R)$_2$, —$SO_2$N(R)$_2$, —$SO_3$N(R)$_2$, —P(R)$_3$, —P(O)(R)$_3$, —OSi(R)$_3$, —OB(R)$_2$, —C(W)R and —WC(W)R; or $R^{74}$ and $R^{75}$ taken together form a double bond or are —O—; or $R^{73}$ and $R^{74}$ or $R^{75}$ and $R^{76}$ taken together form a carbonyl group;
- $R^{77}$ and $R^{78}$ are independently selected from hydrogen, —$C_1$-$C_{10}$ alkyl, —$C_2$-$C_{10}$ alkenyl and —$C_2$-$C_{10}$ alkynyl;
- W is selected from —O—, —S—, —NH— and —N($C_1$-$C_6$ alkyl)-;
- R is selected from hydrogen, —$C_1$-$C_{20}$ alkyl, —$C_2$-$C_{20}$ alkenyl, —$C_2$-$C_{20}$ alkynyl, —$C_3$-$C_8$ cycloalkyl, —$C_6$-$C_{14}$ aryl, —$C_5$-$C_{14}$ heteroaryl, —$C_3$-$C_{14}$ heterocyclyl, arylalkyl, heteroarylalkyl, heterocyclylalkyl, —$C_1$-$C_{10}$ haloalkyl, —$C_1$-$C_{10}$ dihaloalkyl and —$C_1$-$C_{10}$ trihaloalkyl;
- p and q are independently 0 or 1; and
- r is an integer from 1 to 8;
- wherein each alkyl, alkenyl, alkynyl, cycloalkyl, aryl, heterocyclyl and heteroaryl is optionally substituted;
- or a pharmaceutically acceptable salt thereof.

\* \* \* \* \*